United States Patent
Mide et al.

(10) Patent No.: US 9,333,308 B2
(45) Date of Patent: May 10, 2016

(54) FLUID TRANSFER DEVICES

(71) Applicant: CONCEPTOMED AS, Ballstad (NO)

(72) Inventors: Christian Mide, Ballstad (NO); Marius Andresen, Oslo (NO); Rolf Blomvågnes, Rong (NO); Kevin Geers, Oslo (NO)

(73) Assignee: CONCEPTOMED AS, Ballstad (NO)

( * ) Notice: Subject to any disclaimer, the term of this patent is extended or adjusted under 35 U.S.C. 154(b) by 0 days.

(21) Appl. No.: 14/388,823

(22) PCT Filed: Apr. 30, 2013

(86) PCT No.: PCT/EP2013/059032
§ 371 (c)(1),
(2) Date: Sep. 29, 2014

(87) PCT Pub. No.: WO2013/164358
PCT Pub. Date: Nov. 7, 2013

(65) Prior Publication Data
US 2015/0320940 A1    Nov. 12, 2015

(30) Foreign Application Priority Data

Apr. 30, 2012  (EP) .................................. 12166224
Jul. 31, 2012  (EP) .................................. 12178732

(51) Int. Cl.
*A61M 5/32*   (2006.01)
*A61M 5/34*   (2006.01)
(Continued)

(52) U.S. Cl.
CPC ............ *A61M 5/3293* (2013.01); *A61M 5/3205* (2013.01); *A61M 5/344* (2013.01); *A61M 5/346* (2013.01); *A61M 5/3134* (2013.01); *A61M 2005/3206* (2013.01); *A61M 2005/341* (2013.01); *A61M 2005/5006* (2013.01)

(58) Field of Classification Search
CPC .................. A61M 2005/3206; A61M 5/3269; A61M 5/3216; A61M 5/3232; A61M 5/346
USPC .................. 604/192–198, 110, 187, 240–243
See application file for complete search history.

(56) References Cited

U.S. PATENT DOCUMENTS

| | | | |
|---|---|---|---|
| 2,875,760 | A | 3/1959 | Haber |
| 4,425,119 | A | 1/1984 | Berglund |
| 4,820,277 | A * | 4/1989 | Norelli ................ A61M 5/3216 604/192 |

(Continued)

FOREIGN PATENT DOCUMENTS

| | | |
|---|---|---|
| DE | 883 053 C | 7/1953 |
| DE | 297 07 813 U1 | 7/1997 |

(Continued)

*Primary Examiner* — Phillip Gray
(74) *Attorney, Agent, or Firm* — Sutherland Asbill & Brennan LLP

(57) ABSTRACT

A fluid transfer device such as a syringe may include a fluid chamber in communication with a male connector tip. The male connector tip is tapered to form a friction fit when inserted in a corresponding female hub. A disconnecting member, e.g., in the form of a lever member has a front surface moveable along the male connector tip between a first position proximal to the fluid chamber and a second position spaced from the first position towards a distal end of the male connector tip so as to release the friction fit. A catch is arranged to catch the female hub after it has been released from the friction fit by the lever member moving towards the second position. The catch may be released when the lever member pivots back towards the first position under the resilient bias of a spring tongue.

20 Claims, 34 Drawing Sheets

(51) Int. Cl.
*A61M 5/31* (2006.01)
*A61M 5/50* (2006.01)

(56) References Cited

U.S. PATENT DOCUMENTS

| | | | |
|---|---|---|---|
| 4,822,343 A * | 4/1989 | Beiser | A61B 5/1433 |
| | | | 600/576 |
| 4,904,244 A | 2/1990 | Harsh et al. | |
| 4,907,600 A | 3/1990 | Spencer | |
| 5,201,716 A * | 4/1993 | Richard | A61B 5/1438 |
| | | | 600/576 |
| 5,405,330 A | 4/1995 | Zunitch et al. | |
| 5,695,477 A | 12/1997 | Sfikas | |
| 5,713,876 A | 2/1998 | Bogert et al. | |
| 5,823,997 A | 10/1998 | Thorne | |
| 5,980,488 A | 11/1999 | Thorne | |

FOREIGN PATENT DOCUMENTS

| | | |
|---|---|---|
| EP | 0 747 087 A2 | 12/1996 |
| FR | 2 645 444 A1 | 10/1990 |
| FR | 2 647 351 A1 | 11/1990 |
| FR | 2 733 916 A1 | 11/1996 |
| JP | H10 179737 A | 7/1998 |
| JP | H01 120852 U | 8/1998 |
| JP | 2002 028246 A | 1/2002 |
| WO | 90/00881 A1 | 2/1990 |
| WO | 2006/045215 A1 | 5/2006 |

* cited by examiner

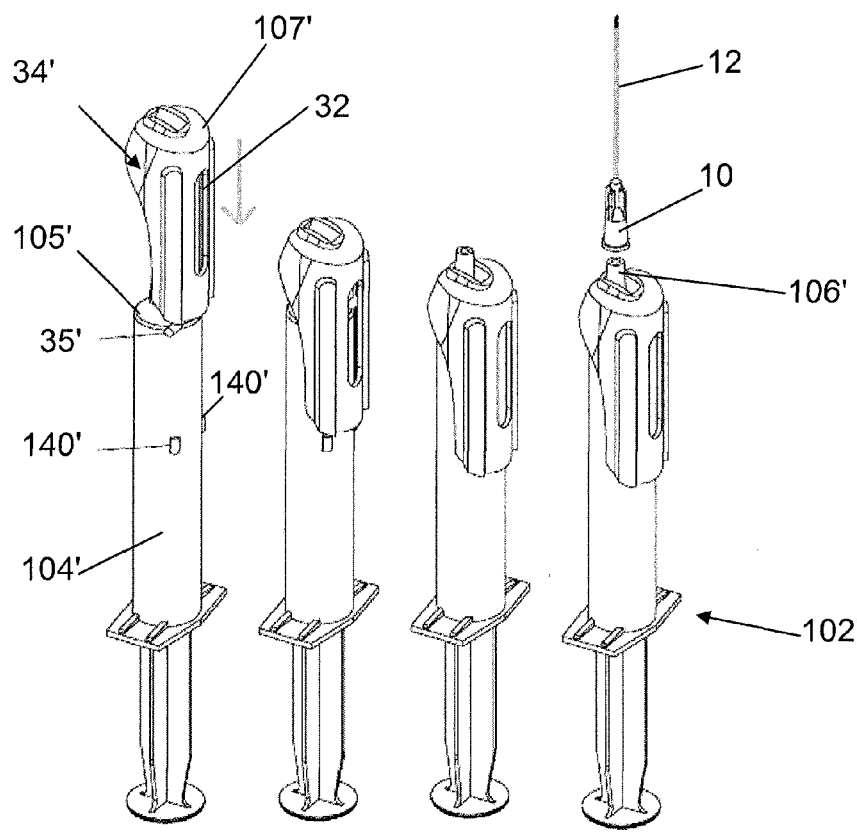
Figure 11c
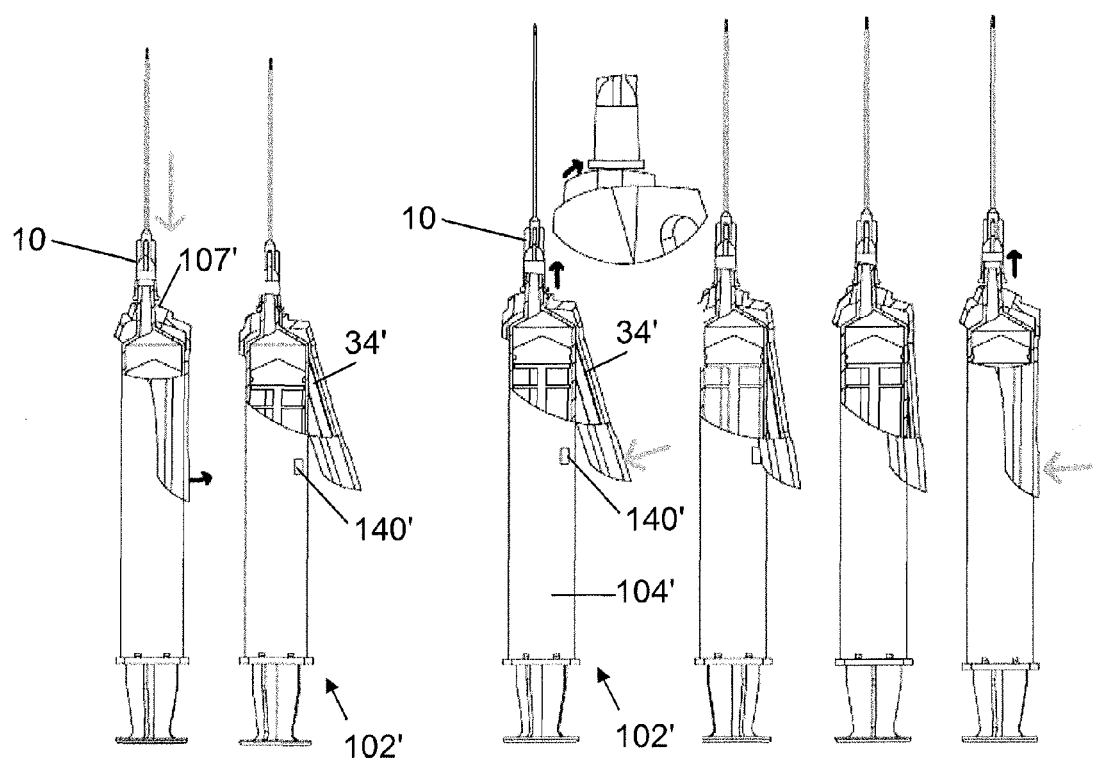
Figure 11d
Figure 11e

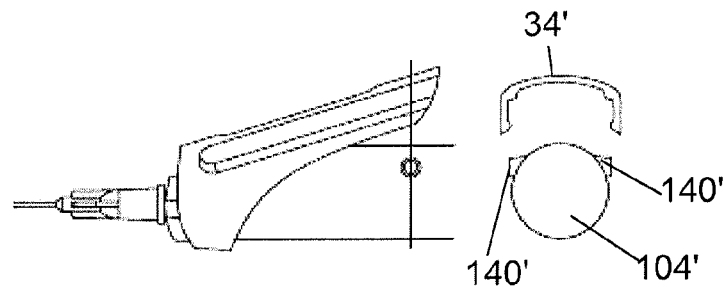
Figure 12a
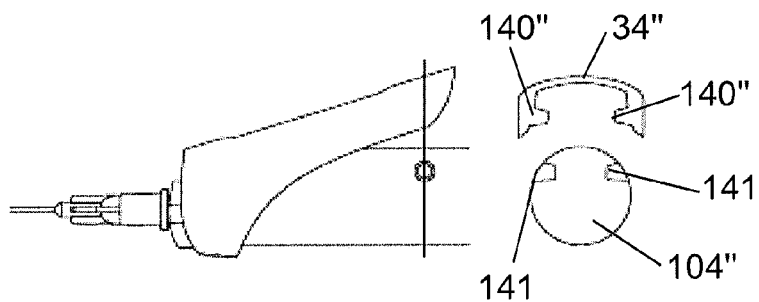
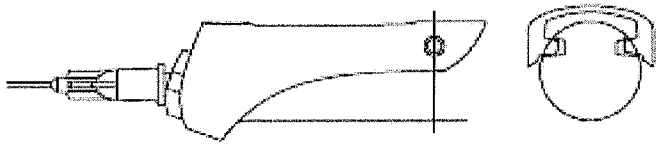
Figure 12b
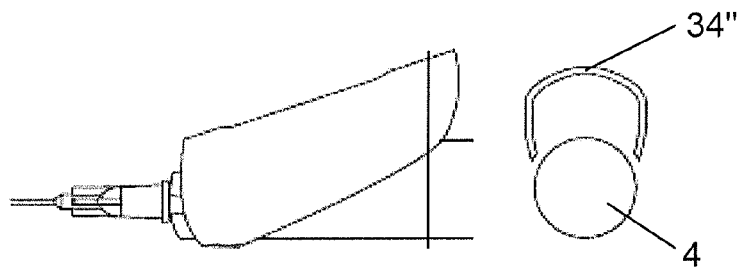
Figure 12c

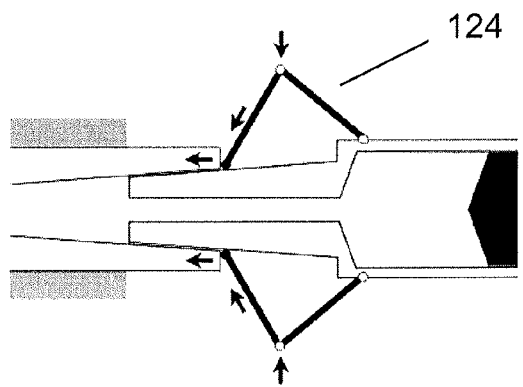
Figure 20a
Figure 20b
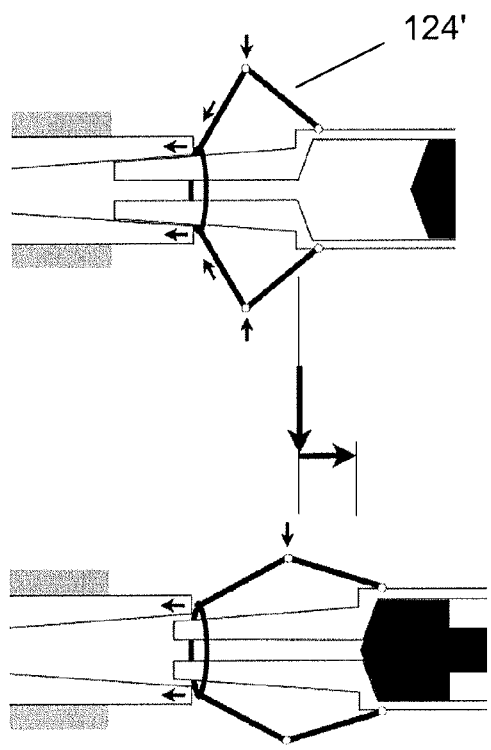
Figure 21a
Figure 21b

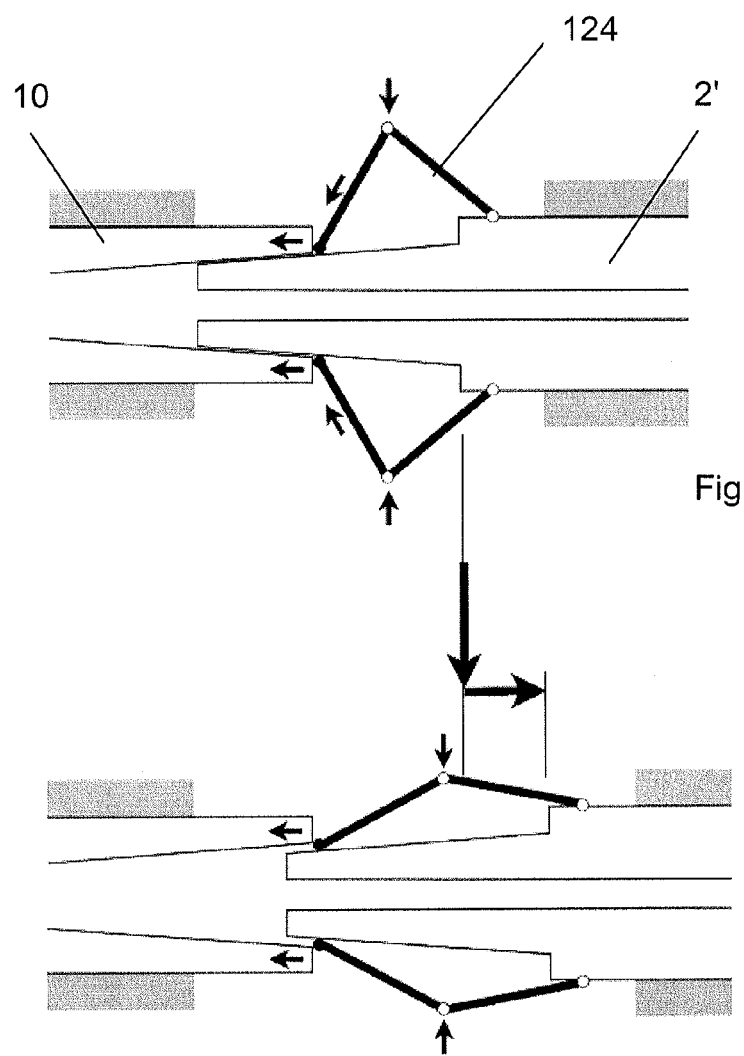
Figure 22a
Figure 22b
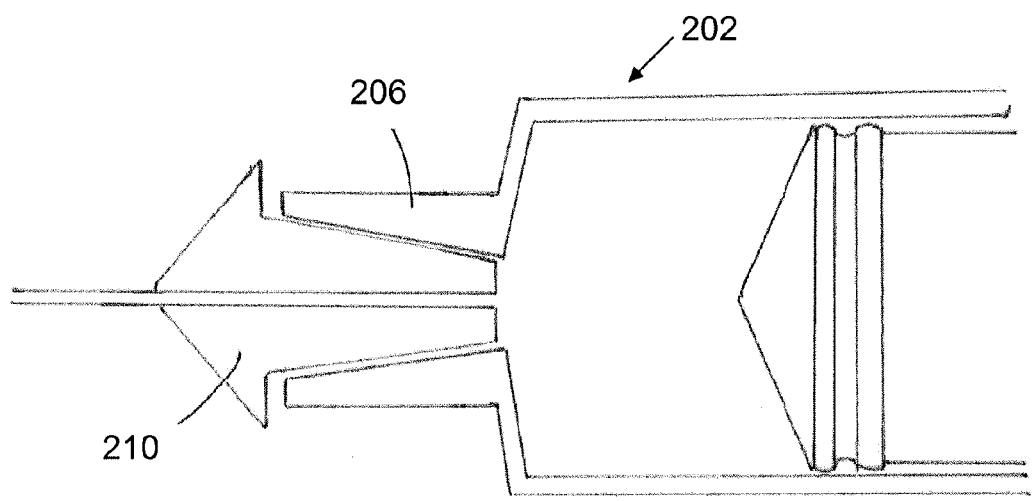
Figure 23

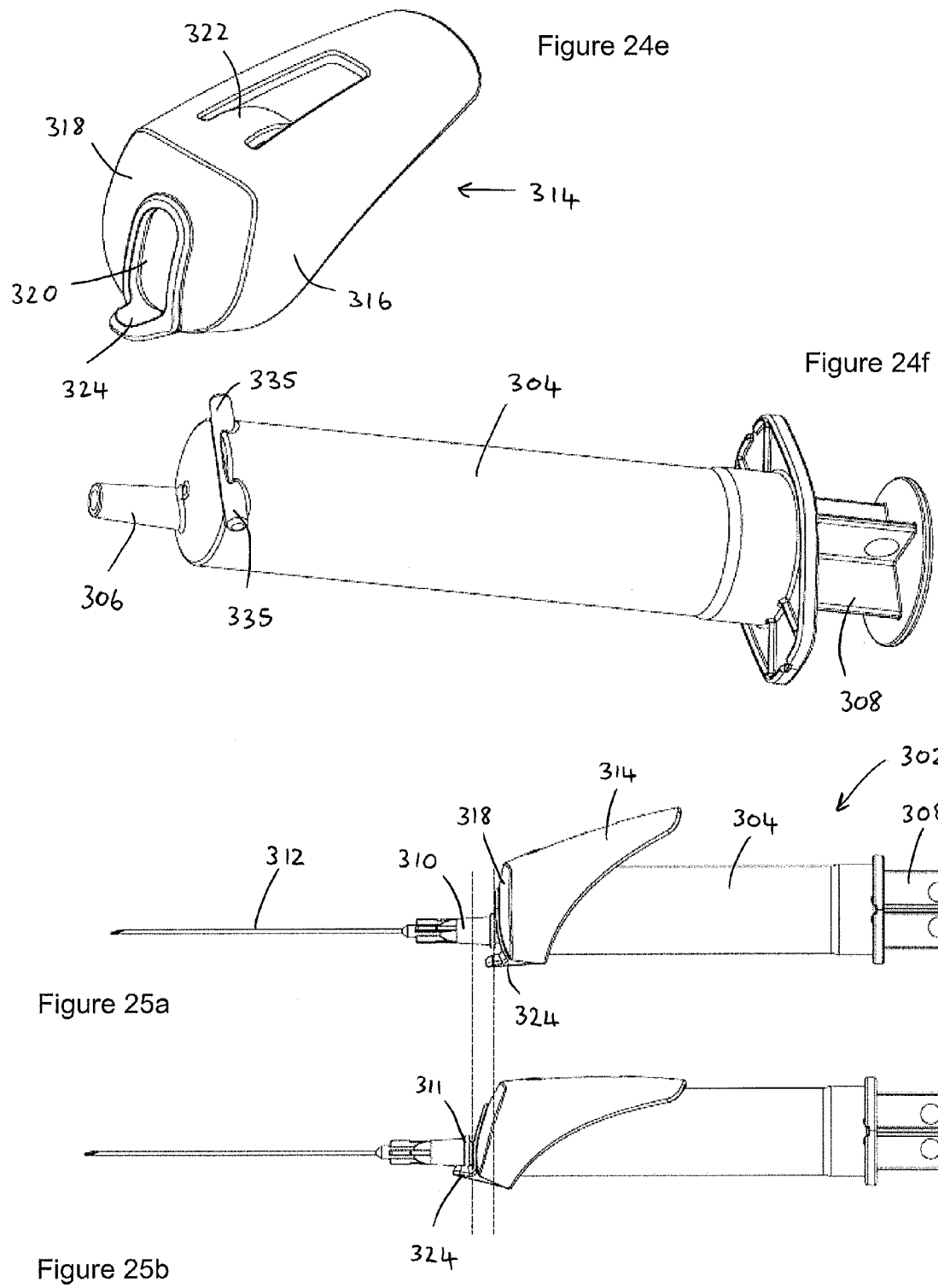

Figure 26a
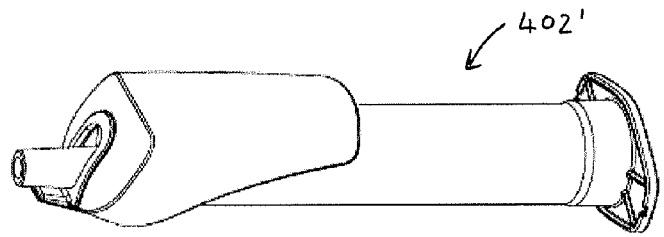
Figure 26b
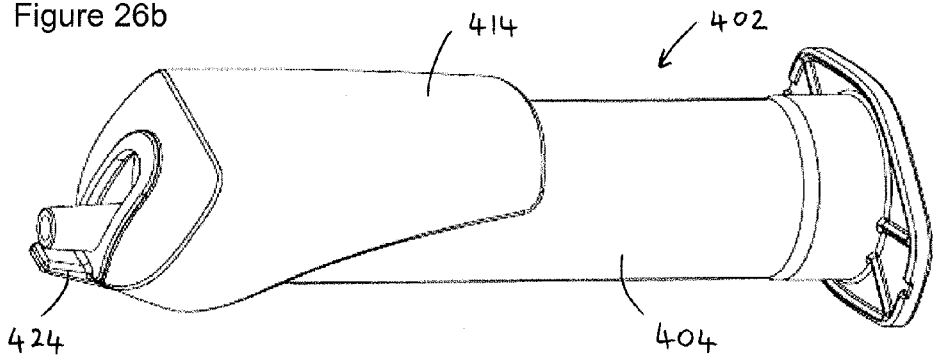
Figure 26c
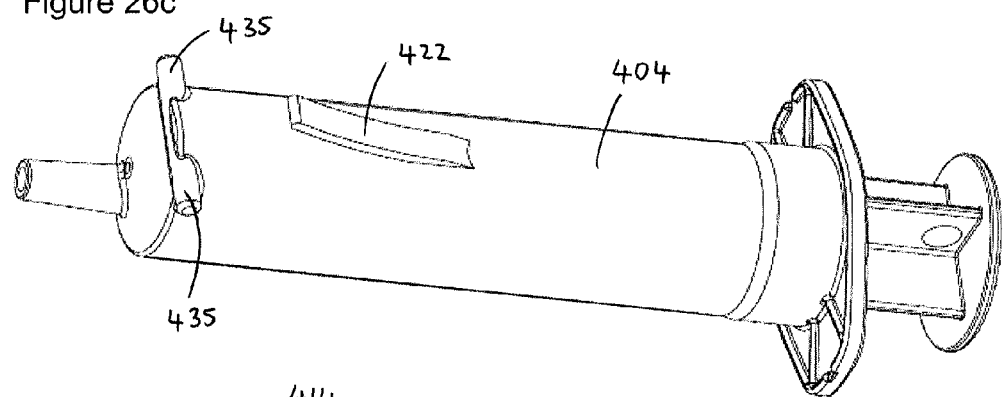
Figure 26d
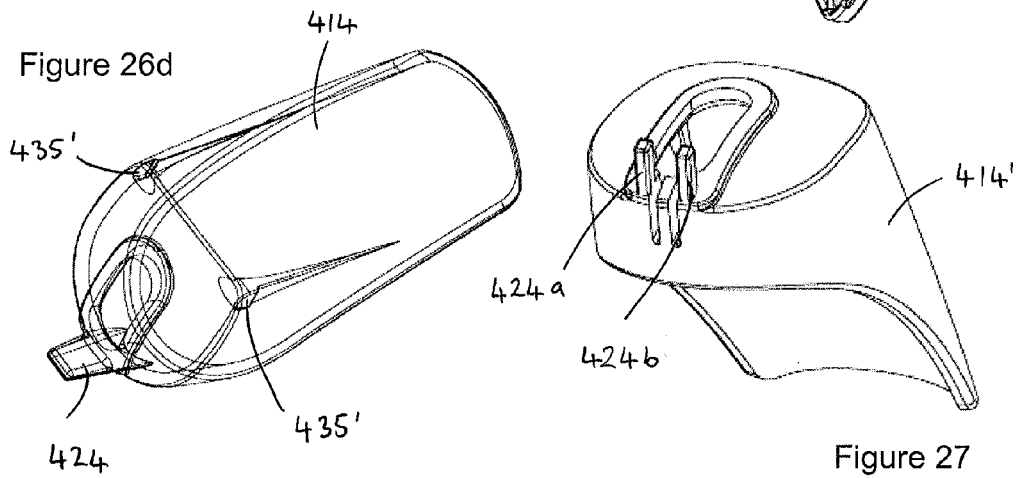
Figure 27

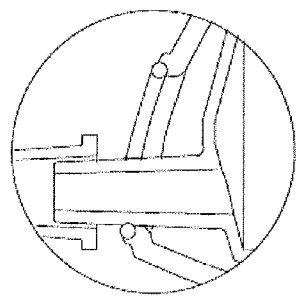
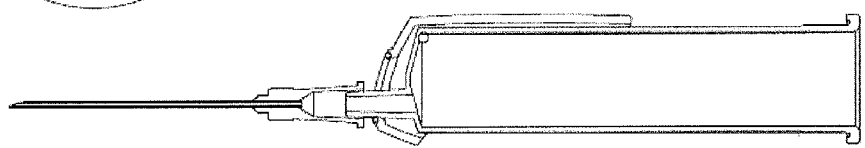
Figure 32c
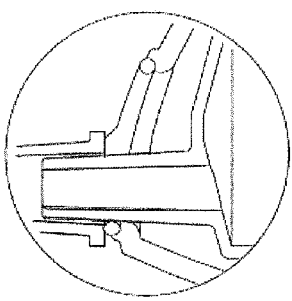
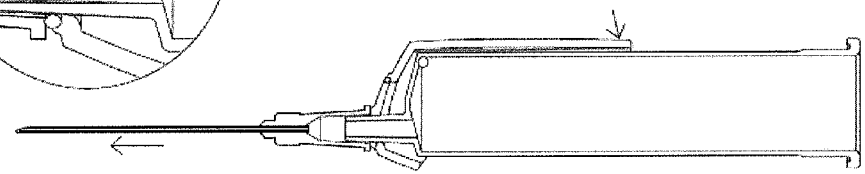
Figure 32b
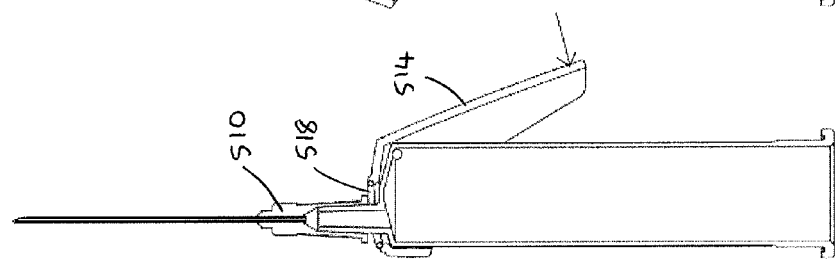
Figure 32a

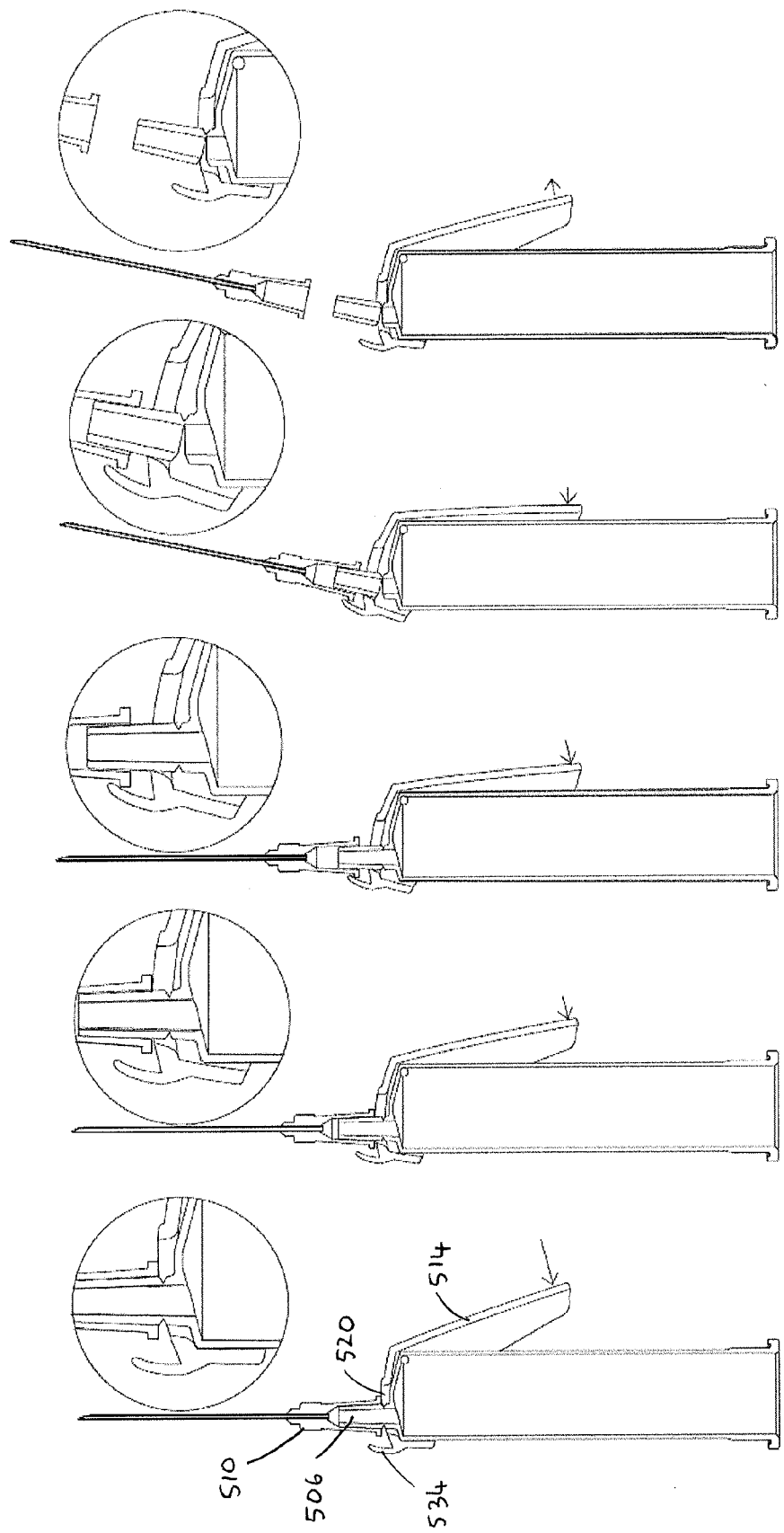

FLUID TRANSFER DEVICES

TECHNICAL FIELD

The present invention relates to the detachment of fluid-transferring devices from a corresponding hub, in particular to the removal of syringes, and especially when transferring fluid in a medical setting. The invention may find particular use in detaching a fluid-transferring device from a hub that is connected to a living subject to/from whom fluid is being transferred.

BACKGROUND OF THE INVENTION

In a medical setting it may be necessary or desirable to transfer fluid to/from a subject for a variety of reasons. For example, a hub connected to a needle or other cannula may be used to draw blood from a vein or to infuse fluid substances i.e. intravenous (IV) therapy. A drip is one type of IV therapy. IV therapy may be used to correct electrolyte imbalances, to deliver medications or nutrition, for blood transfusion or as fluid replacement to correct dehydration. IV therapy can also be used for chemotherapy of cancer patients. Fluid-transferring devices such as syringes may also be attached to a hub that connects a cannula for the addition or removal of fluid to/from a variety of bodily cavities, organs or vessels. For instance, the hub may be part of an entity providing a catheter to drain urine from the bladder or kidney, to remove fluid from an abscess, to extract liquid from joints or cysts, or to administer breathing gases through a tracheal tube. A typical endotracheal tube includes a cuff inflation tube with a hub for attachment of a syringe to enable inflation to seal the trachea and bronchial tree against air leakage and aspiration of fluids. A tracheostomy tube or urinary tract catheter might also use a cuff system with a hub for connection of a syringe or other device to inject fluid to inflate a cup or balloon that holds it in place. However fluid injections using a syringe connected to a needle are one of the most common health care procedures in the world.

When transferring fluids to/from a subject, the hub with its needle, catheter or other cannula inserted in the patient is often left in-situ while the fluid-transferring device may be removed and replaced, e.g. to empty/re-fill a syringe or to change over the IV therapy. Where two medical devices that carry small fluid volumes must be connected, a standard Luer fitting is the most common means of achieving a leak-free junction. One type of Luer fitting, commonly called a "Luer lock/lok", uses an internally threaded collar surrounding a "Luer slip" friction fit (see below) tapered male tip of a syringe or the like. The projecting tip can be inserted into a corresponding female hub with an external thread and the collar screwed down to lock the connection. Such Luer lock fittings have the advantage of providing a secure connection that can not easily come loose, but two hands are needed to hold the hub while screwing the device in/out. A more rapid form of attachment may be preferred in some circumstances, for example in an emergency situation. Another type of Luer fitting, commonly called a "Luer slip", simply uses a friction fit between a female hub and corresponding tapered male tip of a device without a threaded collar. A standard friction fit is achieved by a 6% taper. A Luer slip attachment is common for infusing less viscous fluids, such as vaccinations, and transferring fluids where high pressures are not involved, for example when drawing blood.

A problem observed with both Luer lock and Luer slip connections is the risk of injury when detaching the fluid-transferring device from a hub that is still connected to a patient. While a medical practitioner might take care to hold the hub and avoid injury when unscrewing a Luer lock connection, there is a temptation with a Luer slip connection to try to pull the device from the hub e.g. with one hand. However this can easily result in the hub being tugged away from the body and causing tissue damage. Often the device may not be pulled in a straight line with the cannula connected to the hub, but rotated, and this can twist the components. The tape used to hold the hub e.g. IV port in position is often loosened from the skin and its cannula e.g. needle may even be accidentally extracted. When emptying fluid from a body cavity, for example, keeping the needle hub still when detaching the syringe can be essential to avoid diffuse cutting inside the cavity or damage of the cavity wall. In addition there is a risk of unacknowledged contamination of both the hub and the Luer tip (not only the user) when holding the very small hub with the thumb and index fingers while pulling away the male tip, the tip sliding past the user's fingers as it is released.

Moreover tugging with a single hand does not usually apply enough force even to pull the device out of a friction fitting (such as a Luer slip) and, depending on the force used when connecting the Luer slip tip to the hub, the practitioner usually needs to hold or push the hub while also pulling the device so that it becomes detached. Typically the device will be rotated simultaneously while pulling away from the hub. This jerking can result in unwanted extraction of the needle or other component connected to the hub. The connection will often be pressurised by fluid. For example, a cuff connected to a tracheostomy tube, endotracheal tube or urinary catheter often has a tight connection of the male Luer tip with two-handed operation being required to loosen the connection while the sprung piston in the female Luer hub blocks the outflow of fluid (air or liquid) from the cuff.

Ease of disconnection can be a problem not only when detaching a device from a hub connected to a patient but also when it is desired to fill/empty a device such as a syringe via a fluid hub in a quick and convenient manner. For example, when filling a syringe using a needle inserted in a vial, each time that the syringe is removed it requires two hands to firmly grasp the needle hub and the syringe to separate them while the needle remains in the vial. As mentioned above, there is again a risk of contamination as the user grasps the hub and the tip comes into contact with the fingers holding the hub.

In any situation where one hand is holding a needle hub while pulling a device away there is a risk of needlestick injury and contamination. Needle caps frequently being mislaid or forgotten can exacerbate this. This also applies when separating a needle or other contaminated component from a syringe or similar device for disposal purposes, with many needlestick injuries occurring when trying to remove sharps to throw into a bin. Usually the person handling a syringe will try to cover a contaminated needle with a cap after use, before grasping the hub to separate the needle from the syringe barrel for disposal. However, when mounting a needle cap onto the contaminated needle a person will use the large muscle groups in the arms and shoulders that work less precisely and, combined with poor depth of vision, this often results in a needlestick injury to the fingers holding the needle cap.

SUMMARY OF THE INVENTION

The present invention seeks to address or mitigate the problems outlined above.

According to a first aspect of the present invention there is provided a fluid transfer device comprising a fluid chamber in communication with a male connector tip, the male tip being tapered to form a friction fit when inserted in a corresponding female hub, and further comprising a disconnecting member moveable relative to the male connector tip between a first position proximal to the fluid chamber and a second position spaced from the first position towards a distal end of the male connector tip.

It will be understood that movement of the disconnecting member to the second position interferes with any friction fit of a corresponding female hub onto the male connector tip. If the distal end of the tip is inserted in a corresponding hub then, as the disconnecting member moves along the male tip away from the fluid chamber to the second position, it can act to push against the hub and release the friction fit. A particular advantage is that the device provides its own disconnecting member to effect release. The disconnection can be smooth and controlled as it is the movement of the disconnecting member that releases the device rather than manually pulling or jerking the device away. This can avoid injuries being caused to any subject of a fluid transfer operation when the hub is in situ. Furthermore, because the disconnecting member pushes against the hub it may not be necessary for a user to hold the hub. If a needle is attached to the hub then it may even be disconnected from the device without being covered by a cap. Thus the risk of injury to a user of the device may also be minimised.

The device may find a wide variety of uses, ranging from fluid transfer out of a vial into a syringe chamber, to infusion into an IV port, to extraction of blood from a vein or artery, to injections such as vaccinations, to cuff inflation and to connection of catheters for fluid extraction or administration. Accordingly the fluid chamber may take the form of a syringe barrel, fluid delivery/extraction pipe or hose, etc. The fluid chamber may be rigid or flexible. The fluid being transferred may comprise liquid and/or gas.

So as to maximise the efficacy of the disconnecting member, preferably the male tip is connected to a corresponding female hub exclusively by a friction fit. This means that the tapered male tip is preferably provided without a surrounding threaded collar. It is therefore preferred for the device to comprise a Luer slip tip rather than a Luer lock tip.

Preferably the disconnecting member is manually moveable between the first and second positions. As a user will typically be handling the fluid transfer device, for example operating the plunger of a syringe, then this can make the disconnecting member easy to operate by hand. While a different hand may be used to operate the disconnecting member, preferably the member is positioned on or near the fluid chamber so that a user of the device can move the disconnecting member at the same time as holding the fluid chamber. The manual operation of some different disconnecting mechanisms will be described in more detail below.

The disconnecting member, or at least part of the member operating to disconnect the fluid transfer device, may be moveable between the first and second positions close to the male connector tip. For example, the disconnecting member may be moveable in a space surrounding the male connector tip. So as to ensure that the disconnecting member is effective at releasing the friction fit between the male connector tip and a corresponding female hub, it is preferably arranged to be moved along a surface of the male connector tip between the first and second positions. This can help to maximise the force applied to release the hub from the friction fit.

The Applicant has recognised that the material and/or construction of the disconnecting member can be important for controlling the way that a disconnecting force is applied to a hub connected to the male tip. In particular, it is preferable for the disconnecting member to be relatively stiff so that its movement transmits a disconnecting force effectively. A high force transmission may be required to release a tight friction fit. Ideally the kinetic energy of the disconnecting member is converted efficiently into kinetic energy for the hub that is being released. If the disconnecting member is not stiff then, as it moves relative to the tip against a female hub connected thereto, it may deform and convert its kinetic energy into a store of potential energy instead. There is a risk that the potential energy will build-up before finally being converted into a burst of kinetic energy that results in the hub shooting or popping off the connector tip in an uncontrolled fashion. This is highly undesirable, especially as the female hub may carry a needle, and instead it is preferable for the disconnection to be smooth and controlled. One solution to this problem could be to form the disconnecting member from an inherently stiff material, for example stainless steel.

In order to provide flexibility in the choice of material for the disconnecting member, another solution is to provide the disconnecting member with a stiff construction. This gives freedom for the disconnecting member to be formed from a plastics material, which may be preferred for reasons of disposability, recyclability, sterility, ease of manufacture and cost. The Applicant has devised a novel construction in which the disconnecting member comprises a surface that is substantially transverse to the axis of the male connector tip and one or more other surfaces that extend in a direction substantially parallel to the axis of the male connector tip. Preferably the surfaces form a shroud extending from the male tip towards the fluid chamber. Accordingly it will be understood that the disconnecting member has a three-dimensional construction that is stiffened by the multiple surfaces extending in different directions.

Such a construction is considered novel and inventive in its own right, and thus when viewed from a second aspect the present invention provides a fluid transfer device comprising a fluid chamber in communication with a male connector tip, the male tip being tapered to form a friction fit when inserted in a corresponding female hub, and further comprising a disconnecting member comprising a front surface that is substantially transverse to the axis of the male connector tip and one or more side surfaces that extend in a direction substantially parallel to the axis of the male connector tip, the front surface being moveable along the male connector tip between a first position proximal to the fluid chamber and a second position spaced from the first position towards a distal end of the male connector tip.

Such a disconnecting member is stiffer than a substantially two-dimensional, e.g. planar, member and may therefore be more effective in transmitting kinetic energy. This can be particularly advantageous if it is desired to form the disconnecting member from a plastics material. The construction of the disconnecting member may be further designed for optimal stiffness. Preferably the side surface(s) form a shroud extending back from the front surface towards the fluid chamber. The shroud may at least partially surround the male tip, and preferably also at least partially surround the fluid chamber. The three-dimensional extent of the member can help to ensure that it is stiff even if formed of a plastics material, as is preferred in various embodiments. In a set of embodiments the disconnecting member has a substantially cylindrical form with the side surface(s) extending substantially parallel to the axis of the male connector tip being cylindrical side surfaces. Of course the disconnecting member may be formed so as to have a partially cylindrical form. The side surface(s) do not need to fully surround the axis of the male connector tip. But in at least one set of embodiments the front surface of the disconnecting member is connected to one or more side surfaces that surround the male connector tip, and preferably also at least partially surround the fluid chamber. The surrounding side surfaces may have a cylindrical form or any other suitable shape, for example rectangular. This can stiffen the disconnecting member so that the front surface preferably does not flex when moved against a female hub but instead transmits its kinetic energy to the hub.

Alternatively, or in addition, the front and side surface(s) of the disconnecting member are preferably integrally formed. For example, at least these parts of the disconnecting member may be formed as a single plastics moulding. Alternatively, or in addition, it is preferable that the front surface at least partially surrounds the male tip. The front surface may entirely surround the male tip, for example with the male tip protruding through an aperture in the front surface. This can make the disconnecting member more compact and/or make the front surface more effective in pushing against a female hub mounted on the male tip with a friction fit.

In embodiments where the one or more side surfaces at least partially surround the fluid chamber, for example in the form of a shroud extending back from the front surface, then the disconnecting member can advantageously sit close to the fluid chamber rather than sticking out. This makes the device more compact for the purposes of packaging, transportation, storage, etc. In particular it is preferable for the disconnecting member to comprise a lever member, as will be discussed in more detail below, and then the side surface(s) can provide an input part that is moved towards or away from the fluid chamber so as to pivot the lever member and move the front surface along the male tip. When the side surface(s) generally surround the fluid chamber, such a lever member can be easily operated in one hand by squeezing the input part towards the fluid chamber e.g. in a similar manner to squeezing a trigger. Moreover the stiffness provided by the three-dimensional e.g. shroud-like construction ensures that force applied to the input part is efficiently transmitted as pivotal motion that moves the front surface along the male tip and forces a female hub to be disconnected from its friction fit.

In embodiments of either of the above aspects of the invention, the disconnecting member may comprise at least one disconnecting member, for example one or more members, moving relative to the male connector tip. It will be understood that the following description applies regardless of the number of disconnecting members. The movement of the disconnecting member relative to the male connector tip may take any suitable form. In some embodiments the disconnecting member may rotate around the axis of the male connector tip as it moves along the tip between the first and second positions. For example, the disconnecting member may be rotationally attached to the fluid chamber. However such rotational motion may be less preferred as it could carry a risk of imparting torsional forces on a hub as the tip is pushed away, and with a living subject attached to the hub this could pull or tear the skin or other tissue. To avoid this a user may need to hold the hub still while operating such a disconnection mechanism. As is mentioned above, this means that a hand is close to any needle connected to the hub and the user may therefore be vulnerable to a sharps injury and/or contamination. Or the disconnection operation may cause unwanted and unacknowledged contamination of both the hub and/or the male tip.

In a preferred set of embodiments the disconnecting member, or at least its front surface, is arranged to move substantially linearly (e.g. rather than rotationally) relative to the male connector tip between the first and second positions. This can ensure that the force applied by the disconnecting member against a hub connected to the male tip is substantially in a linear direction, or at least without any twisting around the axis. Linear motion along the surface of the male connector tip may be substantially aligned with the axis of the tip, for example where the taper is relatively small e.g. less than 10% and preferably 6%. The linear motion of the disconnecting member may include an angular component, preferably a component at an azimuthal angle to the axis of the male connector tip. For example, a pivoting motion may result in substantially linear movement without any rotation around the axis of the male connector tip. Of course, while the disconnecting member is arranged to move linearly along the male connector tip it may be operated as part of a mechanism that includes rotating parts. For example, the disconnecting member may pivot and/or rotate relative to the fluid chamber. What is important is that the front of the disconnecting member that contacts any hub connected to the male tip preferably applies a substantially linear force along the axis of the tip to push the device away from the hub. Where the disconnecting member comprises a front surface that is substantially transverse to the axis of the male connector tip, it is this front surface that preferably moves substantially linearly along the axis of the male connector tip.

The fluid transfer device may include means for mounting the disconnecting member. Where the disconnecting member comprises one or more side surfaces that extend in a direction substantially parallel to the axis of the male connector tip, for example in a cylindrical or rectangular form, the side surface(s) can conveniently extend along at least part of the device to engage with the mounting means. Accordingly the fluid transfer device can be conveniently provided with the disconnecting member mounted ready for assistance in disconnecting the male tip from a hub during use. Embodiments of the present invention may therefore provide a new category of fluid transfer devices, such as syringes, that are manufactured and/or sold with a disconnecting member pre-mounted ready for use. While the disconnecting member could potentially be packaged separately and mounted to a device as required, it is advantageous for the device to be packaged and sold as a single unit comprising the disconnecting member mounted thereto.

In one set of embodiments it is preferable that the disconnecting member is removably mounted to the device. This means that a user may remove and discard the member if it is not required or if it is preferable to operate the device without any interference from the disconnecting member. Preferably the disconnecting member is mounted in a bi-stable position such that a force above a certain threshold and/or in a certain direction must be applied to release it from its mounted position. This can prevent the member from being accidentally released from the device.

The disconnecting member may be mounted to the male connector tip, especially if retrofitted to a conventional fluid transfer device (as will be discussed further below). However this may risk the disconnecting member taking up space around the male connector tip that would better used to form the friction fit with a corresponding hub, or otherwise interfere with connection of the device. It is therefore preferred that the disconnecting member is mounted to the fluid chamber. Where the disconnecting member comprises one or more side surfaces that extend in a direction substantially parallel to the axis of the male connector tip, for example in a cylindrical or rectangular form, the side surface(s) may extend parallel to the fluid chamber for mounting purposes. Preferably the side surface(s) form a shroud extending from the male tip to at least partially surround the fluid chamber and engage with mounting means provided by the fluid chamber.

In one set of embodiments the disconnecting member may be slidingly mounted to the fluid chamber with a forward end or front surface moveable relative to the male connector tip between the first and second positions. A sliding member provides linear motion and avoids the risks associated with rotational forces as outlined above. A forward end or front surface of the sliding member that moves along the male connector tip may take the form of a pusher that applies a force against any female hub fitted onto the male tip so as to push away the fluid transfer device. The sliding member may have a strip-like rectangular form, e.g. to run along a side of the fluid chamber, or a sleeve-like cylindrical form, e.g. to surround the fluid chamber. As discussed above, the construction of the sliding member may be chosen to ensure its stiffness even if it is formed of a plastics material.

In one set of embodiments, alternatively or in addition, the disconnecting member may be resiliently mounted to the fluid chamber so as to be biased into the first position. Applying pressure to the disconnecting member against the resilient bias may then move the disconnecting member to the second position. The disconnecting member may take the form of a sleeve mounted coaxially with the fluid chamber, for example slidingly mounted as described above, to ensure linear motion relative to the male connector tip while a resilient means acts against forward movement of the sleeve.

In one set of embodiments, again alternatively or in addition, the disconnecting member may be pivotally mounted to the fluid chamber. The disconnecting member may be arranged to pivot or swing around the axis of the fluid chamber. As the member pivots, one of its surfaces may move along the male connector tip, especially a cam-like surface. However a pivoting or swiveling motion may not be easy to operate manually, especially with one hand, as it may require a hand to hold the device steady while pivoting the member between its first and second positions.

Even when the disconnecting member is arranged to apply a substantially linear force along the male tip, without any twisting about the axis, a user may still need to hold a corresponding hub while the friction fit is being released. A typical Luer slip connection may provide a tight friction fit that is not easily released, especially when the connection has been pressurised by the transfer of fluid. Despite the stiffness of the disconnecting member it may still be difficult to transmit enough force to overcome the friction fit. Two handed operation may therefore be required with the risk of needle injury occurring. In a preferred set of embodiments the disconnecting member comprises a lever member pivotally connected to the device with one end, such as a front surface, moveable between the first and second positions relative to the male connector tip. The disconnecting member may be part of a lever mechanism. In fact the device may not even comprise a fluid chamber as such a lever could interact directly with the male tip that provides fluid transfer, for example if the fluid chamber is removable or if fluid is transferred directly to the tip.

This feature is considered novel and inventive in its own right, and thus when viewed from a third aspect the present invention provides a fluid transfer device comprising a fluid transfer tip, the tip being tapered outwardly from a forward end to an aft end to form a friction fit when inserted in a corresponding female hub, and further comprising a lever mechanism pivotally mounted so as to move relative to the tip between a first position towards the aft end of the tip and a second position spaced from the first position towards the forward end of the tip.

An advantage of using a lever mechanism to disconnect the tip from a corresponding hub is that it can amplify an input force to provide a greater output force, i.e. providing leverage to push the tip away from a hub. The mechanical advantage of a lever mechanism can increase the force applied so that the device can be released without necessarily holding the hub, thereby enabling single-handed operation. A lever mechanism therefore represents a particularly preferred configuration for the disconnecting member(s). As before, it is preferable that the lever mechanism is manually moveable between the first and second positions.

Single-handed disconnection of a fluid transfer device can be particularly helpful during surgical procedures, when a nurse or anaesthesiologist may e.g. exchange different syringes of medication, with 5, 10, 20 or more different connections taking place at an IV port. At the same time, such medical personnel are busy checking vital signs and monitors and it is preferable not to have the distraction of using two hands to disconnect an IV line or similar. However a lever mechanism may be operated with one hand e.g. thumb/index finger in a smooth workflow from connecting a syringe to an IV hub, injecting, and removing the syringe. The technique can be repeated using the same hand and the lever mechanism operated whether the user is right- or left-handed.

Single-handed operation also facilitates disconnection of devices from needles in a safe and rapid manner. For example, when performing a "blood gas" test a clinician must palpate into an artery in the wrist or groin to perforate the artery with a needle connected to a syringe and extract the arterial blood. As the arterial blood vessel is under high pressure (e.g. as compared to a vein), to prevent excessive bleeding from the artery wall it is necessary to compress hard on the artery for a while immediately after removing the needle. At the same time, it is desirable to be able to disconnect the needle and send the syringe to the lab for analysis. Using a lever mechanism, one hand can compress the artery while the other hand safely disconnects the needle to drop into a sharps bin. The risk of needle injury may thereby be reduced or avoided entirely.

When drawing medication from vials using a syringe, single-handed disconnection from the needle hub allows for the other hand to simultaneously hold the container into which the medication will be injected. This is very practical in terms of workflow, as well as being an important step to reduce or avoid entirely any contamination of the hub and/or the male tip of the syringe.

In order to take advantage of the force amplification provided by a lever mechanism, it is preferable that the member(s) of the lever mechanism that transmit force to disconnect the tip from a corresponding hub are relatively stiff. As discussed above, the lever mechanism may comprise a lever member with a front surface that is substantially transverse to the axis of the tip and one or more side surfaces that extend in a direction substantially parallel to the axis of the tip, the front surface being moveable along the tip between the first position and the second position.

In embodiments of the third aspect of the invention, the fluid transfer tip may be connected, either removably or integrally, to a fluid chamber. For example, the fluid transfer tip may be connected to the barrel of a syringe. The force to be applied by the lever mechanism is largely independent of any upstream fluid chamber but depends rather on the tightness of the friction fit to a hub, which may be influenced by the fluid pressure in the tip as well as being determined by the force applied by the user when connecting the fluid transfer tip e.g. male tip to the hub to form the friction fit. Of course the fluid being transferred may comprise liquid and/or gas. Each of the following features may be applied equally to any of the foregoing aspects of the invention.

As already mentioned, preferably the lever mechanism comprises one or more lever members pivotally mounted to the device. The lever mechanism may comprise a member pivotally mounted to the fluid transfer tip, but preferably the member(s) is/are pivotally mounted to the fluid chamber (where one is provided by the device). Where the disconnecting member comprises one or more side surfaces that extend in a direction substantially parallel to the axis of the male connector tip, for example in a cylindrical or rectangular form, the side surface(s) may conveniently provide for pivotal mounting to the fluid chamber. This can be assisted by the side surface(s) forming a shroud extending from the male tip to at least partially surround the fluid chamber and engage with mounting means provided by the fluid chamber.

The lever member(s) (or at least an input part thereof) may be pivotally mounted so as to lift away from the device while moving from the first position to the second position. However, in a preferred set of embodiments the lever member(s) (or at least an input part thereof) is pivotally mounted so as to approach the device as it moves from the first position to the second position. This can make it easier for a user to squeeze the lever mechanism, or a least its input part, like a trigger when disconnecting the device from a hub. It can be easier to push down on a lever member than to pull up a lever member, especially if the lever member is mounted against a side of the device. Single-handed operation may therefore be facilitated, especially when the device takes the form of a syringe. The lever mechanism may comprise multiple lever members, for example a linkage of pivoting members. A linkage mechanism may be designed to maximise the mechanical advantage while minimising the range of movement of the mechanism. A linkage mechanism may therefore be ideally suited to small scale fluid transfer devices, such as the small volume e.g. 1 ml syringes commonly used to inject vaccinations.

Whether part of a linkage mechanism or otherwise, each lever member(s) of the mechanism preferably comprises an output part, forward of its pivot point, arranged to move along the tip between the first and second positions. The output part may comprise the front surface of a three-dimensional member such as is described above. As the output part is moving along a tapered tip, for example at an angle of 6% from the axis of the tip, and especially if it is moving along a surface of the tapered tip, it will apply a force that is not exactly aligned with the axis of the tip and this can result in at least a small turning moment being applied to a hub that is connected to the tapered tip.

The lever mechanism may comprise two or more lever members pivotally mounted to act on the hub in a symmetrical manner. Such symmetrical arrangements can ensure that there is no overall turning force on the hub as a resulting of the pivoting motion of the disconnecting members. Furthermore the Applicant has appreciated that any arrangement of lever members, whether multiple members or a single lever member, that achieves an overall movement substantially in line with the axis of the tip is advantageous for pushing away a corresponding hub without applying a turning moment. It is therefore preferable for the lever mechanism to comprise one or more members arranged such that pivotal movement of the member(s) results in an overall movement between the first and second positions that is substantially in a direction aligned with the axis of the tapered tip.

This feature is considered novel and inventive in its own right, and thus when viewed from a fourth aspect the present invention provides a fluid transfer device comprising a fluid transfer tip, the tip being tapered outwardly from a forward end to an aft end to form a friction fit when inserted in a corresponding female hub, and further comprising a lever mechanism pivotally mounted so as to move relative to the tip between a first position towards the aft end of the tip and a second position spaced from the first position towards the forward end of the tip, wherein the lever mechanism comprises one or more members arranged such that pivotal movement of the member(s) results in an overall movement between the first and second positions that is substantially in a direction aligned with the axis of the tip.

The member(s) of the lever mechanism may be arranged in any way suitable for achieving an overall linear movement and hence a substantially linear force acting to push away a hub and release its friction fit. As is mentioned above, in one set of embodiments such a linear movement may be achieved by the lever mechanism comprising two or more lever members pivotally mounted to act on the hub in a symmetrical manner relative to the axis of the tapered tip. For example, one or more pairs of lever members may be arranged such that the members of each pair pivot in opposite directions so that any turning moments are cancelled out and the overall force applied by the mechanism is a linear one. However other embodiments are also envisaged, including embodiments with a single lever member that can pivot in a way which keeps its movement aligned with the tip, as will be described below.

Whenever a lever member is pivotally mounted there is a risk of the member imparting a turning force on a hub even as its output part e.g. front surface moves along a surface of the tip or in a direction along the axis of the tip. If the surface is rotating at the same time as moving forward then the movement will have a component that is not linear. This can be a particular problem for a lever mechanism comprising one or more members mounted with a fixed pivot axis. Even if lever members are paired to move symmetrically, the mechanism must be carefully designed to ensure that the input force is shared evenly between the lever members in each pair so that they move equally and result in an overall movement that is in a direction aligned with the axis of the tip. In at least some embodiments it is preferable for the mechanism to comprise one or more lever members that are pivotally mounted with a moveable axis. When the pivot axis is moveable, a lever member can be arranged so that the overall movement of its output part (e.g. front surface) is substantially always in a direction aligned with the axis of the tip. For example, in a set of embodiments the lever mechanism, or a lever member thereof, is pivotally mounted such that a front surface moves between the first and second positions while remaining substantially tangential to the axis of the tip.

This feature is considered novel and inventive in its own right, and thus when viewed from a further aspect the present invention provides a fluid transfer device comprising a fluid transfer tip, the tip being tapered outwardly from a forward end to an aft end to form a friction fit when inserted in a corresponding female hub, and further comprising a lever member comprising a surface moveable relative to the tip between a first position towards the aft end of the tip and a second position spaced from the first position towards the forward end of the tip, wherein the lever member is pivotally mounted with a moveable axis.

As is discussed above, a moveable pivot axis can allow for a front surface of the lever member to move between the first and second positions while remaining substantially tangential to the axis of the tip. Furthermore, the Applicant has recognised that a lever member can be made more flexible and tactile in its operation by being pivotally mounted with a moveable axis. When a lever member is pivotally mounted with a fixed axis there is a risk of it reacting to any accidental touch and acting to prematurely disconnect the tip from a corresponding hub. When a force is applied to a lever member with a moveable axis, on the other hand, it can adapt and shift its pivot axis before the input force is transmitted to an output part of the member. The lever member can therefore provide a "soft" response and settle into a pivoting position appropriate to whether it is being pushed towards or away from the device. Flexibility of use is therefore improved. Whereas, in a lever mechanism with a fixed pivot axis, the position of the fixed axis sets the way that the lever operates, so that its operational movement is always either towards or away from the device.

The moveable axis may be free to move in response to user input. However in preferred embodiments the movement of the pivot axis is confined to an engagement zone between the lever member and the device. When the moveable axis is provided by an engagement zone, the axis of rotation may have dynamic freedom but within the confines of the zone. The engagement zone may be provided by the device or by the lever member or by both. In a set of embodiments the lever member is pivotally mounted by a zone on the lever member that engages with fixed pivot point(s) on the device, or vice versa. The pivot axis is defined by the pivot point(s) but it is not fixed as the pivot point(s) may move within the engagement zone. In another set of embodiments the lever member is pivotally mounted by a zone of the lever member that engages with a zone on the device. The respective engagement zones may each be surfaces that are formed to engage with one another. As the surfaces of the engagement zones move relative to one another during pivoting of the lever member, the shape and form of the respective surfaces can dictate the range of movement that is possible. The pivot axis may therefore be movable within certain confines set by the interaction of the engagement zones. For example, a surface zone of the lever member may engage with a surface zone of the device, for example a surface of a fluid chamber such as a syringe barrel.

Some further features of a lever mechanism will now be described, which may be provided in addition to (or instead of) a centric movement and/or a moveable pivot axis.

In one set of embodiments the lever mechanism may comprise one or more generally L-shaped members that are pivotally mounted to the device, for example to a barrel of the syringe or other fluid transfer device. The (or each) lever member preferably comprises an input part, aft of its pivot point, and an output part, forward of its pivot point. An advantage of an L-shaped lever member is that its input part may be arranged adjacent to a fluid chamber of the device for ease of manual operation. The pivot point of the lever member may be arranged at or near the aft end of the tip. Such an L-shaped lever member may have a substantially cylindrical or rectangular form of the kind described above. In particular, the L-shaped lever member may comprise a front surface that is substantially transverse to the axis of the tip and one or more side surfaces that extend in a direction substantially parallel to the axis of the tip, for example forming an L-shaped shroud extending from the tip towards the fluid chamber. Such an L-shaped member may take the form of a shroud that at least partially surrounds the fluid chamber. As is mentioned above, this means that the lever member can be conveniently positioned so as to be easily gripped by a user, for example by a single hand that squeezes the L-shaped barrel against the fluid chamber. Furthermore the lever member may be operated at a safe distance from the tip that may be connected to a hub carrying a needle or other sharp instrument.

In other embodiments the lever mechanism may comprise one or more pivotally mounted members comprising an output part forward of a pivot point. The output part may simply be moved by direct force rather than using an input part to provide a turning force about the pivot. For example, the output part(s) may be pressed or squeezed so as to pivot and provide an overall linear movement along the tip. Such lever mechanisms may be more compact and could be better suited to small scale devices as mentioned above. Furthermore the size of the lever mechanism could impact on the amount of packaging required (especially for sterile medical devices) and packing density of devices for storage and distribution. While safety for users is paramount, the costs involved in delivering medical devices are always a concern, in particular with respect to developing countries.

As the lever member(s) of the mechanism pivot e.g. under manual force, preferably the output part is arranged to move substantially linearly along the tip between the first and second positions. Due to the small e.g. 6% taper, such movement along the surface of the tip will not be exactly aligned with the axis of the tip but substantially so. The output part preferably provides a surface, e.g. a front surface, to push against any hub that is connected to the tip. The surface of the output part may be planar. A planar surface will provide a constant pushing force as the lever is pivoted to move the output part along the tip. However the applicants have realised that it may be desirable for the output part to apply a variable force. In at least some embodiments the surface is preferably curved, such that the curved surface can be tailored to provide a desired variation in force during operation of the lever member. In particular, the surface of the output part is preferably elliptical in shape so as to provide an increasing or decreasing force during movement of the lever member.

For a lever member pivotally mounted such that the output part moves in a direction x along the axis of the tip (or substantially along the axis of the tip, for example along a tapered surface of the tip), the surface of the output part preferably has a curved profile in the xy or xz plane, i.e. so as to apply a force component in a direction tangential to its direction of movement. Such a force component may be considered azimuthal, rather than rotational, relative to the axis of the tip. So as to avoid an overall torsional force acting on the hub, two or more lever members having a curved output surface may be arranged to act symmetrically about the axis of the tip e.g. pivoting across from opposite points. Further preferably the curved surface of the output part has an increased curvature relative to the axis of the tip as the lever member moves from the first to second positions. As the curvature increases and the surface is acting less tangentially to the axis of the tip, the force applied by the output part decreases. By arranging for the applied force to be highest when the lever first moves from its first position but to decrease as it moves towards the second position, any hub connected to the tip will be pushed away but under a deceleration so that the device does not violently or forcefully disconnect. This can provide a particularly advantageous mechanism to smoothly and precisely disconnect a fluid transfer device. An additional, or alternative, solution to the problem of a female hub potentially being forcefully disconnected and shooting away from the device is described below.

The member(s) of the lever mechanism may be pivotally mounted so as to be resiliently biased into the first position. This can ensure that the lever mechanism, or at least its output part, is normally clear of the distal end of the fluid transfer tip so that it can be connected to a corresponding female hub without interference. Manual operation of the lever mechanism can then overcome the bias force to move it from the first position to the second position when it is desired to push away the hub and disconnect the device.

In at least one set of embodiments, the lever mechanism is preferably mounted so as to freely pivot between the first and second positions. This removes the need for a user to overcome a bias force and can maximise the force output of the mechanism. Furthermore, when the lever mechanism is free to pivot it means that connection of the fluid transfer tip to a corresponding hub can automatically push the lever mechanism (or at least its output part) towards the first position so that it becomes "charged" ready for use without a resilient means being required. The same principle may apply in more general terms, and thus it is preferable for any disconnecting member to be mounted to the device so as to be freely moveable, irrespective of its form of movement. This may also provide a user with manual dexterity in controlling movement of the member and disconnection of the device.

A further benefit of the disconnecting member being freely mounted to the device is that its movement can be used to give visual and/or tactile feedback to a user when connecting a female hub to the tip. When a female hub is pushed onto the tip, e.g. towards the fluid chamber where one is provided, a freely mounted disconnecting member will be automatically moved back into the first position, e.g. towards the aft end of the tip. This degree of movement may be related to the tightness of the friction fit. If a user can see and/or feel the disconnecting member being moved between the second and first positions then the user is provided with an indication of whether the hub has been properly connected to the tip. In at least some embodiments this can ensure that a tight connection is formed without necessarily requiring any additional connection means, such as a screw connection. Such a feature therefore provides a particularly simple solution to the problem of poor connection to the fluid transfer device.

In embodiments where the disconnecting member comprises a lever member pivotally mounted to the device, preferably a lever member comprising a front surface that is substantially transverse to the axis of the tip and one or more side surfaces that extend in a direction substantially parallel to the axis of the tip, then it is further preferred that the lever member is pivotally mounted such that the front surface moves from the first position to the second position when the side surface(s) are pivoted towards the fluid chamber, e.g. squeezing the side surface(s) against the fluid chamber causes the front surface of the lever member to push away a hub connected to the tip. In one set of embodiments the lever member may be pivotally mounted so as to be resiliently biased into the first position, as is mentioned above. A user may therefore need to squeeze the side surface(s) towards the fluid chamber against a resilient bias. In another set of embodiments the lever member is mounted (e.g. to the fluid chamber) so as to pivot freely. Before connection to a hub and/or after disconnection from a hub, the lever member can be freely pivoted so that the side surface(s) are engaged against the fluid chamber when it is desired to make the device compact e.g. for storage. Preferably the lever member is pivotally mounted such that when the front surface is moved to the first position (proximal to the fluid chamber), e.g. by connecting a female hub to the male tip, the side surface(s) pivot away from the fluid chamber. The lever member is therefore automatically "charged" ready for use e.g. when it is desired to disconnect the device after a medical procedure such as a blood draw is complete. This can also provide a visible indication that the hub has been properly connected with the pivoting of the lever member indicating that a tight friction fit has been achieved. A user may also receive tactile and/or audible feedback from the pivotal motion of the lever member. For example, in one set of embodiments the lever member is arranged to give an audible "click" when the side surface(s) pivot away from the fluid chamber.

Another set of embodiments that may be provided in addition, or alternatively, will now be described. The member(s) of the lever mechanism may be pivotally mounted in a fixed manner, for example fitted to one or more pivot points or shafts. The lever mechanism may be snap-fitted onto such pivot points or shafts. This can ensure that the lever mechanism is securely attached to the device e.g. cannot easily be removed. A fixed mounting may encompass both a fixed pivot axis and moveable pivot axis. In the latter case, the engagement between the pivot point(s) and an engagement zone (or between two engagement zones) may be a permanent one albeit allowing for movement within the zone. However, as mentioned above, in a set of embodiments it is preferable that the lever mechanism is pivotally mounted in a removable manner. For example, the lever mechanism (or at least some of its members) may be removably mounted to one or more pivot points or shafts. An advantage of such embodiments is that a user can remove the lever mechanism as desired, e.g. if it is not required or found to interfere with other operation of the device. The device can therefore adapt to a range of clinical (and other) uses and environments.

Another set of embodiments that may be provided in addition, or alternatively, will now be described. It may be desirable to be able to selectively control when movement of the lever mechanism or disconnecting member can take place. For example, it may be desirable for a disconnecting mechanism to be disabled while the tip is connected to a hub during supply or transportation of a device. In particular, hypodermic syringes for injections such as vaccinations are often supplied with a needle hub already connected to the tip of the syringe. It is preferable for the device to comprise means for locking the lever mechanism or disconnecting member in the first position or in the second position. Such locking means may hold the disconnecting member in either the first or second position relative to the tip. In embodiments where the disconnecting member comprises a lever member pivotally mounted to the device, preferably a lever member comprising a front surface that is substantially transverse to the axis of the tip and one or more side surfaces that extend in a direction substantially parallel to the axis of the tip, then it is further preferred for the locking means to lock the lever member in the second position with the side surface(s) pivoted towards the fluid chamber. The device may therefore be locked in a compact configuration e.g. for storage, transport, etc.

In embodiments where a locking means is arranged to hold the disconnecting member in the second position, then connecting a hub to the tip may act to overcome the locking means and move the member back to the first position. This may be in combination with a visual and/or tactile feedback as described above that ensures the hub is connected with a sufficiently tight friction fit. For example, release of the locking means could be accompanied by an audible click that indicates the hub has been pushed far enough along the tip to achieve a tight friction fit and release the locking means. In embodiments where the disconnecting member comprises a lever member pivotally mounted to the device, preferably a lever member comprising a front surface that is substantially transverse to the axis of the tip and one or more side surfaces that extend in a direction substantially parallel to the axis of the tip, then it is further preferred that the locking means is arranged to be overcome when the front surface is moved to the first position, e.g. by connecting a female hub to the male tip, so that the side surface(s) pivot away from the fluid chamber. The lever member is then automatically "charged" as described above. Means for locking the disconnecting member in the second position may also be used to prevent the device from being re-used after disconnection from a hub, i.e. a single use device.

Such locking means may take the form of a moveable blocking member. The blocking member could be a wedge held by friction or a stop that is hinged or frangible. In one preferred set of embodiments the blocking member may be provided by a needle cap. This means that the device can be provided with a needle hub connected to the tip and the lever mechanism/disconnecting member blocked from moving out of the first position as long as the cap is attached to the needle. Removing the cap from the needle can unblock the disconnecting mechanism so that it is available to release the device from the needle hub after use. Thus in one set of embodiments the tip may be connected to a corresponding female hub comprising a hypodermic needle and a needle cap provided with a blocking member for the disconnecting member or lever mechanism.

An aspect of the invention also extends to a needle hub comprising a tapered friction fitting for a corresponding male connector tip, the needle hub comprising a hypodermic needle and a needle cap, wherein the needle cap comprises blocking means projecting along the male connector tip in use. As long as the cap is fitted on the needle, the blocking means can prevent any disconnecting mechanism from moving along the tip and pushing against the hub. The disconnecting mechanism is therefore disabled by the presence of the needle cap.

As is mentioned above, a means for mounting the lever mechanism or disconnecting member may be integrally provided by the device. In some embodiments the lever mechanism or disconnecting member may be moveably mounted to a fluid chamber, for example to mounting means integrated with the fluid chamber. The fluid chamber, such as the barrel of a syringe, may be designed to mount a disconnecting member so that the device can be supplied with the disconnecting member ready for use. However, in some other embodiments it may be desirable to retrofit a lever mechanism or disconnecting member to an existing fluid transfer device. For example, it may be desirable to mount a lever mechanism or disconnecting member to a standard syringe or other device so as to enjoy various of the benefits outlined above but without changing the device design. The disconnecting member, alone or as part of a disconnecting mechanism or lever mechanism, may be attached to a fluid transfer device by any suitable means. So as to avoid interference with the male connector tip, a disconnecting member may be attached to the aft end of the tip by an attachment collar.

Such a retrofitting mechanism may be considered novel and inventive in its own right. When viewed from a further aspect the present invention provides a disconnecting mechanism for a fluid transfer device that comprises a fluid transfer tip tapered outwardly from a forward end to an aft end to form a friction fit when inserted in a corresponding female hub, the mechanism comprising an attachment collar to attach the mechanism to the aft end of a tip and a disconnecting member moveable relative to the collar to a second position spaced away from the collar and towards the forward end of the tip.

It will be understood that such a mechanism may be attached around the tapered tip of a fluid transfer device, such as a syringe, in any situation where operation of the disconnecting member may assist in disconnecting the tip from a corresponding hub. The mechanism may be attached before or after inserting the tip into a hub. Such a mechanism could be optionally attached to a fluid transfer device by a user when it is determined that the friction fit is too tight to be easily disconnected by pulling the device, or at least not without risking damage or injury. The mechanism could also be optionally attached where the device is connected to a hub carrying a needle and protection from needle spike is desired. The disconnecting mechanism may have any of the features described above with respect to a disconnecting member or a lever mechanism. Thus in embodiments according to this aspect of the invention the disconnecting mechanism may comprise a lever member pivotally mounted to the attachment collar. Other of the preferred features outlined above may equally be applied to such a retrofitting mechanism.

Another set of embodiments that may be provided in addition, or alternatively, will now be described. It is mentioned above that when a disconnecting member is moved from the first position to the second position so as to release a friction fit between the tip and a hub connected thereto, there may be a risk of the hub shooting away from the tip. This could be especially dangerous where the hub carries a needle or other sharp instrument. This problem may be accentuated when a lever member is used to disconnect the friction fit, as the force amplification of the lever member could push the hub away more violently than would be desirable. It is therefore preferable for the device to further comprise a catch means arranged to catch the female hub after it has been disconnected from a friction fit with the male connector tip by the disconnecting member moving to the second position. In embodiments where the disconnecting member comprises one or more lever members, a catch means is preferably arranged to catch the female hub after it has been released from the friction fit by the lever member(s) pivoting to move the front surface towards the second position. Such a catch may advantageously be employed regardless of the nature of the disconnecting member.

This is considered novel and inventive in its own right, and thus when viewed from a further aspect the present invention provides a fluid transfer device comprising: a fluid chamber in communication with a male connector tip, the male tip being tapered to form a friction fit when inserted in a corresponding female hub; a disconnecting member moveable relative to the male connector tip between a first position proximal to the fluid chamber and a second position spaced from the first position towards a distal end of the male connector tip so as to release the friction fit; and a catch means arranged to catch the female hub after it has been released from the friction fit by the disconnecting member moving towards the second position. The invention further extends to a fluid transfer device connected to a female hub, the device comprising: a fluid chamber in communication with a tapered male connector tip that is inserted into the female hub to form a friction fit; a disconnecting member moveable relative to the male connector tip between a first position proximal to the fluid chamber and a second position spaced from the first position towards a distal end of the male connector tip so as to release the friction fit; and a catch means arranged to catch the female hub after it has been released from the friction fit by the disconnecting member moving towards the second position. In a set of embodiments the female hub comprises a cannula or hypodermic needle and the fluid transfer device comprises a syringe. However various other devices may benefit from the invention, as is outlined below.

It will be appreciated that such devices can take advantage of a conventional friction fit, in particular a standard "Luer slip" connection, for the tip and preferably without any additional connection means such as a screw connection. The catch means is not arranged to lock the connection between the tip and a corresponding hub, but merely to catch the hub after it has been loosened from the friction fit so that the hub can not shoot away from the tip. Of course, the catch means may not necessarily act to catch the hub after it has been entirely released from its friction fit with the tip. Rather the catch means may be arranged to catch the female hub after it has been at least partially disconnected, e.g. once the connection has been loosened by the disconnecting member to such a degree that the hub may otherwise come away from the tip.

The catch means may be provided in any suitable way by the device. The catch means is preferably arranged relative to the male connector tip so as to catch a female hub as it is moved towards a distal end of the male connector tip by the disconnecting member moving towards the second position. Preferably the catch means is arranged to operate automatically, i.e. without user actuation. The catch means may comprise any member that engages against the hub to hold it back e.g. using mechanical interlocking, friction, adhesion, etc. For example, the catch means may comprise at least one grabbing member e.g. finger(s) extending towards the distal end of the male connector tip. In other examples, the catch means may comprise at least one gripping pad or adhesive surface e.g. arranged to catch the female hub after it has been pushed away from the fluid chamber by the disconnecting member moving to the second position. The catch means may simply engage against a surface of the hub, for example where the hub is an IV port and a syringe of saline solution is connected to the hub. Where the hub is provided with a rim, for example a needle hub, then this can aid the catch mechanism.

In one set of embodiments the catch means may be independent of the disconnecting member, for example provided by the fluid chamber and/or male connector tip. However it is desirable that the catch means does not interfere with movement of the disconnecting member. In another set of embodiments the catch means is preferably provided by the disconnecting member. This may make it easier to ensure that the catch means only operates once the disconnecting member is moving or has moved to the second position to release the friction fit. For example, the catch means may comprise at least one grabbing member e.g. finger(s) extending from the disconnecting member towards the distal end of the male connector tip.

It may be particularly convenient for the catch means to be provided by the disconnecting member when the disconnecting member comprises one or more lever members, as the pivotal motion of the lever member(s) can help to bring the catch into engagement with the hub only once the friction fit has been loosened. Thus in a preferred set of embodiments the disconnecting member comprises a lever member pivotally mounted to the device and the catch means is provided by the lever member, e.g. integrated with the lever member. Further preferably the lever member comprises a front surface that is substantially transverse to the axis of the tip and one or more side surfaces that extend in a direction substantially parallel to the axis of the tip. In at least some examples the catch means may be carried by the front surface of the lever member or provided at a junction between the front surface and side surface(s).

In some embodiments a user may release the hub from the catch means by manual intervention, e.g. grabbing the hub to pull it away from the catch. Although this would require a user to handle the hub, there is still an advantage that the connection has already been loosened by the disconnecting member so that he does not need to pull the hub away with the same force as would be required to overcome the friction fit. However this is not ideal as the user may need to hold the device in one hand and pull the hub away with the other hand. Furthermore there may be a higher risk of injury if the hub comprises a needle or other sharp device. Accordingly the device preferably comprises means to release the catch. Once the catch means has operated to catch the female hub, after the friction fit has been released, the catch release may then be operated so that the hub can be separated from the device e.g. so that a used needle can be dropped into a sharps bin or the like. Once the catch is released the hub may fall away from the tip under gravity rather than under a force applied by movement of the disconnecting member. This can provide much better control of the hub as it is separated from the device.

In some embodiments the device may comprise a catch release means independently of the disconnecting member, for example a catch release actuator that can be operated by user after operating the disconnecting member. This may provide a user with flexibility in releasing the hub e.g. operating the disconnecting member to loosen the friction fit and (at the same time or later) pointing the hub towards a disposal unit before operating the catch release actuator. However it desirable for the catch to be engaged and then released by a single user operation to ensure a smooth workflow. It is most convenient for the friction fit to be loosened, the hub caught, and the hub then separated from the device, solely through operation of the disconnecting member. This means that a user needs only to operate the disconnecting member and the device may be suited for single-handed operation. Thus in a preferred set of embodiments the catch means is arranged to be released by movement of the disconnecting member. In some embodiments the catch means may be released by further movement of the disconnecting member towards or beyond the second position, e.g. the disconnecting member pushing the hub into the catch and then past the catch. However, in other embodiments it is preferable that the catch means is released by the disconnecting member moving from the second position back towards the first position proximal to the fluid chamber. In embodiments where the disconnecting member comprises a lever member pivotally mounted to the device, the catch means may be released by the lever member pivoting back towards the first position. Where the lever member preferably comprises a front surface that is substantially transverse to the axis of the tip and one or more side surfaces that extend in a direction substantially parallel to the axis of the tip, the catch means may be released by the lever member pivoting to move the front surface back to the first position proximal to the fluid chamber.

In embodiments where the disconnecting member e.g. a lever member is freely mounted to the device then a user may actively move the disconnecting member back to the first position to release the catch, e.g. by pulling the lever member back. However this movement may be assisted by the lever member(s) being pivotally mounted so as to be resiliently biased into the first position, as is mentioned above. It may be preferable that any disconnecting member is resiliently biased into the first position. This means that when a user releases the disconnecting member e.g. lever mechanism after loosening the friction fit, the catch means is automatically released by the disconnecting member(s) moving back to the first position under the resilient bias. The resilient bias may be provided as part of the catch means and/or independently of the catch means. For example a spring member may be arranged to resiliently bias the disconnecting member into the first position, preferably a spring member integrated with the disconnecting member. This enables a single user operation to have the effect of loosening the friction fit, catching the hub, and then releasing the hub for it to gently fall away from the device. For example, a user may only need to squeeze a lever member and then let go. In embodiments according to any of the aspects of the invention described above, the disconnecting mechanism may provide an additional function as an information carrier. Accordingly the disconnecting member or lever mechanism may comprise an information carrier. In one set of embodiments an information carrier may be integrated with the disconnecting member or lever mechanism. For example, the information carrier may take the form of engraved, embossed or printed information relating to the type of device and/or the fluid being transferred. The information carrier may take the form of a writeable surface for a user to add information relating to the fluid being transferred by the device (e.g. designation of medicine and/or dose) and/or to a subject (e.g. patient identification). This can enhance patient safety. The information may take the form of a barcode, QR code, EAN code, printed memory, or any other form of near field identification system. Colour coding may be used to convey information.

In another set of embodiments the disconnecting member or lever mechanism may comprise means for receiving an information carrier. The information carrier may be selectively attached to the receiving means by any suitable means, for example by adhesive attachment, mechanical attachment (such as a snap or clip fitting, or a fabric hook-and-loop fastener (e.g. Velcro)), magnetic attachment, etc. The information carrier may be attached to the receiving means at an appropriate time in the life cycle of the device. Thus a manufacturer could pre-label a device with information before it is supplied. Alternatively the device may be provided as part of a kit with one or more information carriers, e.g. attachable labels, and then an end user may attach information to the device by virtue of the receiving means. An end user could, for example, attach a patient-specific label or the like. In a further alternative, an information carrier may be provided together with a medicament or other fluid to be transferred and then attached to a device when the fluid is taken. For example, an information carrier could be custom made for each fluid container (such as a vial of medication) and follow the container from the producer to the user, ready to be attached to the device e.g. when medication is drawn into a syringe.

While it has been recognised that a disconnecting member or lever mechanism provides a device such as a syringe with a new opportunity for carrying information, the feature of providing a dedicated means for a fluid transfer device to receive an information carrier is considered novel and inventive in its own right. Thus when viewed from a yet further aspect the present invention provides a fluid transfer device comprising a fluid chamber and, on an external surface of the chamber, means for receiving an information carrier. The receiving means could take the form of a receiving void, depression, window or sleeve. In a preferred set of embodiments the receiving means enables an information carrier to be clipped to the device.

As mentioned above, an information carrier could be selectively attached to the receiving means by one or more of: adhesive attachment, mechanical attachment, or magnetic attachment. The information carrier may comprise one or more of: printed, embossed, engraved, or written information. The information may takes the form of one or more of: colour coding, barcode, QR code, EAN code, printed memory, or any other form of near field identification system.

It is an advantage of the present invention that the tip of the device can be connected to a hub without needing to screw any components of the connection, i.e. a so-called Luer slip connection rather than a Luer lock connection. Preferably the friction fit between the tapered tip of the fluid transfer device and a corresponding female hub can be solely relied upon to provide a secure, fluid-tight connection.

The Applicant has recognised that the connection and disconnection of a fluid transfer device, in particular in a medical setting, can be closely tied to the risks of contamination and transmission of infection. It is generally preferable for fluid transfer devices to be designed for single use and discarded after use. Even if a component of the device which does not come into contact with fluid is removable, for example the disconnecting member, re-use may not be desirable as the component will no longer be sterile. Such components would have to be cleaned and sterilised before re-use. Advantageously the device may be designed to deter users from re-use. Accordingly, in a set of embodiments the disconnecting member is arranged such that movement from the first position to the second position renders the member unusable thereafter. This may be achieved in various way. For example, the disconnecting member or part of a disconnecting mechanism may be destroyed when moving to the second position. In another example, the disconnecting member may become locked when moving to the second position. The device may be provided with suitable means to disable e.g. destroy, lock, etc. the disconnecting member once it has moved to the second position and disconnected a hub from the tip. This will force users to discard the device after use.

Alternatively, or in addition, the device may be designed for single use by making the male connector tip or fluid transfer tip unusable after the disconnecting member has been operated to release a hub from its friction fit to the tip. In a set of embodiments this may be achieved by arranging for the disconnecting member to at least partially break the tip when it moves towards the second position. The disconnecting member may act to break the tip by bending, shearing, crushing, cutting, piercing, etc.—by any suitable means that damages the tip so that it can not be connected to another hub after use of the device. In a preferred set of embodiments the disconnecting member comprises one or more lever members pivotally mounted to the device with movement of the lever member(s) towards the second position arranged to apply a turning force to the tip. This turning force may be sufficient to deform or snap the tip, for example if it is made of a moulded plastics material. The effect may be improved by forming the tip with an area of weakness to be acted on by the lever member. Where the lever member preferably comprises a front surface that is substantially transverse to the axis of the tip and one or more side surfaces that extend in a direction substantially parallel to the axis of the tip, the tip may be arranged to pass through a slot or aperture in the front surface. The sides of the slot or aperture can press against the tip, especially an area of weakness in the tip, to break the tip as the lever member pivots to move the front surface towards the second position. In such embodiments it is ensured that the tip is destroyed at the same time as disconnecting the device from a hub, so that it can not be re-used. This may be particularly desirable where the device comprises a syringe connected to a hub carrying a needle for the injection of medicines such as vaccines, e.g. for use in developing countries.

The fluid transfer device may comprise any type of device used to transfer fluid—liquid and/or gas—either to or from a fluid receptacle. The fluid receptacle may be inanimate or it may be part of a living subject, for example a bodily cavity, organ or vessel, such as a vein or artery. Although the present invention may find a wide range of uses, preferably the fluid transfer device is a medical device. The fluid transfer device may comprise one or more devices such as a syringe, pre-filled syringe, IV delivery device e.g. "drip", transfusion device, fluid pump, stopcock, aspirator, or suction device. The device may be made to meet the relevant medical standard(s), for example ISO 7886 for sterile hypodermic syringes. In one set of embodiments the tip is connected to a corresponding female hub comprising a cannula or hypodermic needle. In such embodiments the device may take the form of a syringe. Where the fluid transfer device is a syringe, the male tip may be centric or non-centric of the fluid chamber e.g. barrel of the syringe. The fluid chamber may have a volume of 0.5 ml, 1 ml, 2 ml, 3 ml, 4 ml, 5 ml, 10 ml, 20 ml, 30 ml, 50 ml, 100 ml or greater. Smaller syringes (e.g. 5 ml or less) tend to have a centric tip while larger syringes (e.g. 10 ml or greater) may have a non-centric tip. The type of disconnecting member, and/or the way it is mounted to the device, may depend on whether the tip is centric or non-centric, which may depend on the volume/diameter of the syringe. In one set of embodiments a syringe with a non-centric tip is provided with a lever member for disconnection as the lever may be more easily mounted to one side of the tip with enough space to generate leverage. In another set of embodiments a syringe with a centric tip is provided with a sliding member for disconnection. Of course a syringe with a centric tip may instead be provided with a lever member for disconnection.

Although the fluid chamber e.g. barrel of a syringe may vary in diameter and volume, the tip preferably meets the Standard ISO 594 (1986), EN 20594-1 (1993) or EN 1707 (1996) for conical fittings with a 6% (Luer) taper for syringes, needles and certain other medical equipment. Accordingly the friction fit is preferably standardised with the tip having the same diameter and taper regardless of the size of the syringe or other device. It is a preferred feature according to all aspects of the invention that the tip is in the form of a standard Luer slip tip with a 6% taper. In less preferred embodiments the tapered male connector tip may be surrounded by a screw thread that grips a hub in addition to the friction fit, but this can make it more difficult for the disconnecting member to operate. Even if the screw thread or other gripping collar is made weaker than standard to facilitate release of the hub, it is not ideal for there to be a connection beyond the friction fit. Further preferably the tip is connected to a corresponding female hub exclusively by a friction fit. In other words, a Luer lock collar or the like is not part of the connection.

It has been found that the range of movement of the disconnecting member between the first and second positions is preferably at least 2 mm, 3 mm, 4 mm, 5 mm, 6 mm, 7 mm, 8 mm, 9 mm or 10 mm. The range of movement may be up to 5 mm, 6 mm, 7 mm, 8 mm, 9 mm, 10 mm, 11 mm, 12 mm, 13 mm, 14 mm, 15 mm or more. Such movements can be sufficient to release the friction fit of a Luer slip tip even if the connection has been pressurised by the transfer of fluid.

While the present invention has been described so far in the context of a fluid transfer device comprising a "male" tapered tip, it will be appreciated that a friction fit between a device and a corresponding hub may equally be achieved by reversing the male and female parts of the connection. Accordingly, in each aspect and embodiment of the invention disclosed herein the male tip could be replaced with a tapered female part that forms a friction fit when a corresponding male part provided by a hub is inserted therein instead. The disconnecting member would still act to release the friction fit, this time moving along the female part to push away the male part inserted therein. Although such embodiments depart from the standard design of a Luer slip connection for fluid transfer devices such as syringes, it is envisaged that a new standard could be implemented with the male and female parts reversed as outlined here.

The present invention therefore extends to a fluid transfer device comprising a fluid chamber in communication with a fluid transfer tip, the fluid transfer tip comprising a tapered friction fitting for a corresponding hub, and further comprising a disconnecting member moveable relative to the fluid transfer tip so as to release the friction fitting. In one set of embodiments the disconnecting member comprises a lever member pivotally mounted to the device. The lever member preferably comprises a front surface that is substantially transverse to the axis of the tip and one or more side surfaces that extend in a direction substantially parallel to the axis of the tip. The front surface may be arranged to push against the hub to release the friction fit, e.g. as the lever member pivots to move the front surface from a first position proximal to the fluid transfer to a second position spaced away from the fluid transfer tip. In addition, or alternatively, the device may further comprise a catch means arranged to catch the hub after the friction fitting has been released. In addition, or alternatively, one or more of the other features described hereinabove may be combined with such a device.

These and other features and improvements of the present application and the resultant patent will become apparent to one of ordinary skill in the art upon review of the following detailed description when taken in conjunction with the several drawings and the appended claims.

BRIEF DESCRIPTION OF THE DRAWINGS

Some preferred embodiments of the present invention will now be described, by way of example only, and with reference to the accompanying drawings, in which:

FIGS. 9a to 9e show a fourth embodiment of a disconnecting mechanism for a syringe;

FIGS. 11a to 11e show a fifth embodiment of a disconnecting mechanism for a syringe;

FIGS. 12a to 12c show various ways to lock a lever to a syringe barrel;

FIGS. 20a and 20b show a 13th embodiment of a disconnecting mechanism for a syringe;

FIGS. 21a and 21b show a 14th embodiment of a disconnecting mechanism for a syringe;

FIGS. 22a and 22b show a variant of the 13th embodiment for a fluid transporting hose instead of a syringe;

FIG. 23 shows an alternative syringe design with a female connector tip that is tapered to form a friction fit when a corresponding male hub is inserted therein;

FIGS. 24a-24f show a first embodiment of a disconnecting and catch mechanism for a syringe;

FIGS. 25a and 25b show the disconnecting and catch mechanism in operation;

FIGS. 26a-26d show a second embodiment of a disconnecting and catch mechanism for a syringe;

FIG. 27 shows a variant of a lever member for a disconnecting and catch mechanism;

FIGS. 32a-32c show a seventh embodiment of a disconnecting and catch mechanism for a syringe;

FIGS. 39a-39g show a 13th embodiment of a disconnecting and catch mechanism for a syringe;

DETAILED DESCRIPTION

Figure 1:
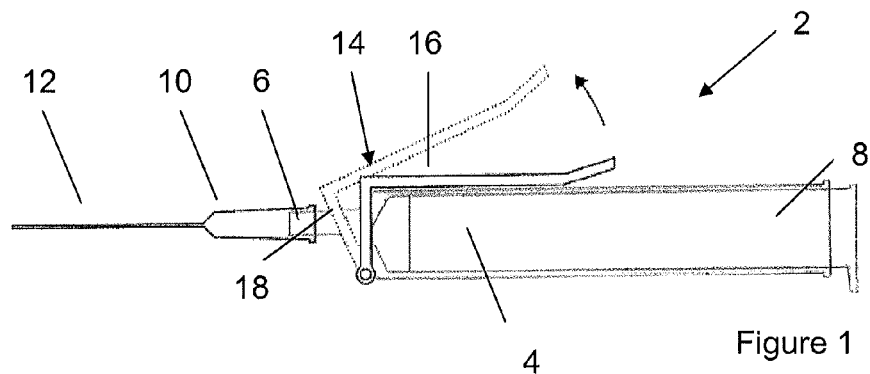
FIG. 1 is a first embodiment of a disconnecting mechanism for a syringe.

FIGS. 1 to 41 illustrate various different disconnecting mechanisms for a fluid transfer device taking the form of a syringe 2. The syringe 2 generally comprises a fluid barrel 4 in communication with a male tip 6. The tip 6 is tapered from its aft end, proximal to the barrel 4, to its forward end according to the standard Luer slip design i.e. a 6% taper (equivalent to around) 3.43°). Fluid in the barrel 4 can be transferred through the tip 6 by pushing or pulling a plunger 8 inserted in the barrel 4. However, although a syringe 2 is shown in each of the embodiments for simplicity, such a Luer slip tip could equally be in communication with another fluid transfer device such as a drip.

As is seen throughout FIGS. 1 to 18, the male tip 6 may be connected to a corresponding female hub 10 in order to transfer fluid to a needle 12 or other cannula. Although not shown, the needle 12 might already be inserted into a living subject, for example for IV therapy with the hub 10 providing an IV port for the injection and/or removal of various fluids. The tapered tip 6 is inserted into the hub 10 and forms a friction fit that is fluid-tight. In each of the embodiments, a disconnection mechanism is provided that can be manually operated to move relative to the male tip 6 between a first position, proximal to the syringe barrel 4, and a second position spaced from the first position towards the forward end of the male tip 6 so as to push against the hub 10. Operation of the mechanism therefore acts to automatically disconnect the syringe 2 from the hub 10 without a user needing to pull or tug the syringe to release the friction fit of the Luer slip connection. Preferred embodiments provide a lever mechanism to push the tip 6 away from a hub 10.

In the embodiment of FIG. 1 a lever 14 is pivotally mounted to the barrel 4 of the syringe 2. The lever 14 is generally L-shaped with an input arm 16 (which may be planar or curved to match the barrel 4) running along the outside of the barrel 4 and an output arm 18 next to the male tip 6. The output arm 18 may sit to one side of the tip 6 or it may surround the tip 6 if provided with an aperture for the tip 6 to pass through. In a first position (solid line) the input arm 16 of the lever 14 lies flush against the barrel 4 and the output arm 18 is seated at the aft end of the tip 6, proximal to the barrel 4. In this position the syringe 2 can be connected to a hub 10 without any interference. When it is desired to disconnect the syringe 2, the lever 14 can be pivoted to a second position (dotted line) by pushing the input arm 16 away from the barrel 4. The output arm 18 of the lever 14 then moves forward along the connector tip 6 and pushes against the hub 10 to release the friction fit. The lever 14 acts to amplify the force applied to the input arm 16 so that a user can easily disconnect the syringe without requiring a high force. It is not necessary to hold the hub 10. The syringe 2 with its disconnecting mechanism can be operated with one hand. A user is therefore protected from the risk of needle injury while disconnection can be more smooth for the patient than pulling a syringe out of a hub.

Figure 2:
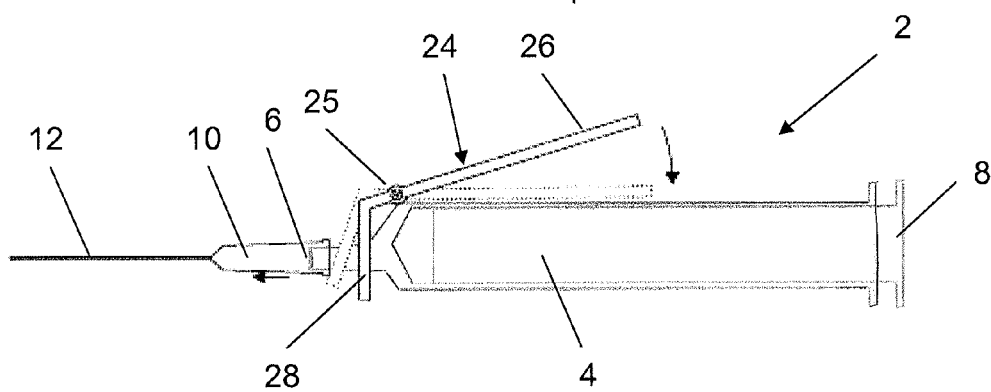
FIG. 2 is a second embodiment of a disconnecting mechanism for a syringe.

FIG. 2 illustrates another embodiment of a lever 24 pivotally mounted to a syringe 2. In this embodiment the lever 24 is pivotally mounted at a point 25 between the input arm 26 and the output arm 28 so that in a first position (solid line) the input arm 26 is spaced away from the barrel 4 while the output arm 28 is seated against the barrel 4, at the aft end of the tip 6. In this position the syringe 2 can be connected to a hub 10 without any interference. When it is desired to disconnect the syringe 2, the lever 24 can be pivoted to a second position (dotted line) by pressing the input arm 26 against the barrel 4. The output arm 28 of the lever 24 then moves forward along the connector tip 6 and pushes against the hub 10 to release the friction fit. The lever 24 may be easier to operate, especially when grasping the syringe 2 with a single hand, as it can be squeezed like a trigger to operate the disconnecting mechanism.

Figure 3:
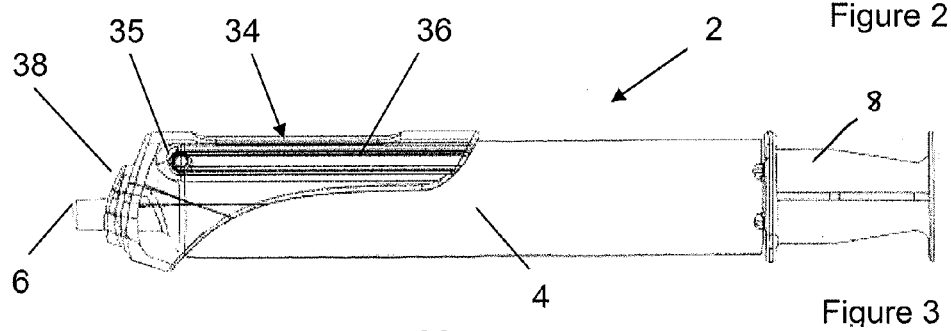
FIG. 3 is a third embodiment of a disconnecting mechanism for a syringe in the preferred form of a lever.
Figure 4A:
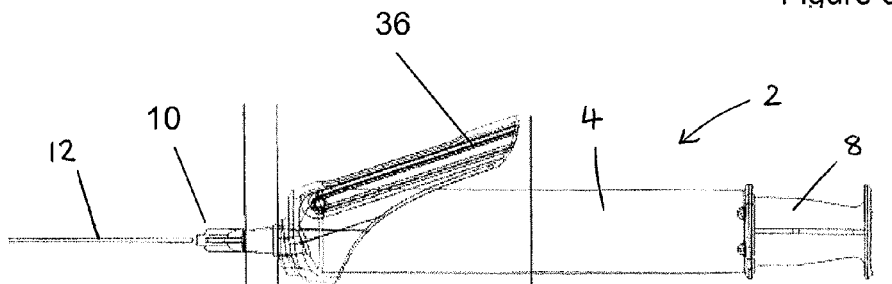
FIG. 4a shows the lever of FIG. 3 in a first position, primed for use
Figure 4B:
FIG. 4b shows the lever of FIG. 3 in a second position, acting to disconnect the syringe from a hub.

There is seen in FIGS. 3 and 4 a preferred lever mechanism that is a variation of the basic embodiment seen in FIG. 2. In this embodiment a lever 34 is shaped to match the cylindrical surface of the syringe barrel 4 and mounted at a forward point of the syringe 2. The cylindrical shape of the lever 34 imparts stiffness so that it is able to efficiently transmit forces without flexing. The lever 34 may be moulded from a plastics material. The lever 34 is pivotally mounted to an axle 35 at the forward end of the barrel 4. The lever 34 has an output surface 38 provided with a slot to accommodate the tip 6 of the syringe 2 and curved so as to vary the force applied. When the syringe 2 is connected to a hub 10, as seen in FIG. 4a, the output surface 38 is pushed back to the aft end of the tip 6 and the lever 34 pivots so that its input arm 36 is spaced from the barrel 4. This movement of the lever 34 provides a visual and tactile feedback to the user that helps to ensure the hub is pushed on to the tip 6 with a tight friction fit. When it is desired to disconnect the syringe 2 from the hub 10, the lever 34 is moved from a first position (FIG. 4*a*) to a second position, seen in FIG. 4*b*, by pressing the input arm 36 against the barrel 4. As the input arm 36 pivots down, the output surface 38 pivots forward along the tip 6 and pushes against the hub 10. The elliptical curvature of the surface 38 provides a reducing force during engagement with the hub 10 so that the syringe is not forcefully ejected.

Figure 5:
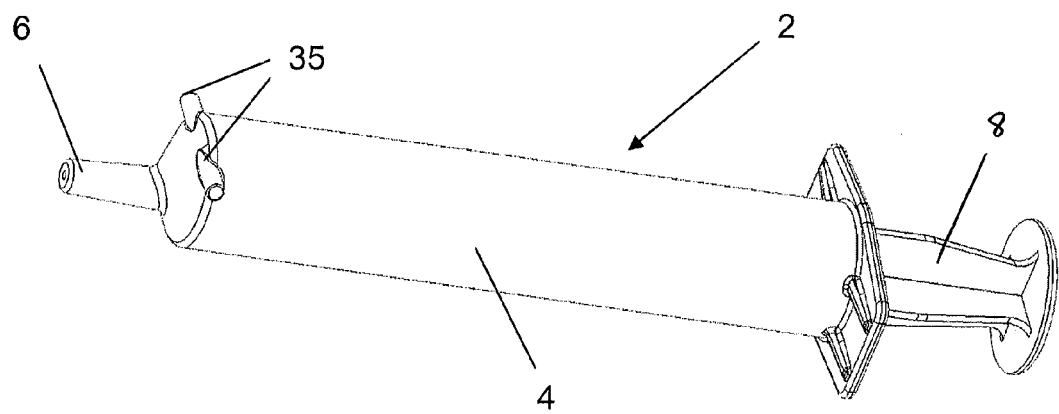
FIG. 5 shows an embodiment of a syringe barrel suitable for mounting the lever of FIGS. 3 and 4.
Figure 6:
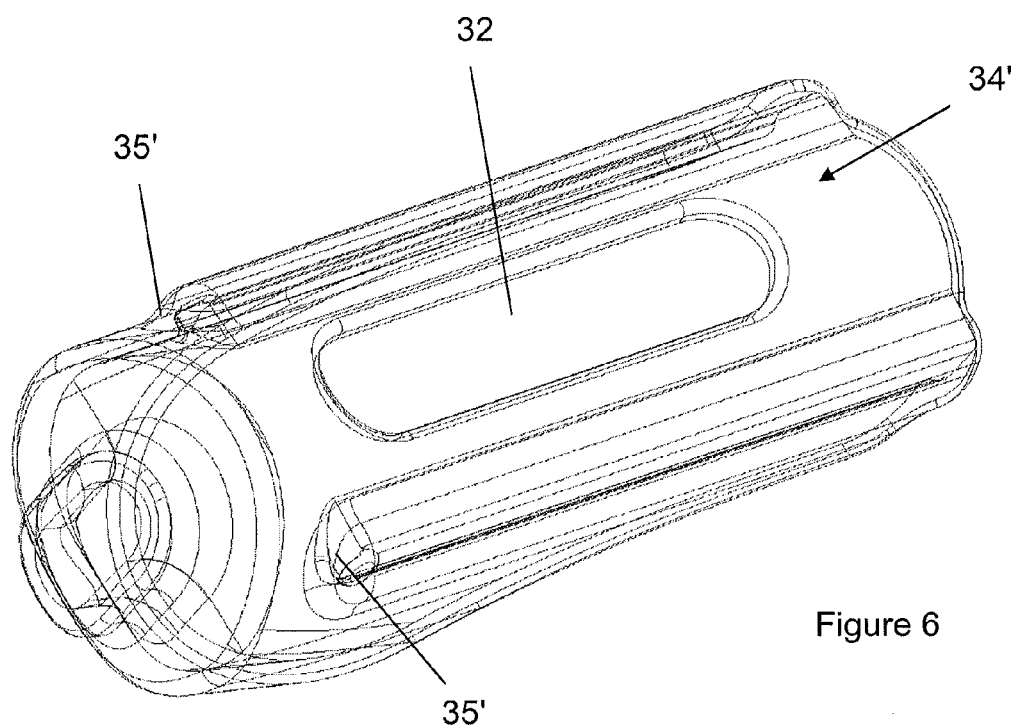
FIG. 6 shows a variant of the lever of FIGS. 3 and 4 with a space for an information carrier.
Figure 7A:
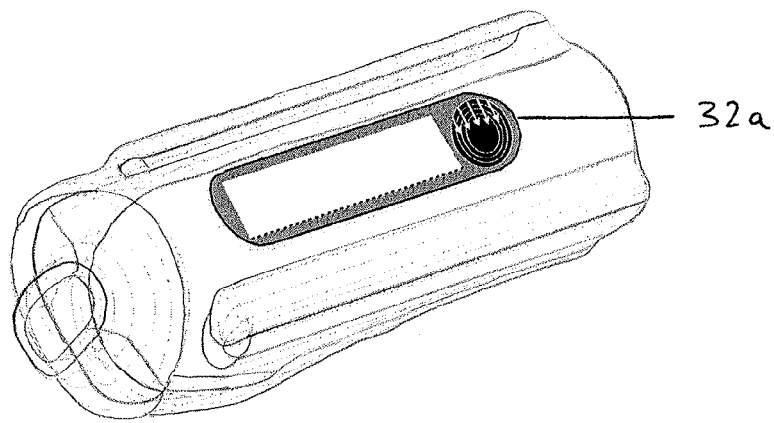
FIGS. 7a to 7d show various forms of an information carrier on the lever of FIG. 6.
Figure 7B:
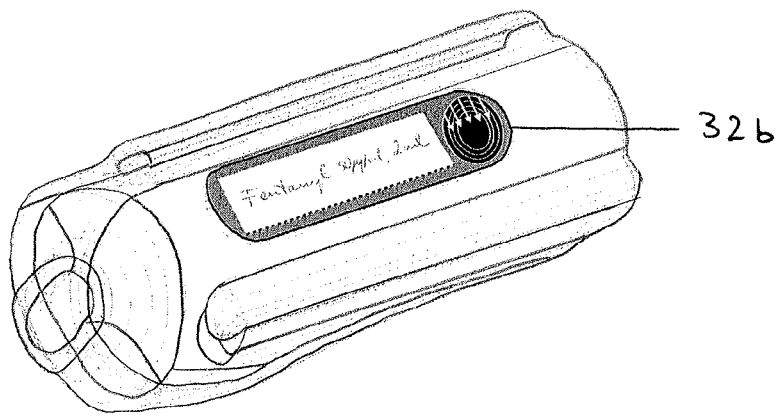
Figure 7C:
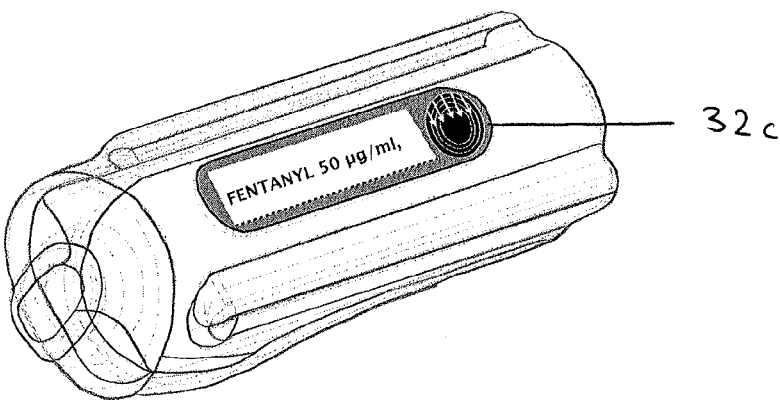
Figure 7D:
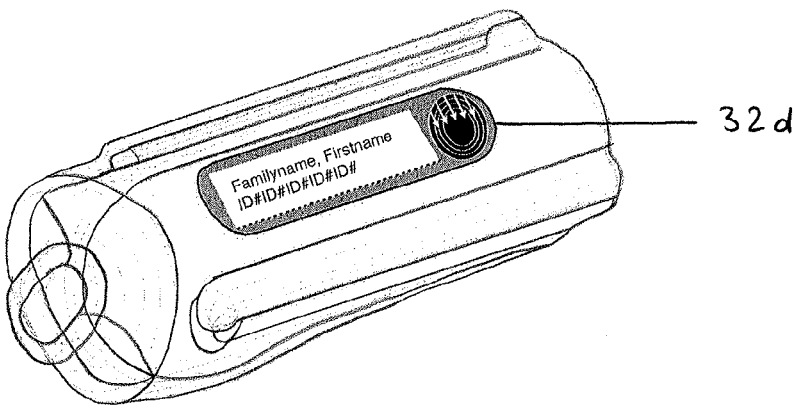

There is shown in FIG. 5 the barrel 4 of the syringe 2 with the lever 34 removed. It can be seen that the barrel 4 has two axles 35 integrally moulded at its forward end, so that the lever 34 can be pivotally mounted with a fixed axis defined by the axles 35. FIG. 6 provides a perspective view of another lever 34' that can be pivotally mounted to the barrel 4 seen in FIG. 5. Internal sockets 35' receive the axles when the lever 34' is clipped onto the barrel. The axles are seated in the sockets 35' in a bi-stable manner, so that the lever 34' can be removed by pushing it forward of the barrel to release the axles from the sockets. The lever 34' also has a void 32 on its surface to receive an information carrier. FIGS. 7*a* to 7*d* give some examples of the type of information carrier that may be received in the void 32, such as a writeable strip 32*a* (FIG. 7*a*), a pre-written label 32*b* (FIG. 7*b*), a pre-printed label 32*c* (FIG. 7*c*) or a patient ID label 32*d* (FIG. 7*d*). The information carrier can be used to display details of the fluid carried in the syringe, such as the medication/dose, and/or patient-specific details. The additional information carrying function of the lever 34' can increase patient safety.

Figure 8A:
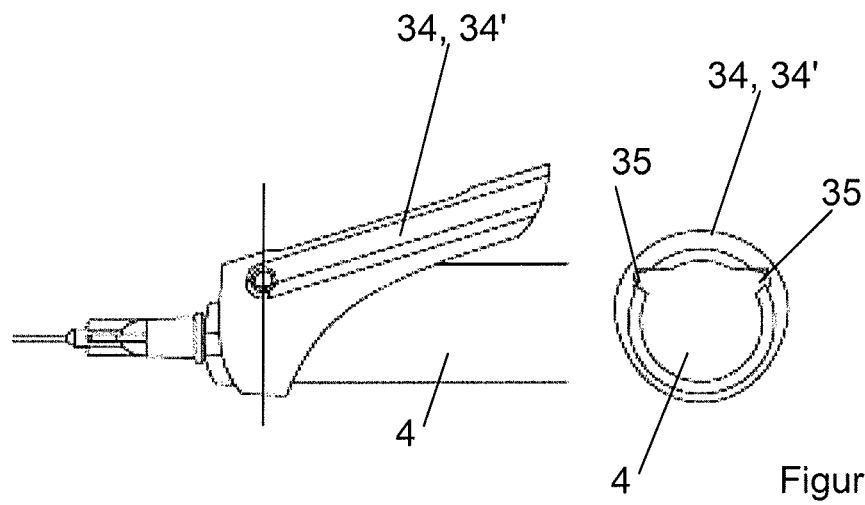
FIGS. 8a to 8c show various ways to mount a lever to a syringe barrel.
Figure 8B:
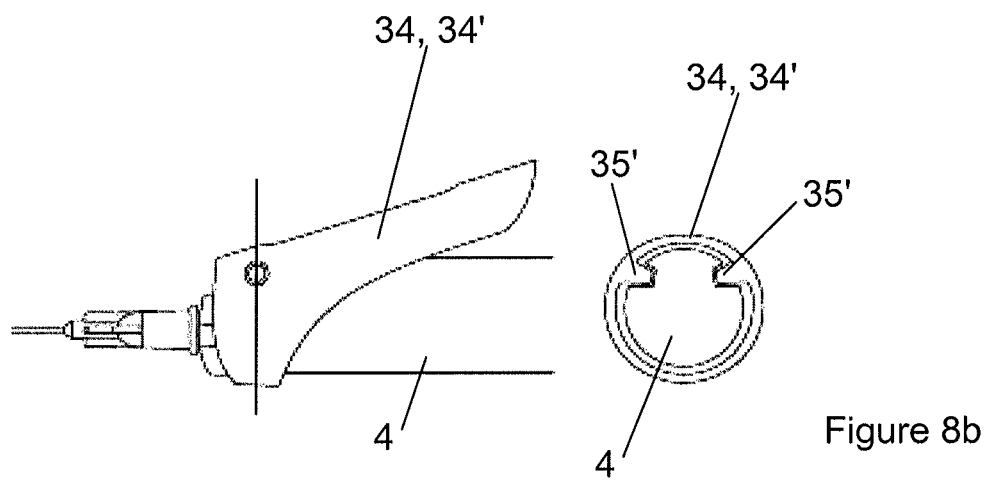
Figure 8C:
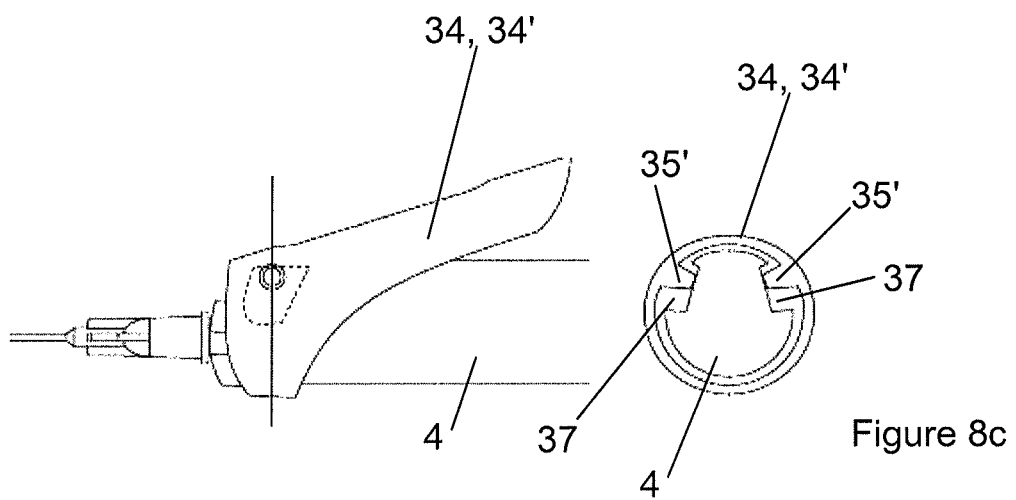

It will be appreciated that a lever 34, 34' can be pivotally mounted to the syringe barrel 4 in a number of different ways. FIGS. 8*a* to 8*c* illustrate some examples. In FIG. 8*a* the axles 35 are provided by the barrel 4. In FIG. 8*b* the axles 35' are provided by the lever 34, 34' and received by sockets on the barrel 4. In FIG. 8*c* it is seen that the barrel 4 does not provide fixed engagement positions for the axles 35' but instead an engagement zone 37. This means that the lever 34, 34' is pivotally mounted with a moveable axis.

Figures 9A, 9B:
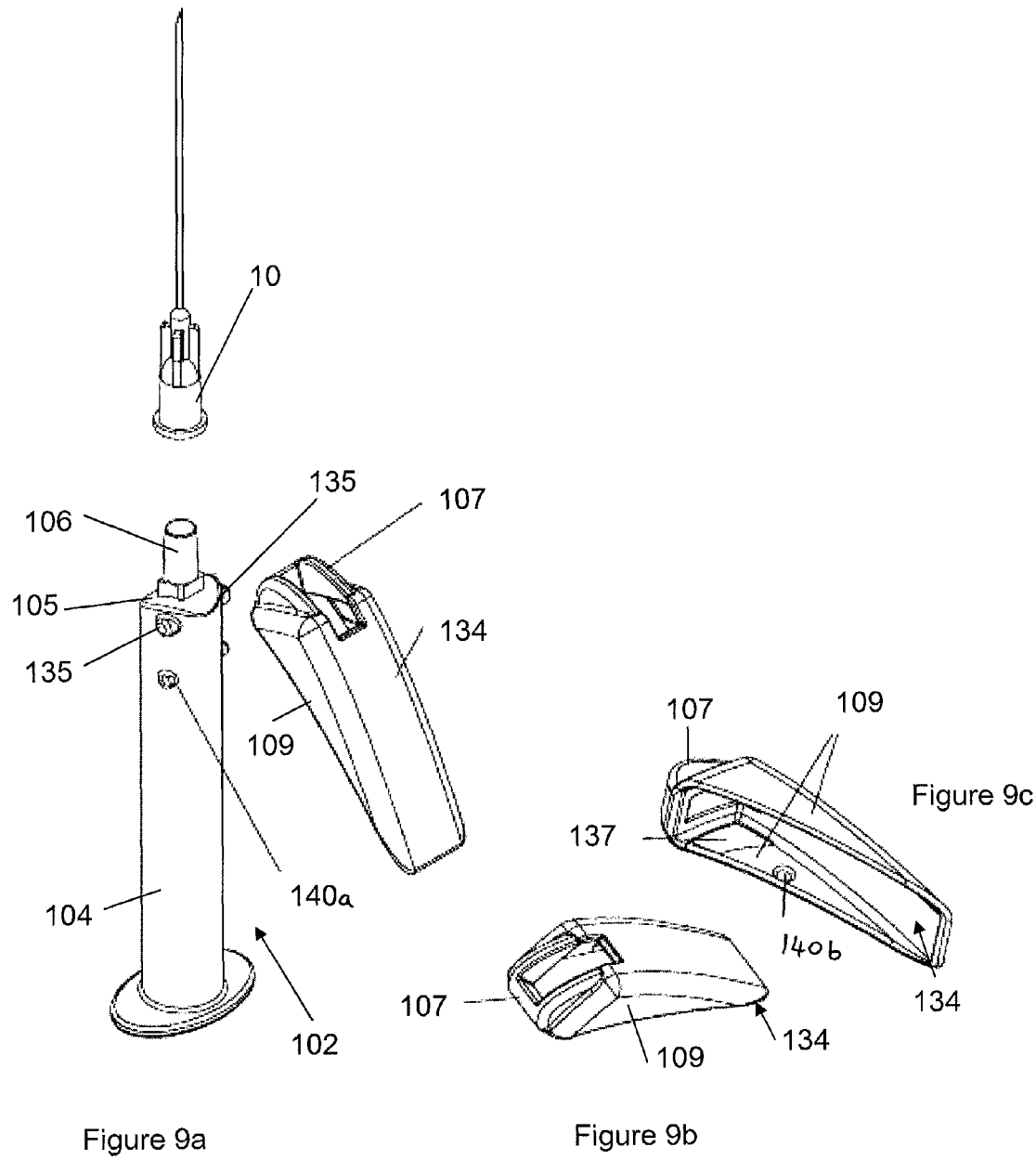
Figure 9D:
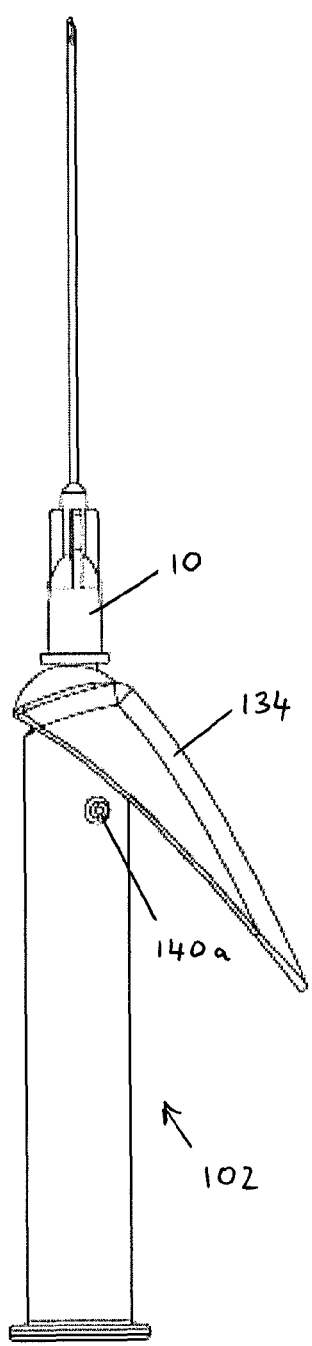
Figure 9E:
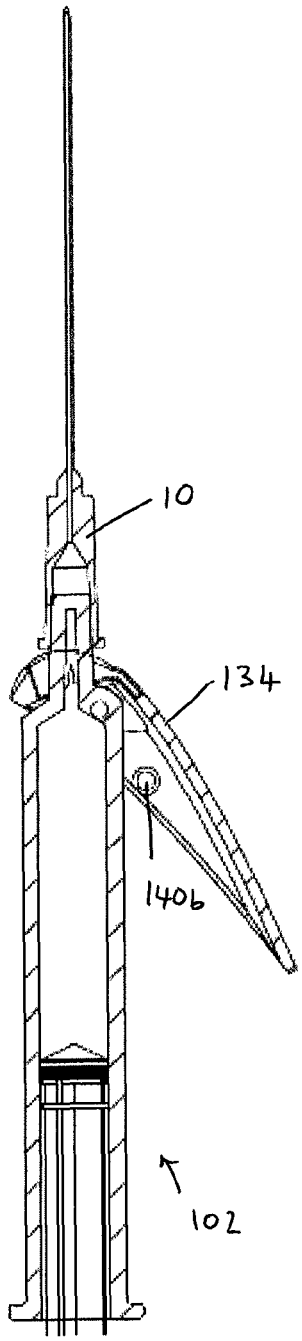
Figure 10A:
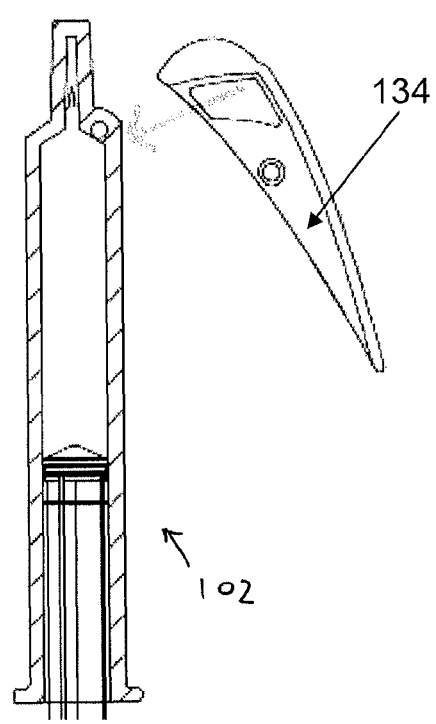
FIGS. 10a to 10f show the operational steps for the disconnecting mechanism of FIG. 9.
Figure 10B:
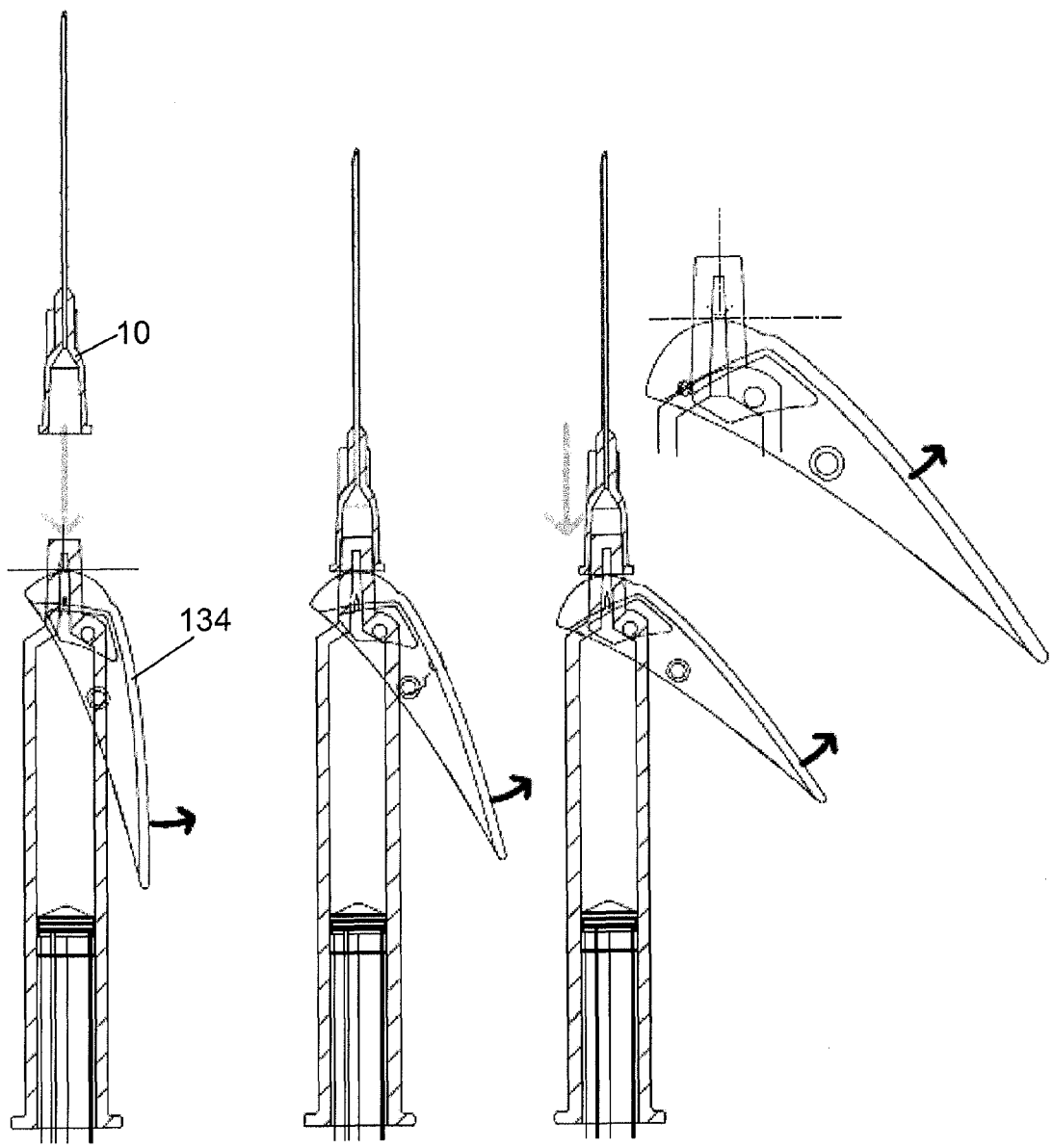
Figure 10C:
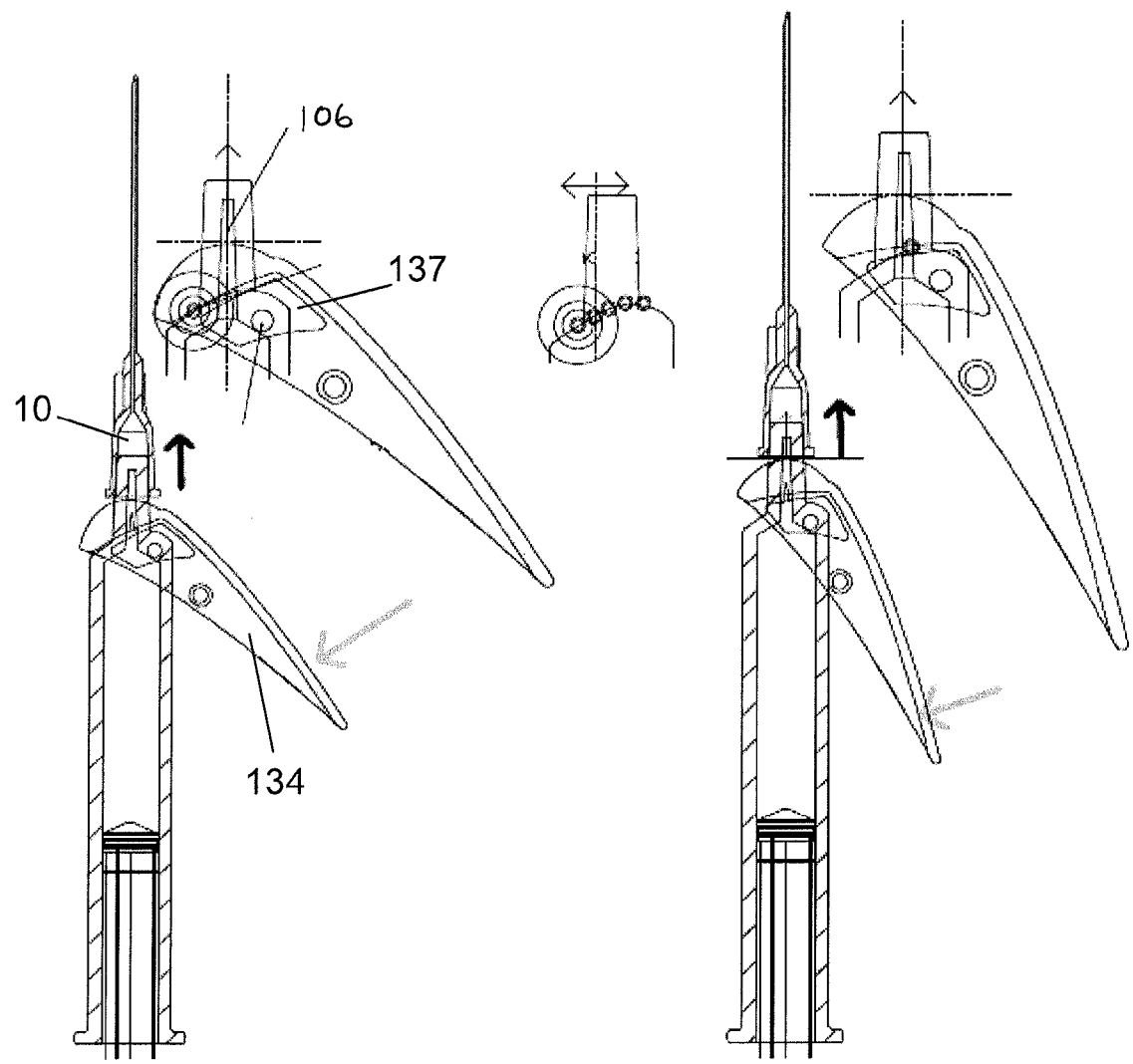
Figure 10D:
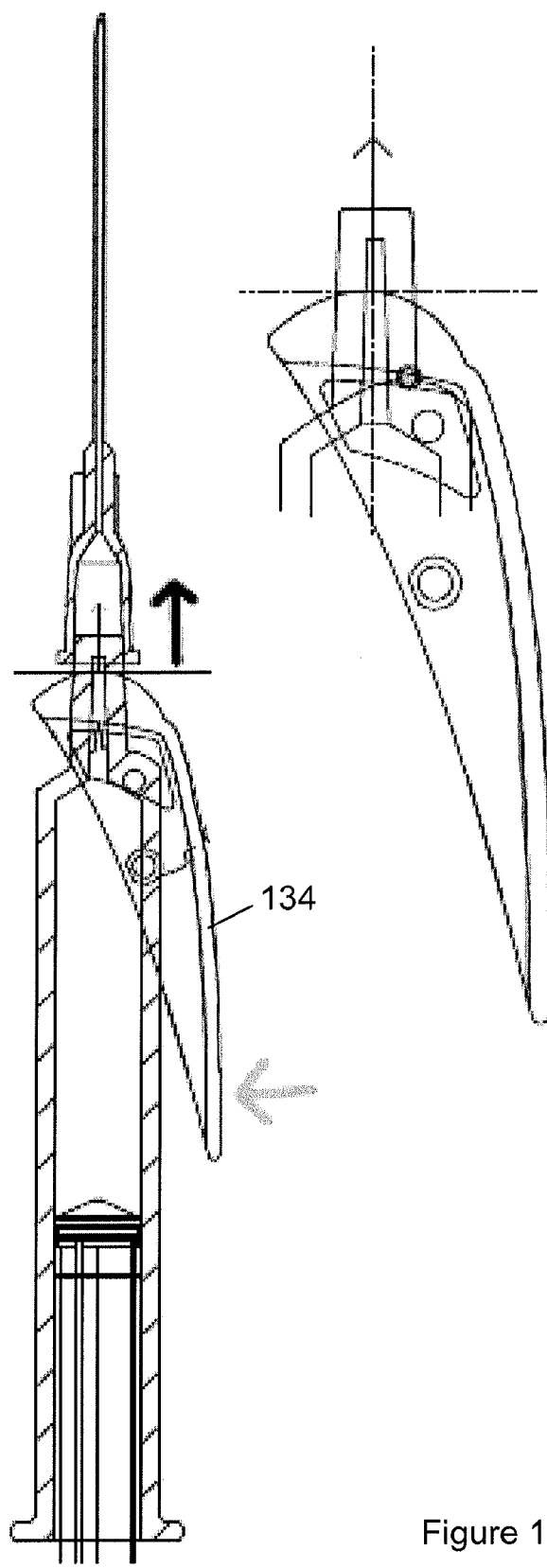
Figure 10E:
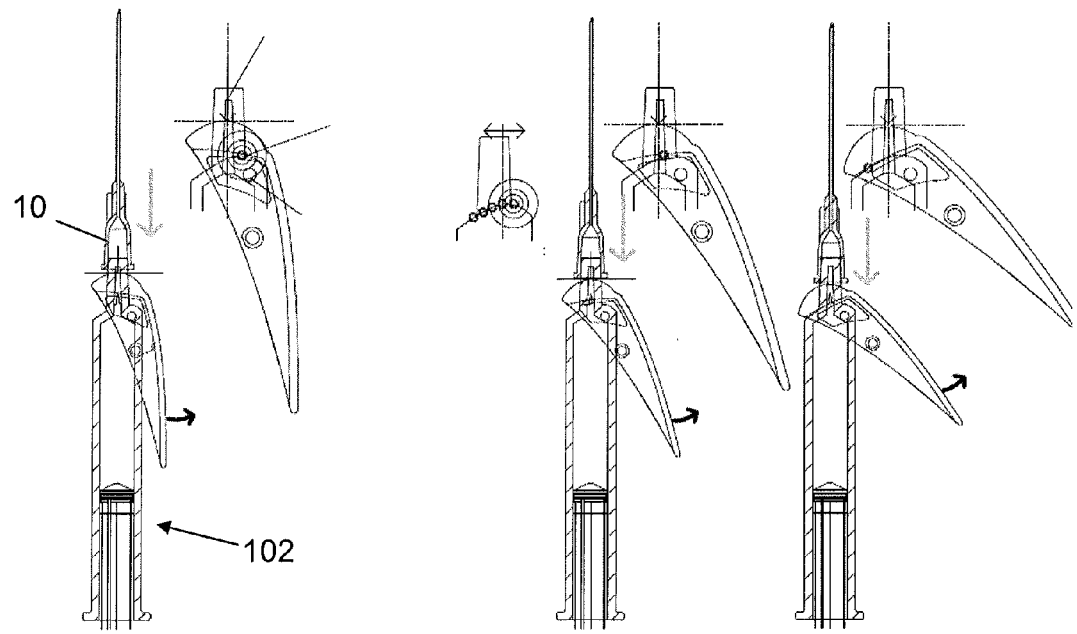
Figure 10F:
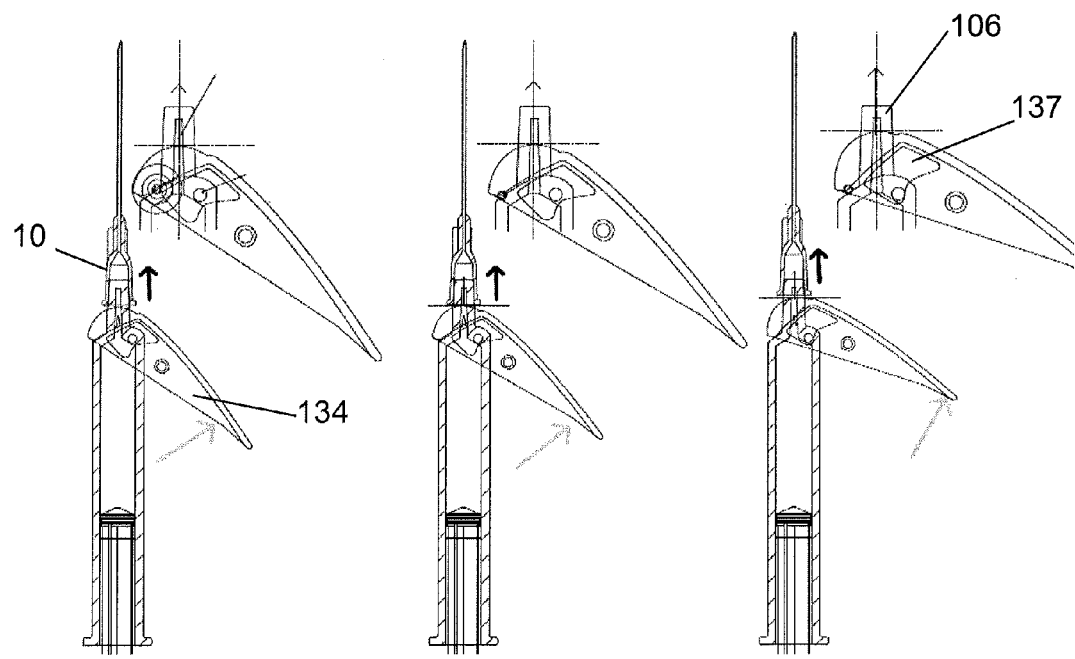

FIGS. 9 and 10 illustrate an embodiment of a lever mechanism comprising a lever 134 that is pivotally mounted with a moveable axis. The parts are shown prior to assembly in FIGS. 9*a* to 9*c*. A syringe 102 comprises a barrel 104 in fluid communication with a tapered tip 106 for connection to a needle hub 10. The syringe 102 is not standard in a number of ways. Firstly, as in previous embodiments, the barrel 104 is provided with axles or pivot engagement points 135 towards its front end. The front surface 105 of the barrel 104 is curved so as to interact with a lever 134 when it is engaged with the syringe 102. As is seen from FIGS. 9*a* and 9*b*, the lever 134 has a front surface 107 that surrounds an aperture for the syringe tip 106. FIG. 9*c* shows the side walls 109 of the lever 134 that extend substantially transverse to the front surface 107. The lever 134 has a rectangular, rather than cylindrical, shape but the three-dimensional structure with the front surface 107 connected to the side walls 109 also achieves a stiffening effect. On the internal surface of the side walls 109, an engagement zone 137 is defined by a recess that receives the pivots 135 when the lever 134 is engaged over the front end of the barrel 104. FIGS. 9*d* and 9*e* show the lever 134 assembled with the syringe 102. An optional feature is for the barrel 104 to provide a locking system 140*a* for the lever 134. The lever 134 carries a corresponding feature 140*b* for the locking system on an inner surface of the side walls 109.

FIG. 10 illustrates various stages during use of the syringe 102 and lever 134. As shown in FIG. 10*a* the lever 134 is mounted by sliding from the side and can be locked for transportation. FIG. 10*b* shows how mounting a needle hub 10 pushes the lock open and releases the lever 134. FIG. 10*c* illustrates how pressing the lever 134 pushes the hub 10 to disconnect it from the tapered tip 106, but with the pivot axis moving in the engagement zone 137 so that a substantially centric force is always applied. FIG. 10*d* shows that when the lever 134 is pressed down it can be locked to prevent further use. FIG. 10*e* shows in detail the response of the moveable pivot axis when a needle hub 10 is mounted to the syringe 102. FIG. 10*f* illustrates how lifting the lever 134 can also push the hub 10 to disconnect it from the tapered tip 106, again with the pivot axis moving in the engagement zone 137 so that a substantially centric force is always applied.

Figure 11A:
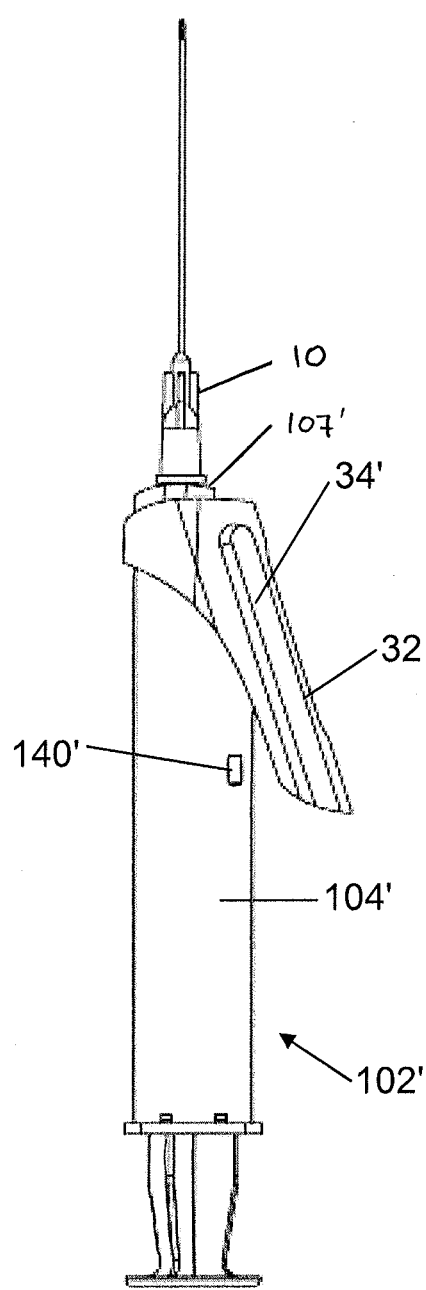
Figure 11B:
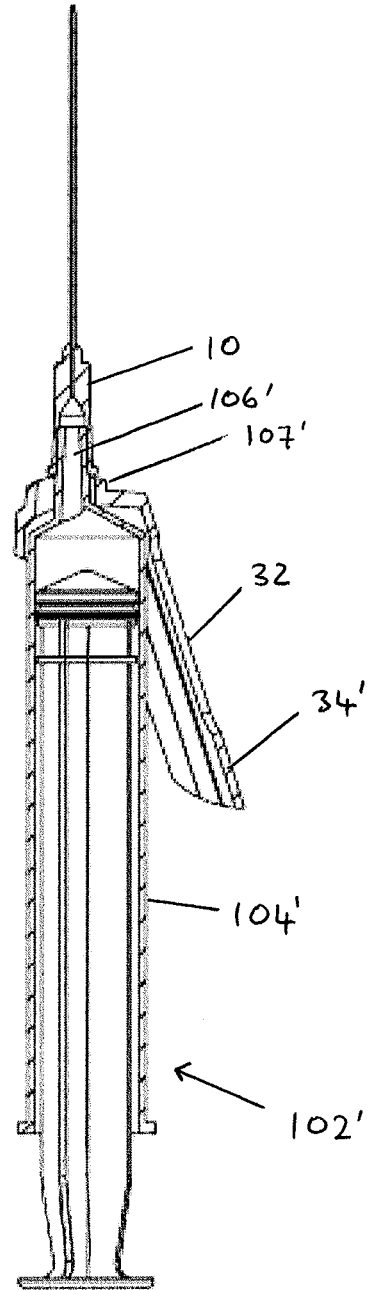

The feature of a locking system for a lever, or for any other kind of disconnecting member, may be generally applicable regardless of the form of the lever mechanism (or other disconnecting mechanism). There is shown in FIG. 11 another embodiment of a syringe 102' with a lever 34' that is similar to the one seen in FIG. 6. As before, the lever 34' has a void 32 that can receive an information carrier (not shown). In this embodiment the barrel 104' of the syringe 102' provides a locking system comprising a pair of latch members 140', as seen from one side in FIG. 11*a*. FIG. 11*c* shows how the lever 34' is mounted to the syringe 102' by sliding it axially over the tip 106' until the lever 34' is engaged over the front surface 105' of the barrel 104'. At this point the latch members 140' engage with the lever 34' so that it is locked against the syringe barrel 104' for packaging and transportation. A hub 10 carrying a needle 12 is usually packaged separately. FIG. 11*d* shows how mounting a needle hub 10 to the syringe 102' pushes against the front surface 107' of the lever 34' so that it pivots, with the force of connection releasing the lever 34' from the two latch members 140'. The locking system may be resilient so that there is an audible "click" or other noise when the latch members 140' are released and the lever 34' is primed ready for use. FIG. 11*e* shows the stages involved in disconnecting the needle hub 10 from the syringe 102'. Pressing the lever 34' towards the syringe barrel 104' causes it to pivot so that its front surface 105' moves along the tip 106' and pushes away the hub 10. Pressing the lever 34' all the way against the syringe barrel 104' causes it to engage the latch members 140' so that it is again locked. An audible "click" or other noise may indicate that the lever 34' is locked.

It will be appreciated that a locking system 140, 140' may take a number of different forms. FIGS. 12*a* to 12*c* illustrate some examples. In FIG. 12*a* a pair of latch members 140' are provided on the outside of the syringe barrel 104' for engagement with a lever 34'. In FIG. 12*b* a pair of latch members 140" are provided on the inside of the lever 34" to engage with a pair of corresponding recesses 141 on the outside of the syringe barrel 104". FIG. 12*c* shows another example without any distinct latch members. Instead, the shape of the lever 34''' is such that it grips onto the outer surface of the syringe barrel 4 when pressed down against it so that the two parts are resiliently locked together.

Figure 13:
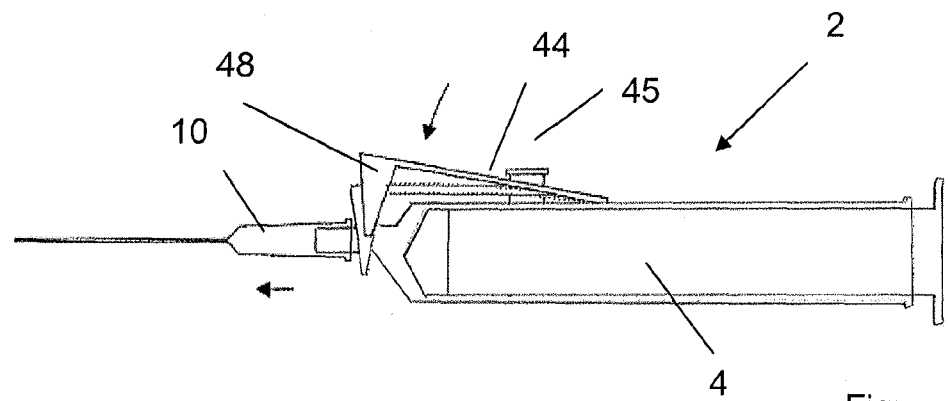
FIG. 13 is a sixth embodiment of a disconnecting mechanism for a syringe.
Figure 14:
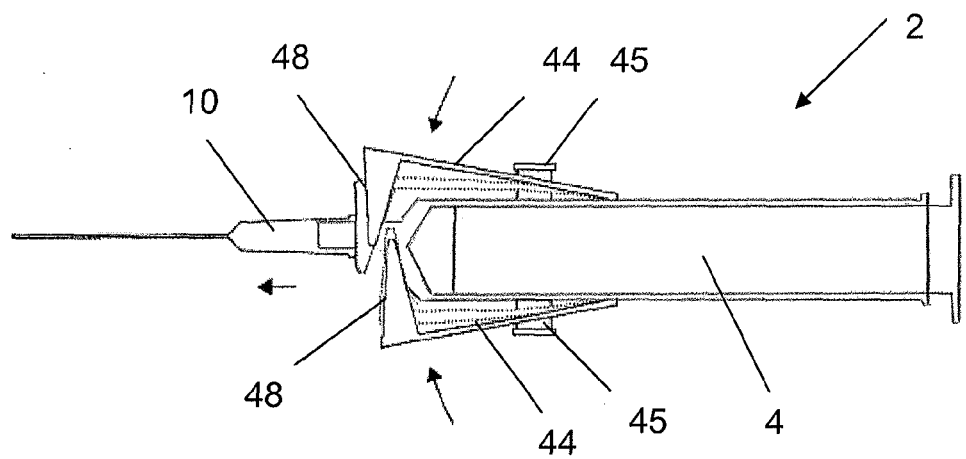
FIG. 14 is a seventh embodiment of a disconnecting mechanism for a syringe.

FIGS. 13 and 14 illustrate some alternative versions of a lever mechanism. In the embodiment shown in FIG. 13 a lever 44 is pivotally mounted to the syringe barrel 4 with an output surface 48 that is angled rather than curved. FIG. 14 shows another embodiment using two angled levers 44. The number of levers and the shape of the output surface may be designed depending on the force that it is desired to apply to the hub 10 to release a particular fluid connection. Each of the L-shaped levers 44 is mounted at a pivot point 45 on a side of the barrel 4.

Figure 15:
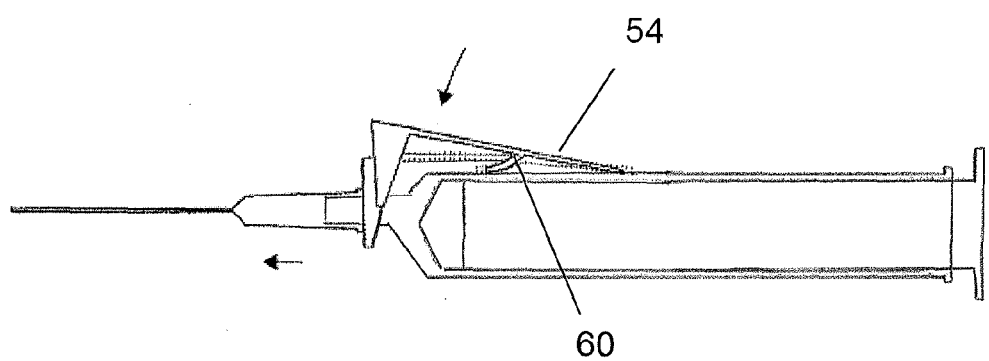
FIG. 15 is an eighth embodiment of a disconnecting mechanism for a syringe.
Figure 16:
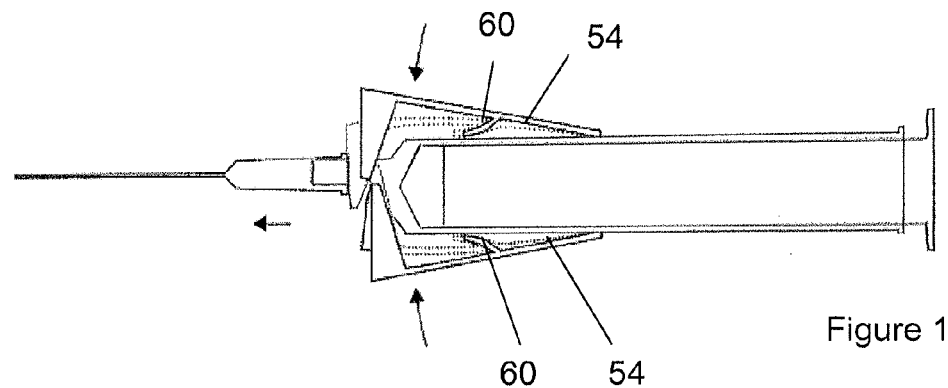
FIG. 16 is a ninth embodiment of a disconnecting mechanism for a syringe.

In each of the embodiments seen in FIGS. 1-14, the lever(s) 14, 24, 34, 34', 34", 44 is/are mounted so as to pivot freely. The disconnecting mechanism can be automatically primed simply by pushing the tip 6 of the syringe 2 into a corresponding hub 10. The hub 10 presses against the output arm of the lever and moves it back into its first position, ready for use. As mentioned above, this can advantageously provide a user with feedback that indicates when the hub 10 has been correctly engaged with a sufficient friction fit. However, in other embodiments it may be desirable for the lever (or other disconnecting member) to be resiliently biased into a first, primed position so that its output arm is automatically clear of the tip 6 when connecting a syringe 2 to a hub 10. FIGS. 15 and 16 show alternative versions of the embodiments of FIGS. 13 and 14, respectively, but with the levers 54 pivotally mounted to the syringe barrel 4 by a resilient member 60. Each lever 54 is resiliently biased into a first position (solid line) and the resilient bias must be overcome when pressing the lever(s) 54 against the barrel 4 to move into the second position (dotted line).

Figure 17:
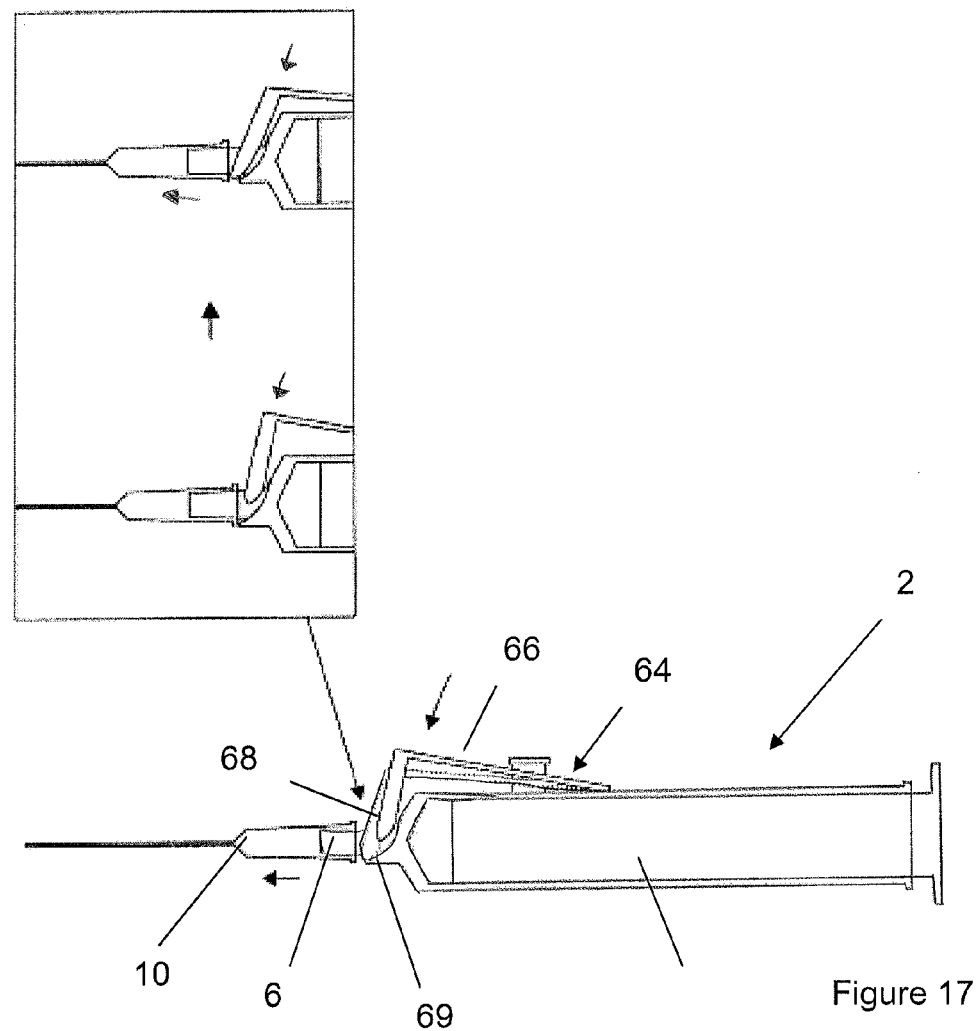
FIG. 17 is a tenth embodiment of a disconnecting mechanism for a syringe.

There is seen in FIG. 17 a further embodiment of a pivotally mounted lever 64. The L-shaped lever 64 is formed of resilient material or hinged, so that the angle between the input and output parts 66, 68 of the lever 64 can be changed. The lever 64 has a curved surface 68 at its forward end that is arranged to run smoothly along a curved (or sloped) surface 69 provided proximal to the barrel 4. As shown in the enlarged image, a "micro lever arm" effect is created as the slope of the surface 69 increases towards the distal end of the tip 6. As the distance transverse to the input part of the lever 64 is reduced, there is a larger angle between the two parts of the lever 64 and the output part is biased forwards to push against the hub 10 with increased force. Such an arrangement can help to amplify the input force and release tight-fitting connections.

The various lever mechanisms described above with reference to FIGS. 1-17 may be designed to release the friction fit of a tip for a wide range of syringes. In particular, the lever mechanism seen in FIGS. 3-6 and 8-12 may be designed for syringes as small as 1 ml or 2 ml in volume. In addition, other mechanism designs may be considered depending on various factors including (but not exclusively): operability, material usage, packaging cost, and size of the syringe (or other fluid transfer device having a tapered tip).

Figure 18:
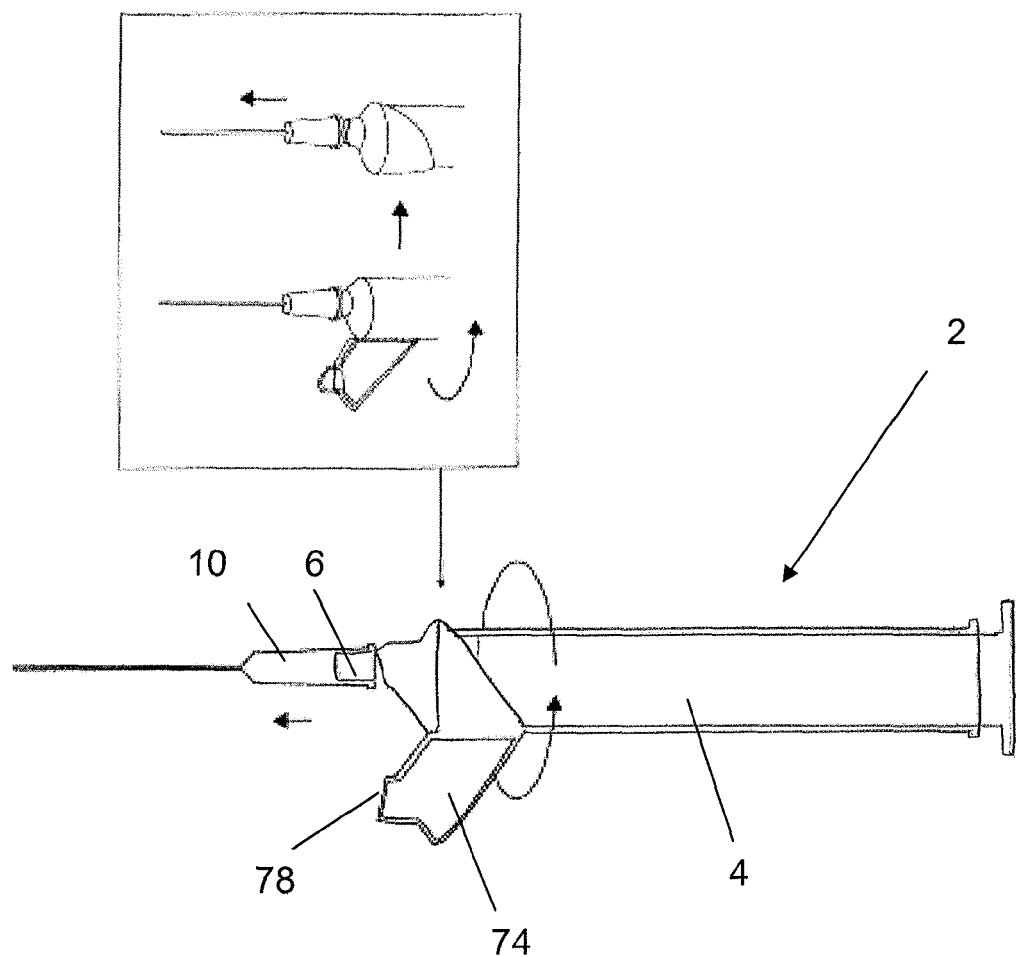
FIG. 18 is an eleventh embodiment of a disconnecting mechanism for a syringe.

FIG. 18 shows a lever member 74 that is pivotally mounted to the barrel 4 so as to have a swinging movement. The lever member 74 is shaped to match the outer contour of the male tip 6 and has an elliptically shaped output surface 78. As is seen in the close-up detail, when the member 74 is swung around the axis of the tip 6 its surface 78 engages against the hub 10 to push it off the tip 6. The surface 78 of the lever member 74 may have a curved e.g. elliptical profile so as to vary the force applied to the hub 10 during disconnection, according to the same principles outlined above. Such a lever mechanism might be used with a syringe 2 having a relatively large diameter e.g. a volume of 10 ml or more.

Figure 19A:
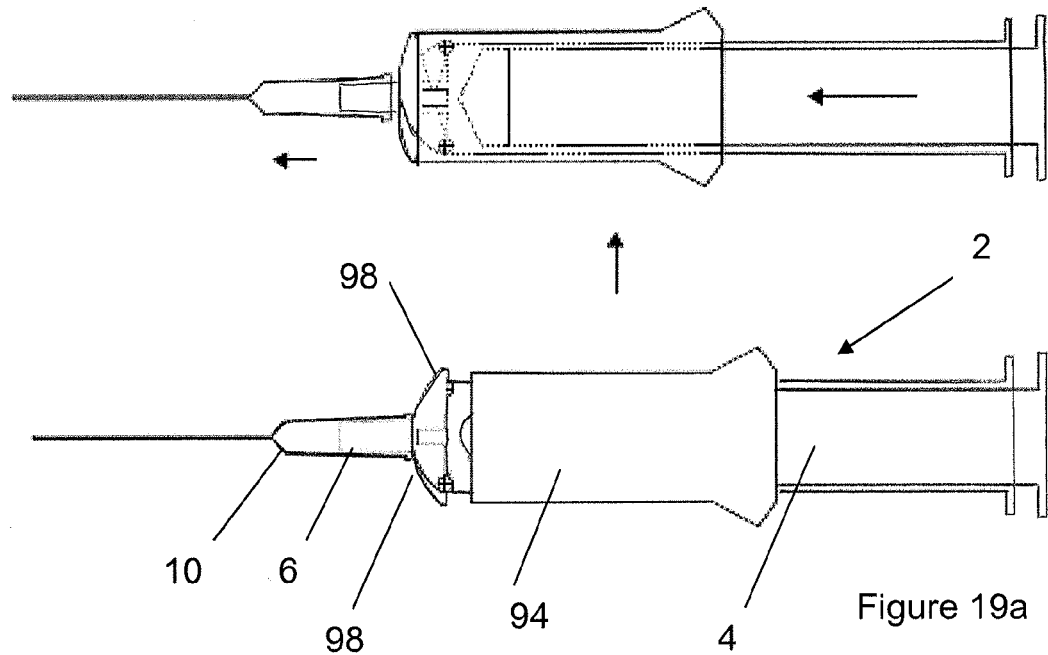
FIGS. 19a-19c show a 12th embodiment of a disconnecting mechanism for a syringe.
Figure 19B:
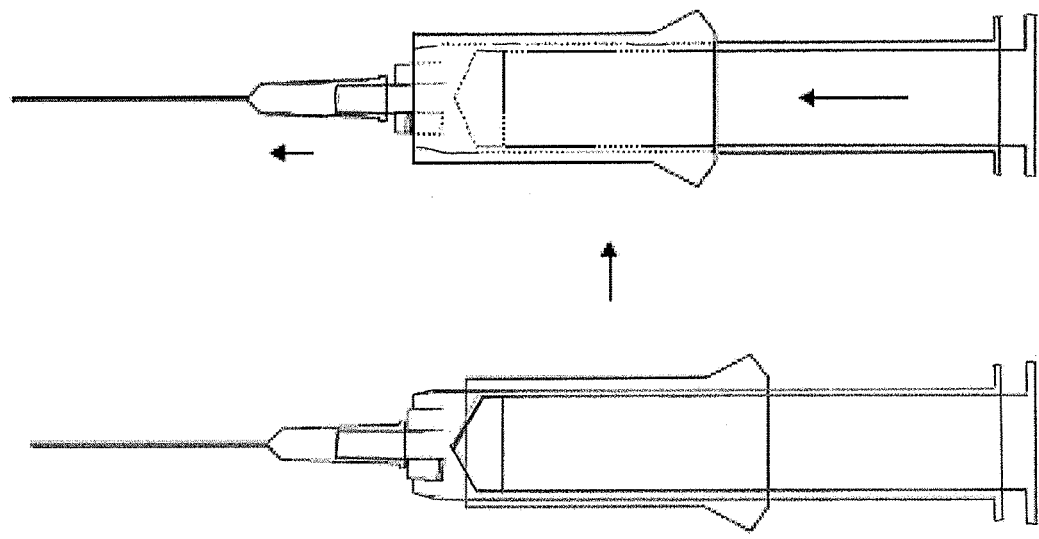
Figure 19C:
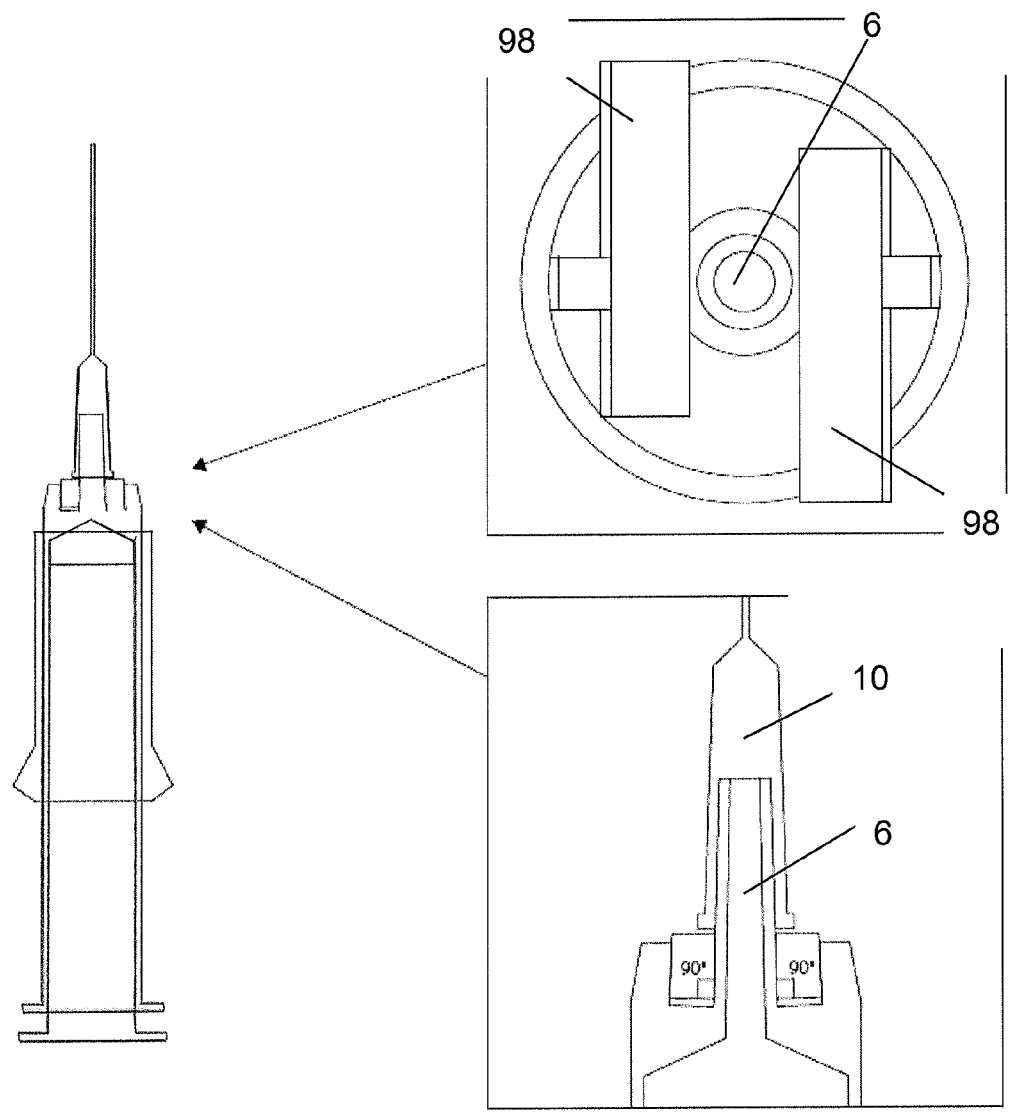

FIGS. 19a and 19b provide side and front views, respectively, of another embodiment that may be particularly suited to small volume e.g. 1 ml or 2 ml syringes as commonly used to administer vaccinations and other small volumes of medication. In this example the disconnecting mechanism comprises a sliding sleeve 94 together with two (or more) pivotally mounted levers 98 at the forward end of the barrel 4 that push against the hub 10 when the sleeve 94 is slid towards and along the male tip 6. Each lever may be pivotally mounted by a living hinge. It can be seen from FIG. 19a that the two levers 98 have a curved surface but due to their symmetrical mounting the overall force acting on the hub is linear i.e. in the direction of the tip 6. The lever surface 98 may have an elliptical profile to provide a desired acceleration or deceleration during movement, as mentioned above. FIG. 19c shows some more detail, in particular the levers 98 being mounted at 90° to the surface of the tapered tip 6. The sleeve 94 may be pushed forward along the barrel 4 simply be being gripped. In fact the pivotally mounted levers 98 could be combined with any sliding and/or pivoting lever that runs along the syringe barrel 4, for example as seen in FIG. 1 or 2.

As is mentioned above, a lever that is pivotally mounted to the barrel of a syringe may not be appropriate for small volume e.g. 1 ml syringes that have a relatively narrow diameter. There may also be required a disconnecting mechanism that can be mounted without using the fluid chamber of a syringe barrel, for example mounted to a fluid transfer tip at the end of a hose, pipe, cannula, etc. FIGS. 20 and 21 illustrate two further embodiments that use a linkage mechanism 124 of pivoting arms at the forward end of the syringe barrel to move along the male tip and push against the hub connected thereto. In the mechanism 124 of FIG. 20 the arms act directly on the hub whereas in the mechanism 124' of FIG. 21 the arms move a ring that pushes against the hub.

Of course various embodiments of the present invention, such as those described above, are not limited to a fluid transfer device in the form of a syringe. FIG. 22 shows the disconnecting mechanism 124 of FIG. 20 applied to the connection between a hub 10 and a fluid transport hose 2' instead of a syringe. Equally, such a hose or other fluid transfer device could replace the syringe shown in any of the other embodiments described above.

Furthermore, although the present invention has so far been described in the context of syringe of other fluid transfer device having a "male" connector tip that is externally tapered to form a friction fit when inserted in a corresponding "female" hub, the various disconnecting mechanisms outlined above may equally find use in releasing the connection between a "female" connector tip and a "male" hub. FIG. 23 shows an alternative syringe 202 with a female connector tip 206 that is internally tapered to form a friction fit when a corresponding male hub 210 is inserted therein. It will be appreciated that such a design deviates from the standard design of a Luer slip connection but the principles of releasing the friction fit are the same and hence encompassed within the scope of the present invention.

Figure 24A:
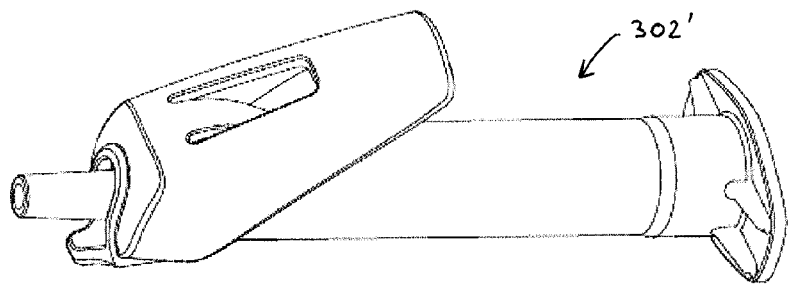
Figure 24B:
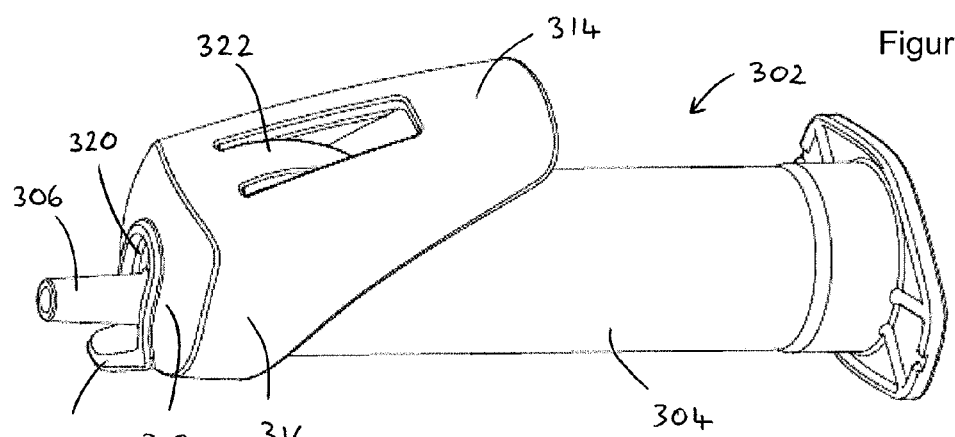
Figure 24C:
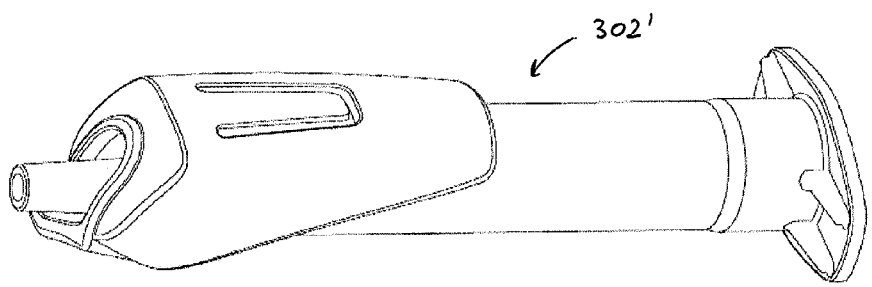
Figure 24D:
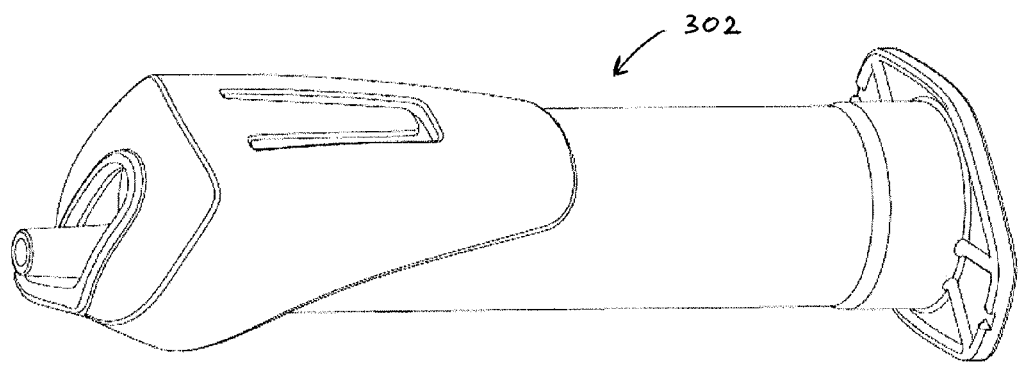

Some further embodiments will now be described that may have elements in common with various of the embodiments above and may be taken to provide additional, or alternative, features. There is seen in FIGS. 24a-24f a first embodiment of a disconnecting and catch mechanism for a syringe. A first syringe 302' seen in FIGS. 24a and 24c may be designed for smaller volumes of fluid e.g. 2-3 ml while a second syringe 302 seen in FIGS. 24b and 24d may be designed for larger volumes e.g. 10 ml. Apart from their size, the syringes 302, 302' are otherwise identical. FIGS. 24a and 24b show the syringes 302, 302' in their natural state. It can be seen e.g. from FIG. 24b that the syringe 302 comprises a fluid barrel 304 in communication with a tapered male tip 306. A lever member 314 is pivotally mounted onto the barrel 304 with the male connector tip 306 protruding through an aperture 320 in a front surface 318 of the lever member 314. In this position the front surface 318 is substantially transverse to the axis of the male connector tip 306. The lever member 314 is integrally moulded from a plastic material and has side surfaces 316 extending back from the front surface 318 to form a shroud surrounding the barrel 304 at least in the vicinity of the male connector tip 306. A side surface 316 continues to extend along the barrel 304 to provide an input surface that a user can grip so as to pivot the lever member 314 relative to the barrel 304.

It will be appreciated that the lever member 314 is resiliently biased into a first position (seen in FIGS. 24a and 24b)

by a spring tongue 322 that has been cut out from one of the side surfaces 316. It will further be appreciated that the front surface 318 of the lever member 314 is provided with a catch member 324 which is pivoted away from the male connector tip 306 in this first position. When the lever member 314 is squeezed towards the barrel 304 of the syringe 302, against the resilient bias of the spring tongue 322, then the front surface 318 moves forwards along the male connector tip 306 to a second position seen in FIGS. 24c and 24d. In FIG. 24e the lever member 314 is shown separate from the syringe barrel 304. In FIG. 24f it can be seen that the syringe barrel 304 has two axles 335 integrally moulded at its forward end, so that the lever member 314 can be pivotally mounted with a fixed axis defined by the axles 335.

Operation of the disconnecting and catch mechanism may be understood with reference to FIGS. 25a and 25b. In FIG. 25a the syringe 302 is shown with the lever member 314 resiliently biased into its first position when a female hub 310 carrying a hypodermic needle 312 is connected onto the male connector tip 306 with a friction fit e.g. a standard Luer slip connection. In this first position the curved front surface 318 of the lever member 314 is not pushing against the female hub 310 and the catch member 324 is not in contact with the female hub 310. In this first position the syringe 302 may be operated e.g. by pushing the plunger 308 into the barrel 304 containing a fluid to be transferred or by pulling the plunger 308 out of the barrel 304 so as to withdraw a fluid. Once a fluid transfer procedure such as an injection has been completed, the lever member 314 may be squeezed down against the barrel 304 so as to release the friction fit between the female hub 310 and the male connector tip 306. As the lever member 314 is pivoted down against the resilient bias of its spring tongue 322, the front surface 318 moves forward along the male connector tip 306 so as to push against the female hub 310. Moreover, it will be appreciated from FIG. 25b that as the lever member 314 moves the front surface 318 towards it second position, the catch member 324 pivots around so as to engage against a side of the female hub 310. This may be aided by a rim 311 around the bottom edge of the hub 310 so that the catch 324 grips onto the rim 311. However, even without such a rim 311 the catch 324 may still prevent the female hub 310 from being pushed away from the male connector tip 306 by virtue of a frictional engagement against a side surface of the hub 310.

In this second position (FIG. 25b) the friction fit of the Luer slip or other tapered connection has been loosened, but the female hub 310 is not free by virtue of the catch member 324. A user may hold the syringe 302 in this position while it is located over a sharps bin or other disposal unit. Once a user is ready to release the female hub 310 from the catch, it is merely left to let go of the lever member 314 so that it pivots back towards its first position under the resilient bias of the spring tongue 322. As the front surface 318 of the lever member 314 pivots back from its second position, the catch member 324 is moved away from the female hub 310 so that the hub 310 and needle 312 are free to fall away from the syringe 302 and safely into the sharps bin. An advantage of providing the lever member 314 with such a catch member 324 is that the female hub 310 carrying a needle 312 cannot be forcibly ejected from the syringe 302 by operation of the lever member 314. However the lever member 314 still provides an amplified force that is very effective in loosening the friction fit of the Luer slip connection.

There is seen in FIGS. 26a-26d a second embodiment of a disconnecting and catch mechanism for a syringe 402, 402'. The only difference between FIGS. 26a and 26b is that the syringe 402 is designed for a volume of 10 ml while the syringe 402' is designed for a volume of 2-3 ml. The syringes 402, 402' are very similar to those already described with respect to FIGS. 24 and 25, and therefore components having like reference numbers will not be described again. However, it can be seen that the lever member 414 does not include a spring tongue and instead, as can be seen from FIG. 26c, a spring member 422 is mounted on the syringe barrel 404. The spring member 422 may be integrally moulded with the syringe barrel 404 or it may be a separate member connected thereto. In any case, the spring member 422 has the same effect of resiliently biasing the lever member 414 away from the syringe barrel 404. In FIG. 26d the lever member 414 is shown moulded from a transparent plastics material and it can be seen that a pair of sockets 435' are moulded into an inner surface of the lever member 414 so as to mount onto the axles 435 seen in FIG. 26c. The lever member 414 is provided with a catch member 424 on its front surface and operates in the same way as described above in relation to FIGS. 25a and 25b.

It will be appreciated that the catch mechanism may take a variety of different forms and is not limited to a protruding member of the type described so far. In a third embodiment of a lever member 414' shown in FIG. 27, the catch mechanism comprises a pair of fingers 424a, 424b rather than a single catch member. These fingers 424a, 424b may be may of a stiff e.g. plastics material or of a resilient e.g. plastics material.

Some further embodiments of different disconnecting and catch mechanisms are illustrated in FIGS. 28 to 41. In all of these embodiments there is shared the same basic principle of operation, in which a lever member is pivotally mounted to a syringe barrel so as to have its front surface movable between a first position proximal to the barrel and a second position spaced towards a distal end of the male connector tip so as to release the friction fit with a corresponding female hub e.g. carrying a needle, and a catch mechanism arranged to retain the female hub after it has been released from the friction fit by the lever member moving towards the second position. Accordingly only features of each embodiment which are different to those above will be described in any detail.

Figures 28A, 28B, 28C:
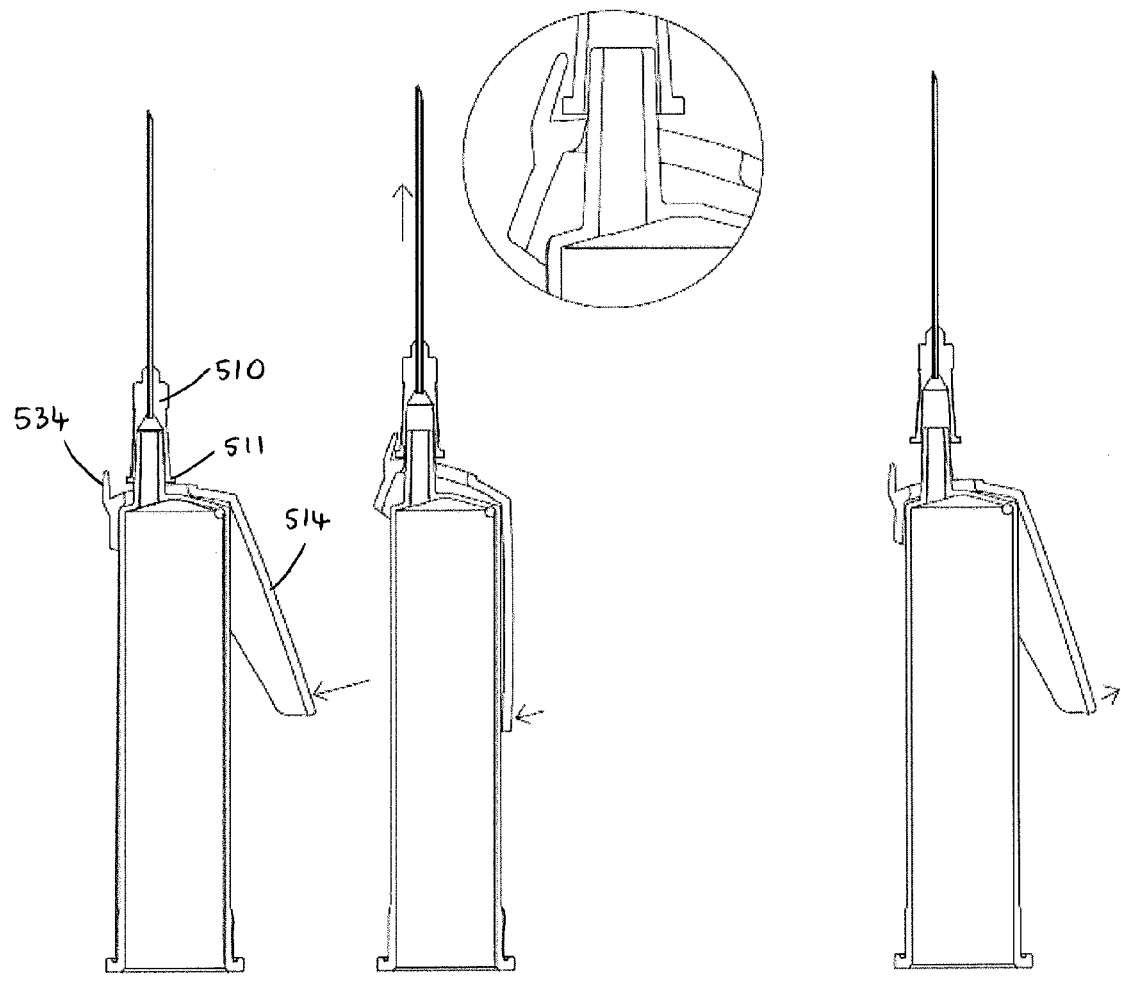
FIGS. 28a-28c show a third embodiment of a disconnecting and catch mechanism for a syringe.
Figures 29A, 29B, 29C:
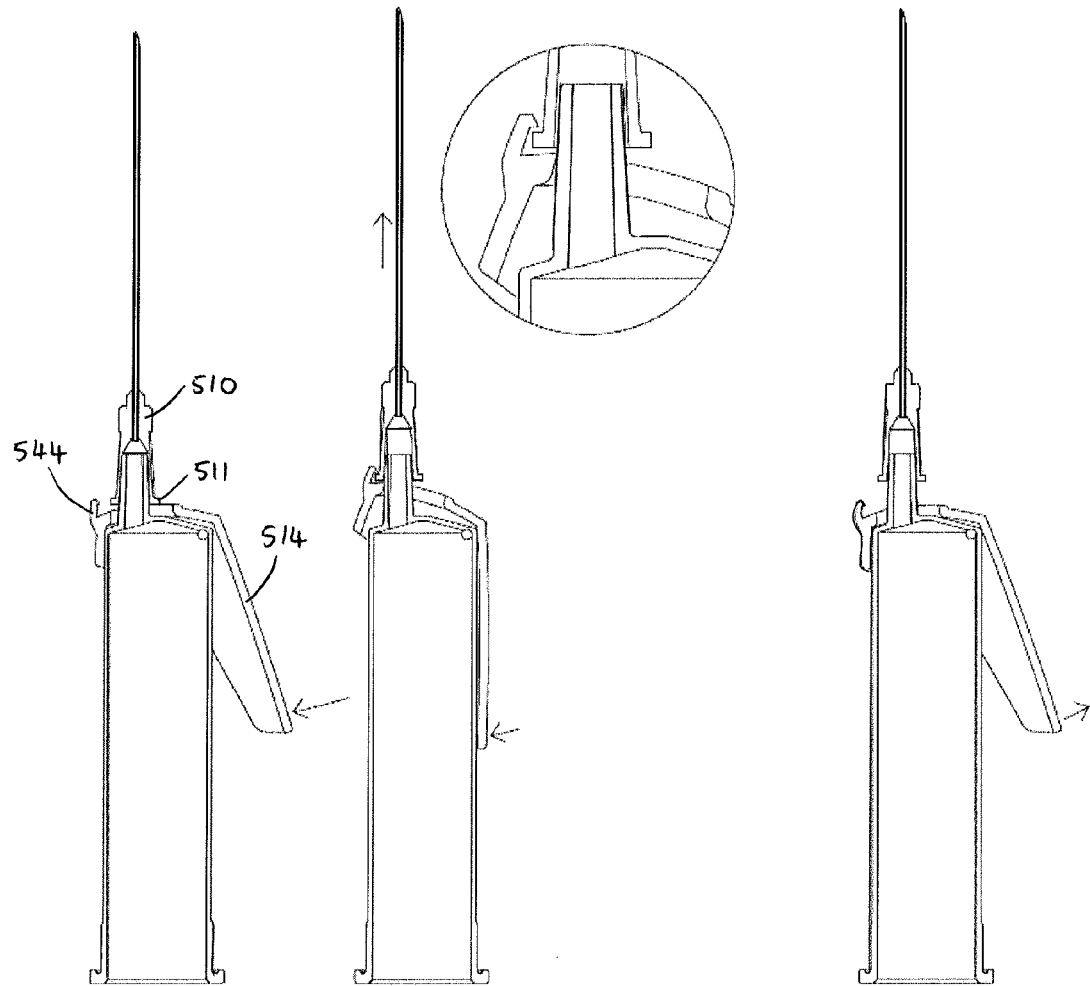
FIGS. 29a-29c show a fourth embodiment of a disconnecting and catch mechanism for a syringe.
Figures 30A, 30B, 30C:
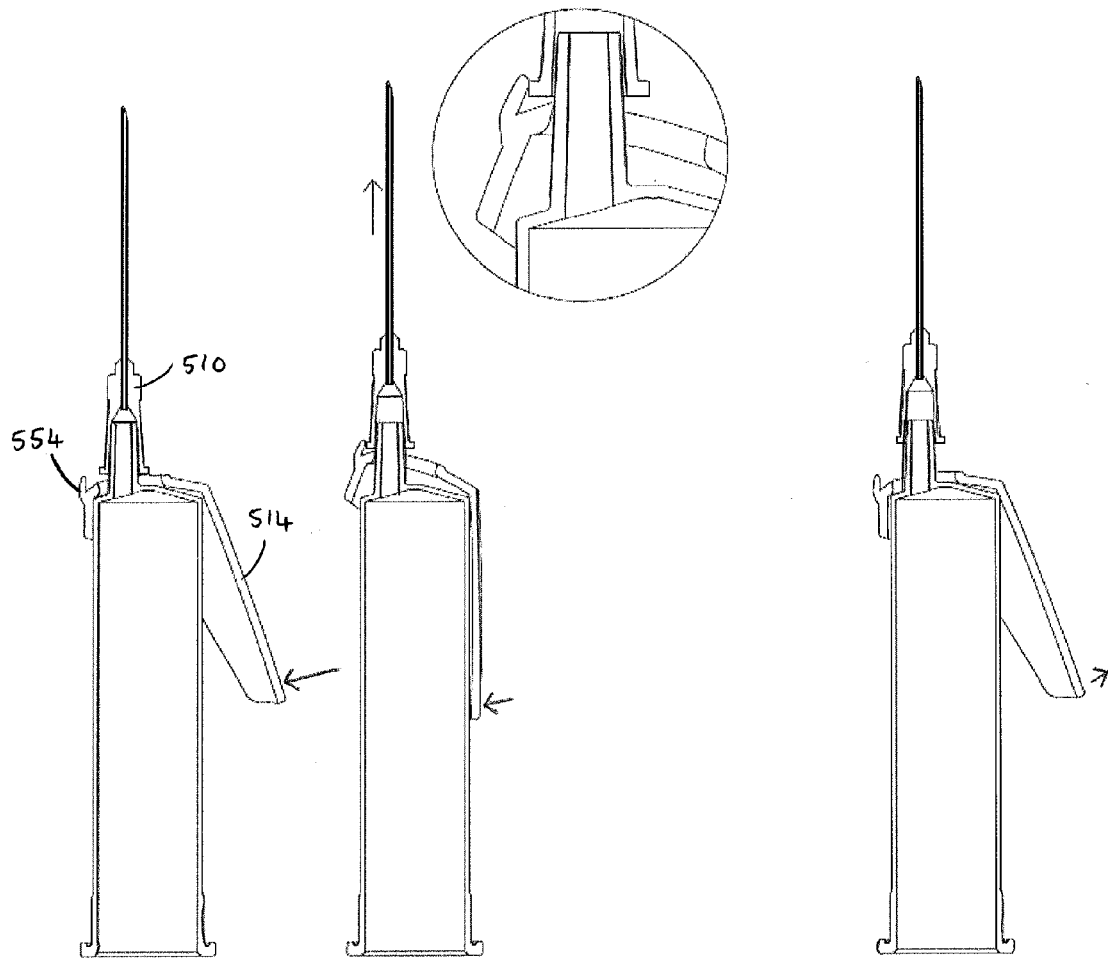
FIGS. 30a-30c show a fifth embodiment of a disconnecting and catch mechanism for a syringe.
Figures 31A, 31B, 31C:
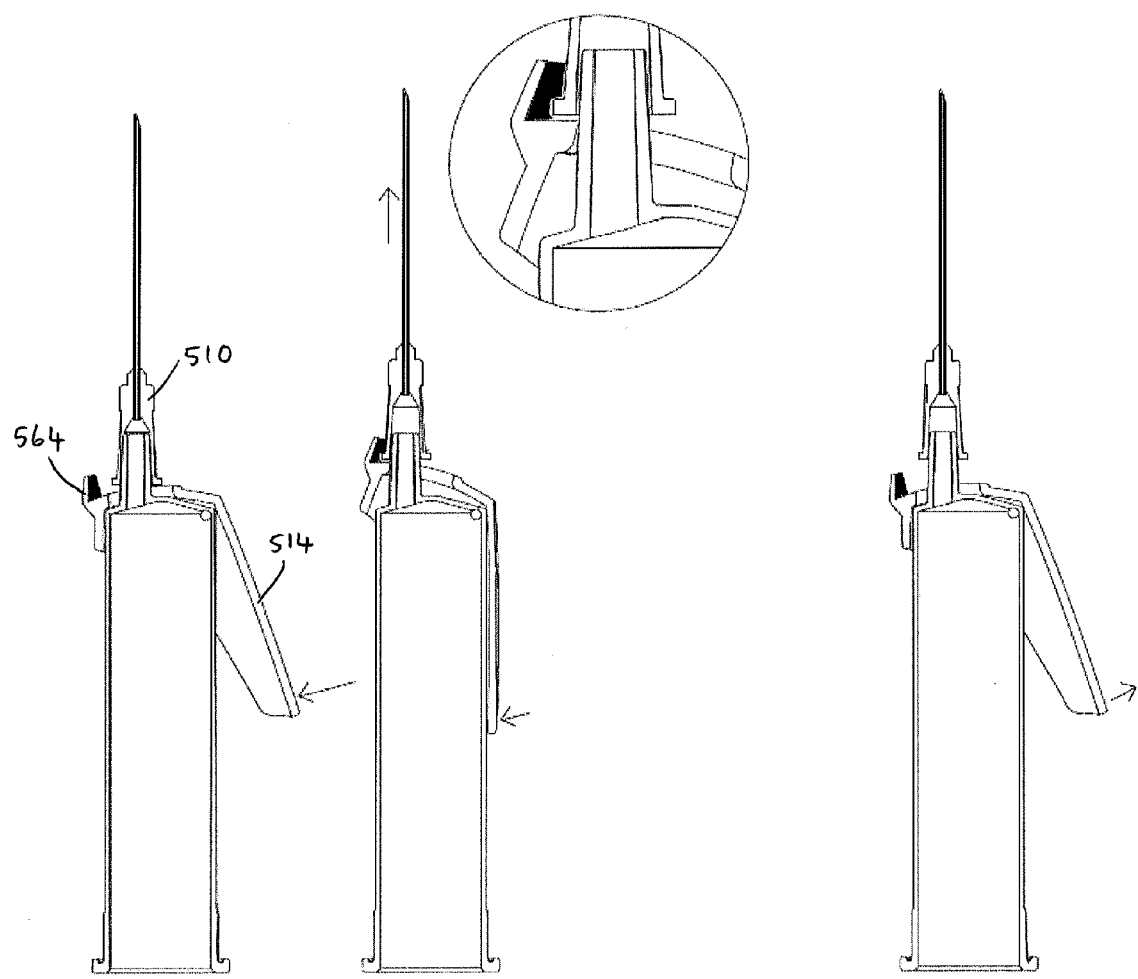
FIGS. 31a-31c show a sixth embodiment of a disconnecting and catch mechanism for a syringe.

In FIGS. 28a-28c there is shown a further embodiment in which the lever member 514 comprises a catch member 534 that extends forward to engage against the female hub 510, for example dragging across a rim 511 of the hub 510. In FIGS. 29a-29c there is shown a further embodiment in which the lever member 514 comprises a catch member 544 that extends forward and hooks over the rim 511 of the hub 510. This may provide a more reliable catch and/or an audible "click" when the catch is engaged e.g. to reassure a user that the loosened hub 510 can not fall away until the lever member 514 is released. In FIGS. 30a-30c there is shown a further embodiment in which the lever member 514 comprises a catch member 554 that does not extend as far forward. Even though the catch member 554 is shorter, it still makes physical contact with the female hub 510 and therefore holds the hub with friction as long as the lever member 514 is in its second position. In FIGS. 31a-31c there is shown a further embodiment in which the lever member 514 comprises a catch member 564 that engages against the female hub 510 with a compressible e.g. foam pad so as to increase the frictional hold.

In FIGS. 32a-32c there is shown a further embodiment in which a catch mechanism is provided by the lever member 514 having a front surface 518 that is adhesive. When the lever member 514 is pivoted from its first position (FIG. 32a) towards its second position (FIG. 32b), the front surface 518 is pushed against the hub 510 and furthermore sticks to the hub 510 so that it can not fall away from the syringe even once the friction fit has been released. The hub 510 may then be manually pulled away from the lever member 514, as shown in FIG. 32c, or the action of the lever member pivoting back towards its first position (e.g. under a resilient bias) could release the adhesive catch.

Figure 33D:
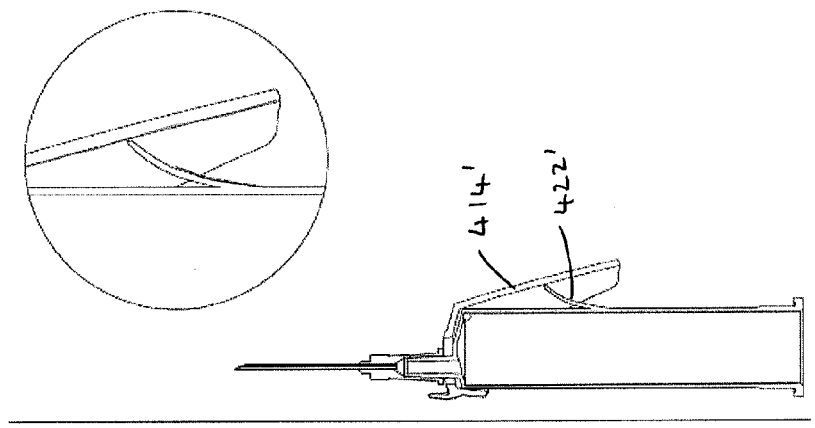
FIGS. 33a-33d show some variants of a spring arrangement for a disconnecting and catch mechanism.
Figure 33C:
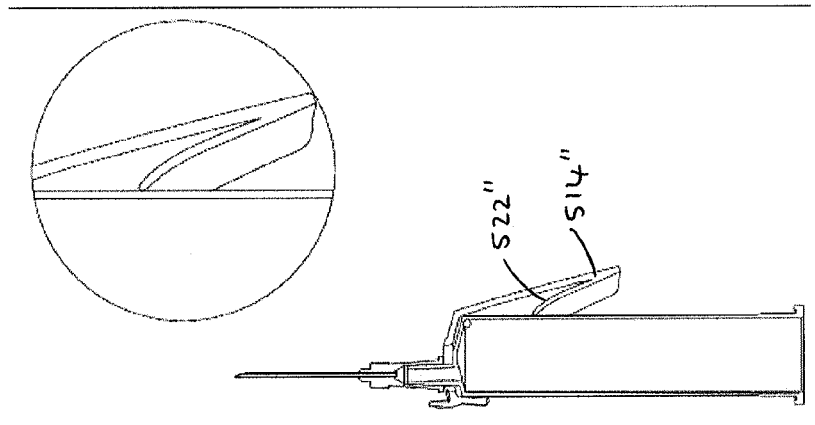
Figure 33B:
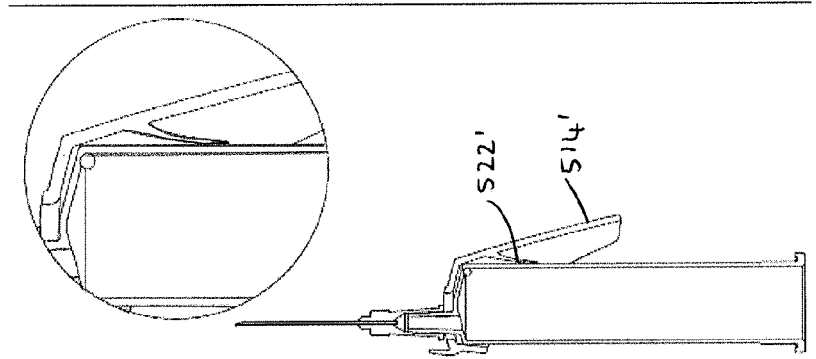
Figure 33A:
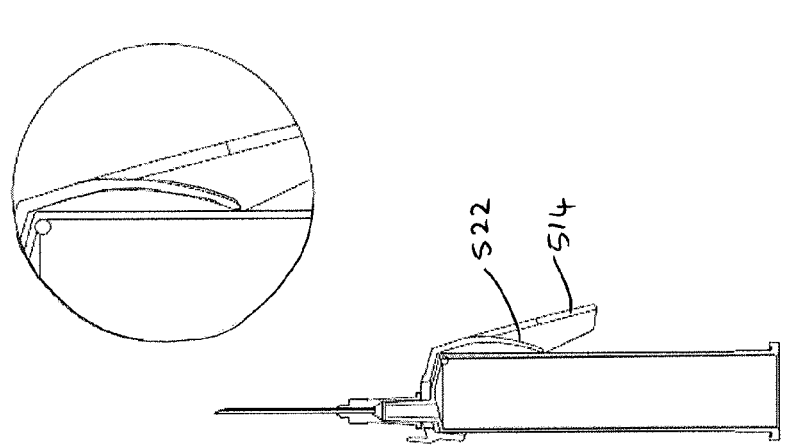

In any of the embodiments seen in FIGS. 28 to 32, the lever member 514 may be mounted so as to freely pivot relative to the syringe barrel 504 or the lever member 514 may be resiliently biased to the first position in which the catch mechanism does not engage the hub 510. This can allow the catch to be released automatically as soon as a user is no longer holding down the lever member 514. FIGS. 33a to 33d illustrate some different arrangements for a resiliently biased lever member 514. In FIG. 33a the lever member 514 includes a spring tongue 522 of the type described above with respect to FIGS. 24 and 25, i.e. that curves backwards towards the barrel 504. In FIG. 33b the lever member 514' includes a spring tongue 522' that curves the opposite way towards the barrel 504. In FIG. 33c the lever member 514" includes a spring tongue 522" that curves forwards towards the barrel 504. In FIG. 33d the syringe barrel 504 is provided with a spring tongue 422' that curves out towards the lever member 414', in a similar manner to that described above with respect to FIG. 26. Any of these lever members 514, 514', 514", 414' may be used in conjunction with one of the catch mechanisms seen in FIGS. 24 to 32.

Figure 35:
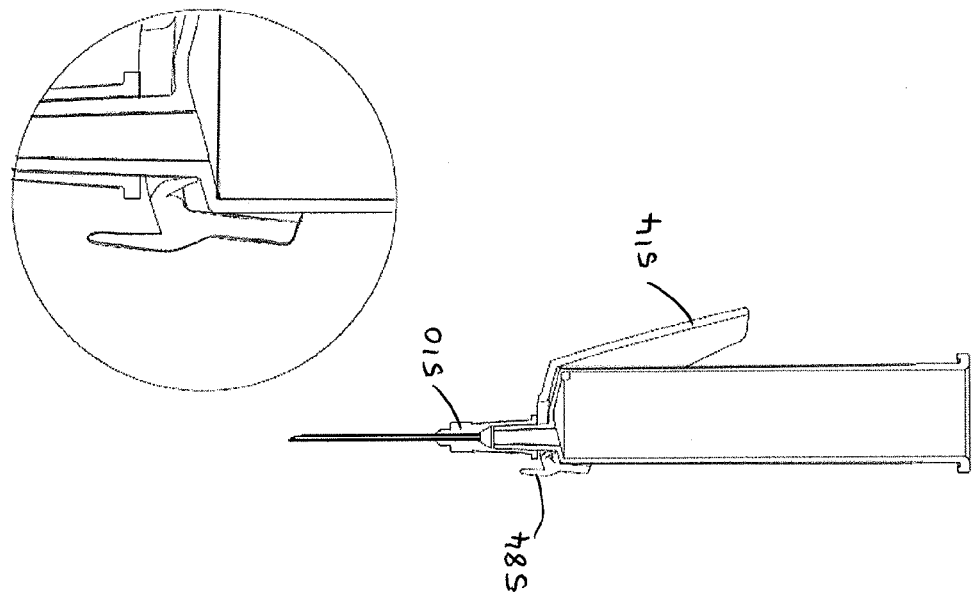
FIG. 35 shows a ninth embodiment of a disconnecting and catch mechanism for a syringe.
Figure 34B:
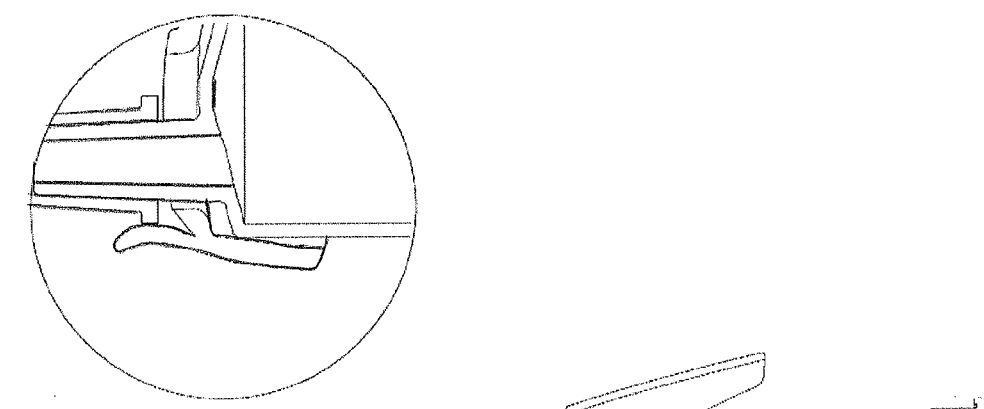
FIGS. 34a and 34b show an eighth embodiment of a disconnecting and catch mechanism for a syringe.
Figure 34A:
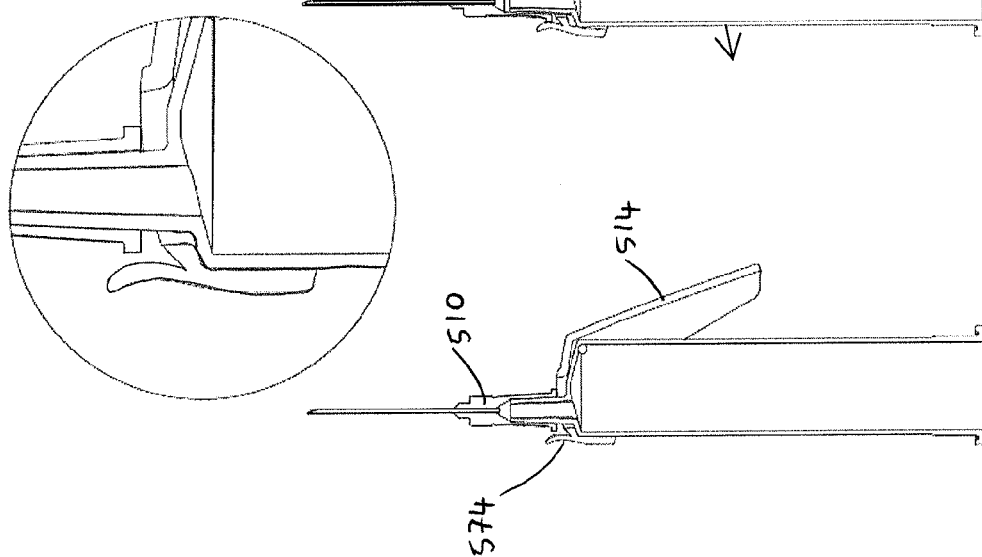

FIGS. 34 and 35 illustrate some alternative embodiments in which the catch mechanism is released by its own resilient bias. In FIGS. 34a and 34b the catch member 574 is made from an elastic material, such as an elastomer, which is compressed when the catch engages against the hub 510 and therefore pushes against the lever member 514. When a user reduces the force applied to the lever member 514 then the catch member 574 can relax to release its grip on the hub 510. In FIG. 35 the catch member 584 takes the form of a resilient hinge that acts in the same way.

Figures 36A, 36B:
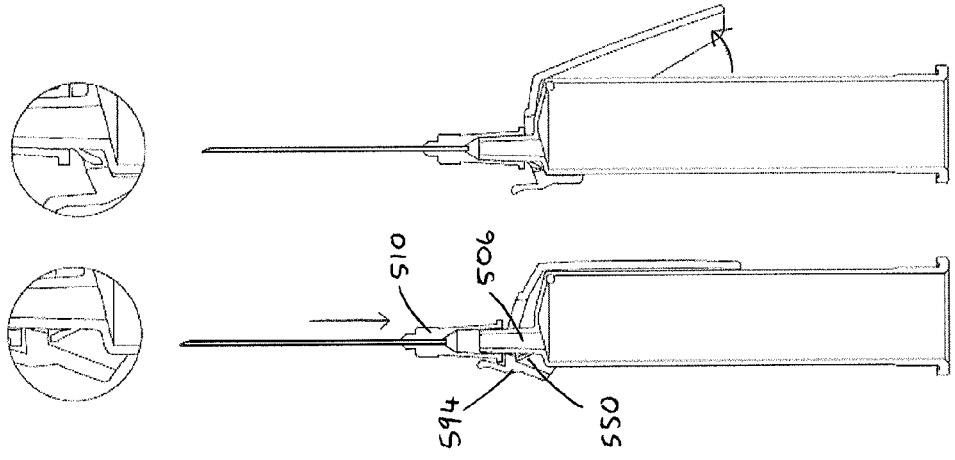
FIGS. 36a and 36b show a 10th embodiment of a disconnecting and catch mechanism for a syringe.
Figures 37A, 37B:
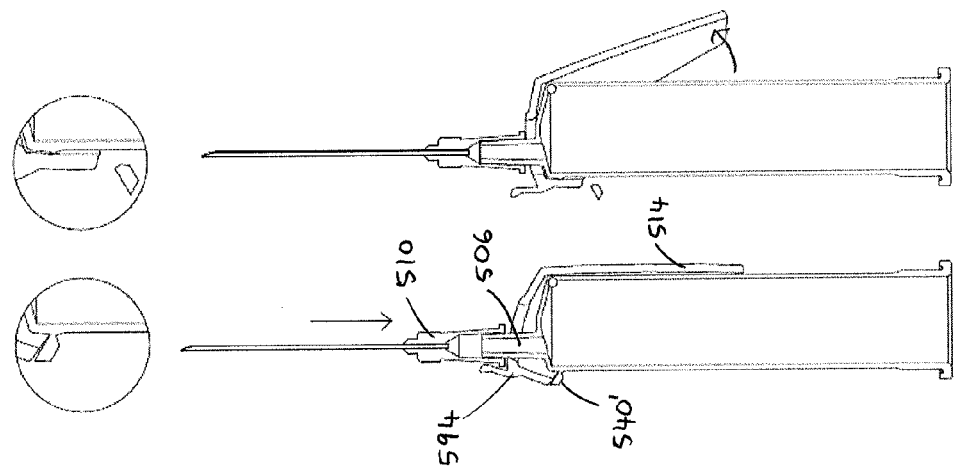
FIGS. 37a and 37b show an 11th embodiment of a disconnecting and catch mechanism for a syringe.
Figures 38A, 38B:
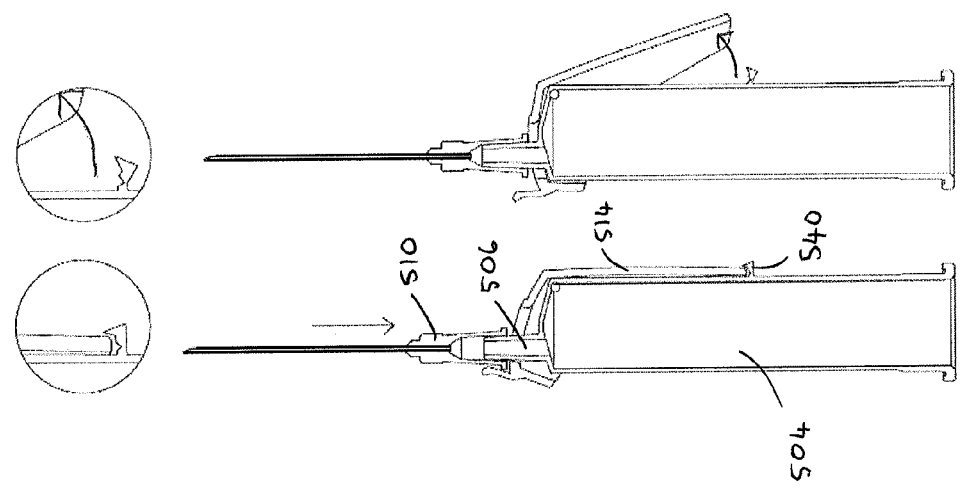
FIGS. 38a and 38b show a 12th embodiment of a disconnecting and catch mechanism for a syringe.

FIGS. 36 to 38 illustrate some embodiments where the lever member 514 is primed by connecting a needle hub 510. In FIGS. 36a and 36b it can be seen that the lever member 514 is initially locked to the syringe barrel 504 by a breakable tab 540. When a hub 510 is connected to the tip 506, the lever member 514 is forced to pivot outwardly and snaps the tab 540 so as to provide an audible and/or visible indication that the hub 510 has formed a friction fit and the lever member 514 is primed ready for use. In FIGS. 37a and 37b the lever member 514 is initially locked to the syringe barrel 504 by a breakable tab 540' arranged under the catch 594. Again, the action of connecting a needle hub 510 to the tip 506 forces the lever member 514 to pivot and the catch 594 then breaks the tab 540'. In FIGS. 38a and 38b the lever member 514 is initially locked by a deformable member 550 that bears against the catch 594.

Figure 40C:
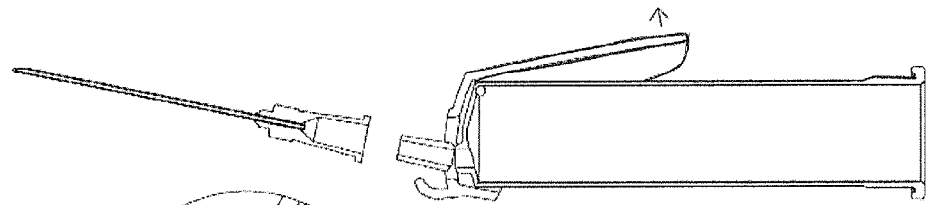
FIGS. 40a-40c show a 14th embodiment of a disconnecting and catch mechanism for a syringe.
Figure 40B:
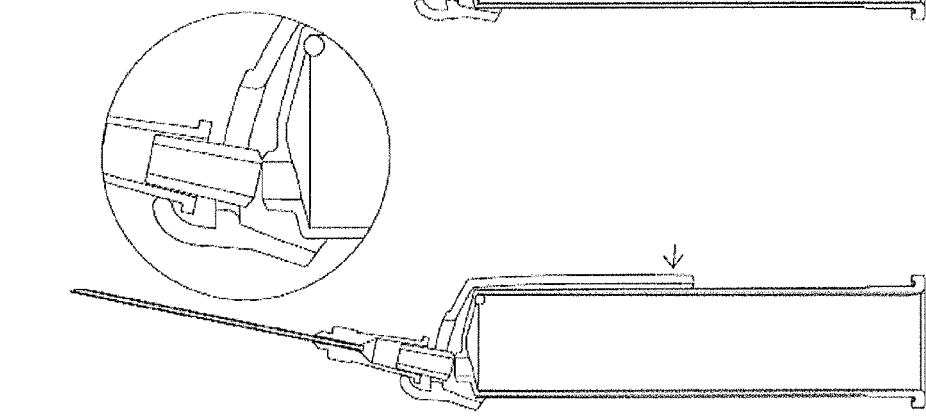
Figure 40A:
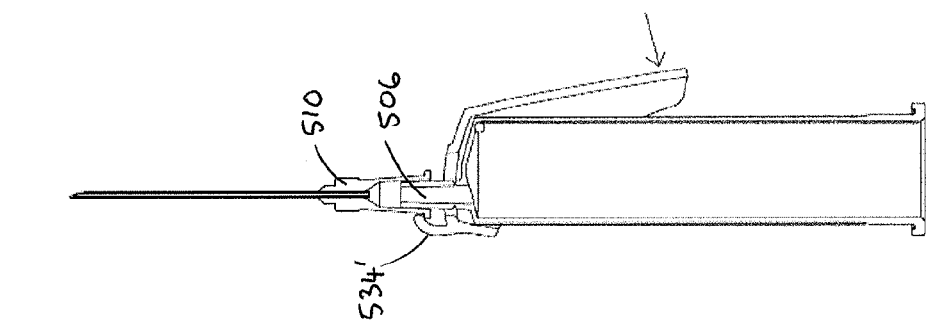
Figure 39G:
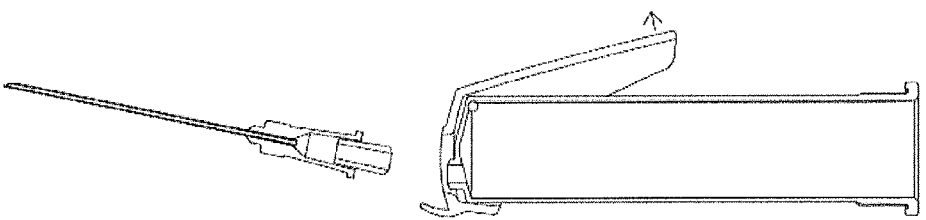
Figure 39F:
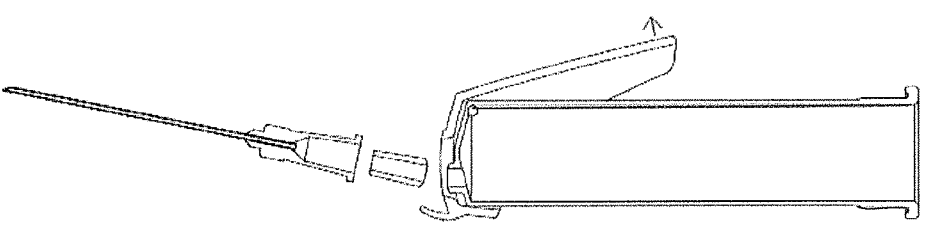

FIGS. 39 and 40 illustrate some embodiments where the male tip 506 is broken when the lever member 514 pivots towards the second position to release the friction fit. The slot 520 through which the tip 506 passes is designed to push against the tip 506 as the lever member 514 rotates. The tip is formed with a thinned region of material so that the pressure applied by the lever member 514 causes the tip to at least partially break. This ensures that the syringe can not be used more than once, for example after injecting a vaccine. FIGS. 39a-39d show the tip 506 being broken as the lever member 514 pivots between the first and second positions and the catch 534 is engaged. FIG. 39e shows that the broken tip 506 may be left semi-attached while the hub 510 is released from the catch mechanism. FIG. 39f shows that the tip 506 may instead break off completely and fall away with the hub 510. FIG. 39g shows another alternative situation where the tip 506 breaks off and stays semi-connected to the hub 510 so that they fall away together. FIGS. 40a-40c show a different catch mechanism 534' that grips the hub 510 more tightly to add leverage when breaking the tip 506.

Figure 41C:
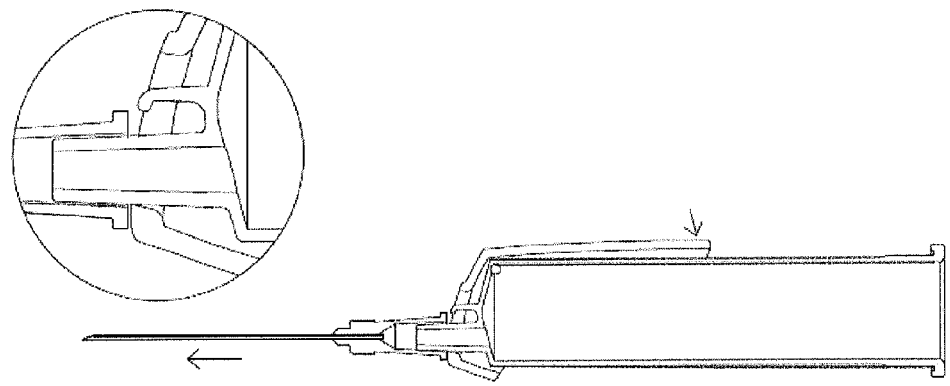
FIGS. 41a-41c show a 15th embodiment of a disconnecting and catch mechanism for a syringe.
Figure 41B:
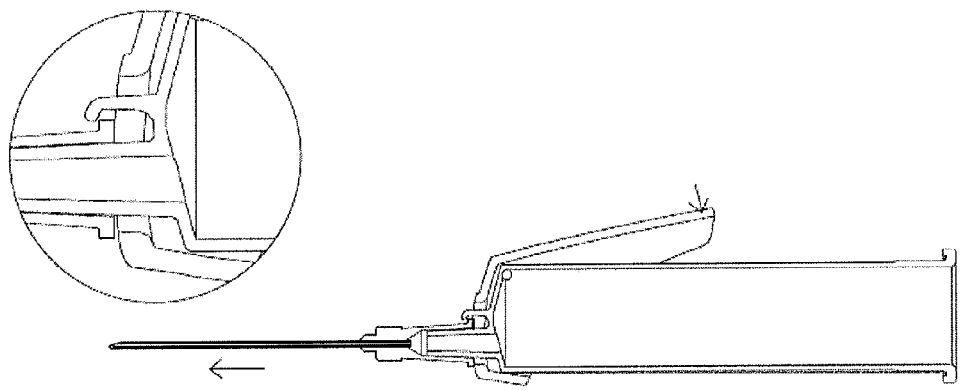
Figure 41A:
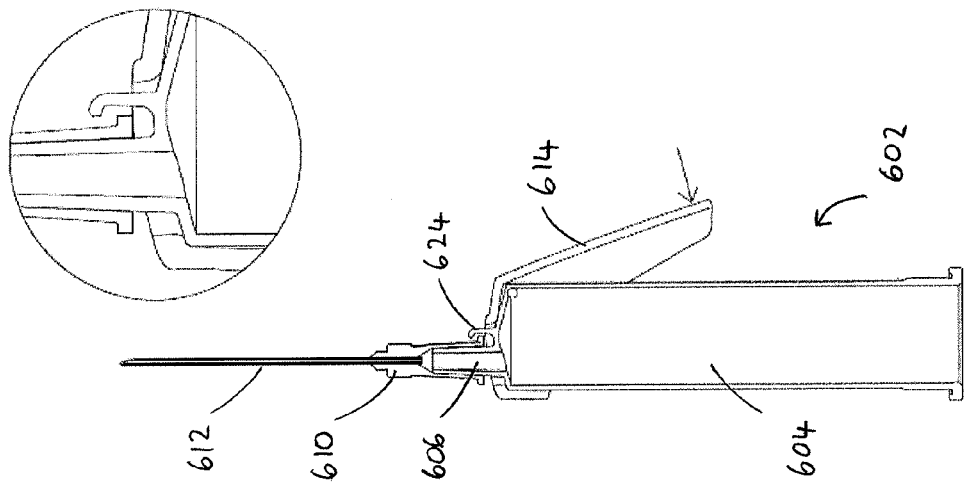

In the embodiments of FIGS. 24 to 40, the catch mechanism has so far been illustrated as part of the disconnecting mechanism e.g. a catch member provided on the lever member. However it will be appreciated that the catch mechanism may instead by provided by the syringe barrel. An exemplary embodiment is seen in FIGS. 41a to 41c. This syringe 602 comprises a lever member 614 pivotally mounted to the barrel 604 so as to release the friction fit between the male connector tip 606 and female hub 610 e.g. carrying a needle 612. A catch member 624 extends forward from the barrel 604 far enough that it does not contact the hub 610 when it is connected to the tip 506 (FIG. 41a). As the lever member 614 pivots towards its second position to release the friction fit (FIG. 41b), the hub 610 is pushed forwards into engagement with the stationary catch 624. The catch 624 prevents the needle hub 610 from shooting away from the syringe with force. Instead, the force of the lever is used to overcome the catch 624 so that the hub 610 is slowed before it is finally free (FIG. 41c).

While the invention has been described in the context of various embodiments, these are merely examples and features of one embodiment may be combined with those of another and vice versa. Furthermore, although not illustrated in all of the embodiments, a locking or blocking member may be provided to prevent the disconnecting lever, sleeve, etc. from moving out of its first position until it is desired to be able to operate the disconnecting mechanism. The disconnecting mechanism could be disabled, for example, by a blocking interaction with a cap on the syringe needle (where provided). Further variants and suitable features will be apparent to the skilled person. The scope of the invention is defined by the following claims.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. A fluid transfer device comprising:
   a fluid chamber in communication with a male connector tip, the male tip being tapered to form a friction fit when inserted in a corresponding female hub;
   a disconnecting member moveable relative to the male connector tip between a first position proximal to the fluid chamber and a second position spaced from the first position towards a distal end of the male connector tip so as to release the friction fit, wherein the disconnecting member is biased into the first position by a resilient bias; and
   a catch means arranged to catch the female hub after it has been released from the friction fit by the disconnecting member moving towards the second position, wherein the catch means is arranged to be automatically released by the disconnecting member moving from the second position back to the first position under said resilient bias.

2. A device according to claim 1, wherein the catch means is provided by the disconnecting member.

3. A device according to claim 1, wherein the disconnecting member comprises one or more lever members pivotally mounted to the device with a front surface moveable along the male connector tip between the first and second positions.

4. A device according to claim 3, wherein the one or more lever member(s) comprise a front surface that is substantially transverse to the axis of the male connector tip and one or more side surfaces that extend in a direction substantially parallel to the axis of the male connector tip.

5. A device according to claim 1, further comprising means for locking the disconnecting member in the second position.

6. A device according to claim 1, wherein the device comprises a spring member arranged to resiliently bias the disconnecting member into the first position and wherein the spring member is integrated with the disconnecting member.

7. A device according to claim 4, wherein the side surface(s) form a shroud extending back from the front surface towards the fluid chamber such that the shroud at least partially surrounds the fluid chamber.

8. A device according to of claim 4, wherein the front surface and the side surface(s) are integrally formed as a single plastics moulding.

9. A device according to claim 4, wherein the lever member(s) is/are pivotally mounted such that the front surface moves from the first position to the second position when the side surface(s) is/are pivoted towards the fluid chamber.

10. A device according to claim 4, further comprising means for mounting the lever member(s) to the fluid chamber, wherein the side surface(s) engage with the mounting means.

11. A device according to claim 4, wherein the lever member(s) is/are pivotally mounted such that the side surface(s) pivots away from the fluid chamber when the front surface is moved to the first position by connecting a female hub to the male connector tip.

12. A device according to claim 3, wherein the front surface is arranged to move substantially linearly relative to the axis of the male connector tip between the first and second positions.

13. A device according to claim 3, wherein the front surface of the lever member(s) comprises a curved surface.

14. A device according to claim 1, wherein the female hub comprises a cannula or hypodermic needle and the fluid chamber is part of a syringe.

15. A device according to claim 1, wherein the disconnecting member is removably mounted to the device.

16. A device according to claim 1, wherein the disconnecting member is moveably mounted to mounting means integrated with the fluid chamber.

17. A device according to claim 1, wherein the disconnecting member is attached to an aft end of the male connector tip by an attachment collar.

18. A device according to claim 17, wherein the device comprises a spring member arranged to resiliently bias the disconnecting member into the first position and wherein the spring member is integrated with the disconnecting member.

19. A device according to claim 3, wherein the lever member(s) is/are attached to an aft end of the male connector tip by an attachment collar.

20. A disconnecting mechanism for a fluid transfer device that comprises a fluid transfer tip tapered outwardly from a forward end to an aft end to form a friction fit when inserted in a corresponding female hub, the mechanism comprising:
  an attachment collar to attach the mechanism to the aft end of a tip;
  a disconnecting member moveable relative to the collar against a resilient bias to a second position spaced away from the collar and towards the forward end of the tip; and
  a catch means arranged to catch the female hub after it has been released from the friction fit by the disconnecting member moving towards the second position;
  wherein the catch means is automatically released by the disconnecting member moving back from the second position under the resilient bias.

* * * * *